US012612364B2

(12) United States Patent
Clark

(10) Patent No.: US 12,612,364 B2

(45) Date of Patent: Apr. 28, 2026

(54) **SALTS AND SOLID FORMS OF 4-HYDROXY-*N,N*-DIISOPROPYL-TRYPTAMINE HEMI-GLUTARATE AND HEMI-SUCCINATE**

(71) Applicant: Terran Biosciences Inc., Miami Beach, FL (US)

(72) Inventor: Samuel Clark, Miami Beach, FL (US)

(73) Assignee: Terran Biosciences Inc., Miami Beach, FL (US)

( * ) Notice: Subject to any disclaimer, the term of this patent is extended or adjusted under 35 U.S.C. 154(b) by 0 days.

(21) Appl. No.: 19/408,193

(22) Filed: Dec. 3, 2025

(65) Prior Publication Data

US 2026/0085041 A1 Mar. 26, 2026

Related U.S. Application Data

(63) Continuation of application No. 19/241,602, filed on Jun. 18, 2025, which is a continuation of application No. 18/726,486, filed as application No. PCT/US2023/060190 on Jan. 6, 2023, now abandoned.

(60) Provisional application No. 63/357,319, filed on Jun. 30, 2022, provisional application No. 63/357,499, filed on Jun. 30, 2022, provisional application No. 63/296,962, filed on Jan. 6, 2022, provisional application No. 63/297,061, filed on Jan. 6, 2022, provisional application No. 63/296,964, filed on Jan. 6, 2022, provisional application No. 63/297,057, filed on Jan. 6, 2022.

(51) Int. Cl.

| | |
|---|---|
| ***C07D 209/16*** | (2006.01) |
| ***A61K 31/36*** | (2006.01) |
| ***A61K 31/4045*** | (2006.01) |
| ***A61K 45/06*** | (2006.01) |
| ***A61P 25/32*** | (2006.01) |

(52) U.S. Cl.

CPC ............ *C07D 209/16* (2013.01); *A61K 31/36* (2013.01); *A61K 31/4045* (2013.01); *A61K 45/06* (2013.01); *A61P 25/32* (2018.01)

(58) Field of Classification Search

None

See application file for complete search history.

(56) References Cited

U.S. PATENT DOCUMENTS

| | | | | |
|---|---|---|---|---|
| 2014/0050787 | A1 | 2/2014 | Tygesen et al. | |
| 2019/0142851 | A1 | 5/2019 | Chadeayne | |
| 2020/0375967 | A1 | 12/2020 | Stamets | |
| 2021/0403425 | A1 | 12/2021 | Bryson | |
| 2025/0066299 | A1 * | 2/2025 | Duncton .............. | C07D 209/16 |

* cited by examiner

*Primary Examiner* — Jeffrey S Lundgren

*Assistant Examiner* — Michael J Schmitt

(74) *Attorney, Agent, or Firm* — Clark & Elbing LLP

(57) ABSTRACT

Disclosed herein are salts and solid forms of 4-hydroxy-N, N-diisopropyltryptamine hemi-glutarate (4-OH-DIPT), e.g., 4-OH-DIPT hemi-glutarate, 4-OH-DIPT hemi-succinate, 4-OH-DIPT hemi-succinate hydrochloride, and 4-OH-DIPT hemi-glutarate hydrochloride. The solid form may be a salt and/or a crystalline form of the 4-OH-DIPT, such as a polymorph of 4-OH-DIPT or a salt thereof. Also disclosed are methods for making the solid forms and methods for administering the solid forms. The disclosed solid forms of 4-OH-DIPT are useful for treating neurological disease and/or a psychiatric disorder in a subject.

6 Claims, 1 Drawing Sheet

SALTS AND SOLID FORMS OF 4-HYDROXY-*N,N*-DIISOPROPYLTRYPTAMINE HEMI-GLUTARATE AND HEMI-SUCCINATE

SUMMARY

Disclosed herein are solid forms of 4-hydroxy-N,N-diisopropyltryptamine hemi-glutarate (4-OH-DIPT hemi-glutarate), including salts, solid forms of the compound and salts thereof, as well as polymorphs of solid forms.

Also disclosed are methods for making the solid forms and methods for using the solid forms of 4-OH-DIPT hemi-glutarate. In some embodiments, the solid form of 4-OH-DIPT hemi-glutarate is a polymorph of the free base form of the compound. In other embodiments, the solid form of 4-OH-DIPT hemi-glutarate is a salt, and maybe a polymorph of the salt. The salt may be formed from an acid selected from fumaric acid, galactaric (mucic) acid, naphthalene-1,5-disulfonic acid, citric acid, sulfuric acid, d-glucuronic acid, ethane-1,2-disulfonic acid, lactobionic acid, p-toluenesulfonic acid, D-glucoheptonic acid, thiocyanic acid, (−)-L-pyroglutamic acid, methanesulfonic acid, L-malic acid, dodecylsulfuric acid, hippuric acid, naphthalene-2-sulfonic acid, D-gluconic acid, benzenesulfonic acid, D,L-lactic acid, oxalic acid, oleic acid, glycerophosphoric acid, succinic acid, ethanesulfonic acid 2-hydroxy, glutaric acid, L-aspartic acid, cinnamic acid, maleic acid, adipic acid, phosphoric acid, sebacic acid, ethanesulfonic acid, (+)-camphoric acid, glutamic acid, acetic acid, xinafoic acid, hydrobromic acid, or a combination thereof. In any embodiments, a stoichiometric ratio of acid to 4-OH-DIPT hemi-glutarate is from about 0.4 to about 2.2, such as from about 0.5 to about 2, or from about 0.5, 1 or 2.

In any embodiments, the solid form may be a crystalline solid, a hydrate, or a combination thereof. The crystalline solid may be substantially a single form, such as a polymorph form. And the polymorph may be selected to have one or more desired properties, particularly improved properties, such as physical properties, chemical properties, pharmacokinetic properties, or a combination thereof. The one or more desired properties may comprise melting point, glass transition temperature, flowability, thermal stability, mechanical stability, shelf life, stability against polymorphic transition, hygroscopic properties, solubility in water and/or organic solvents, reactivity, compatibility with excipients and/or delivery vehicles, bioavailability, absorption, distribution, metabolism, excretion, toxicity including cytotoxicity, dissolution rate, half-life, or a combination thereof.

Also disclosed herein are embodiments of a pharmaceutical composition, comprising a solid form of a disclosed compound, and a pharmaceutically acceptable excipient.

A method for administering the solid form of 4-OH-DIPT hemi-glutarate also is disclosed herein. In some embodiments, the method comprises administering to a subject an effective amount of a solid form of 4-OH-DIPT hemi-glutarate, or a pharmaceutical composition thereof. In some embodiments, the subject is suffering from a neurological disease or a psychiatric disorder, or both, such as a neurodegenerative disorder. The neurological disorder or psychiatric disorder, or both, may comprise depression, addiction, anxiety, or a post-traumatic stress disorder, and/or the neurological disorder or psychiatric disorder, or both, may comprise treatment resistant depression, suicidal ideation, major depressive disorder, bipolar disorder, schizophrenia, or substance use disorder. In some embodiments, the neurological disorder or psychiatric disorder, or both, comprises stroke, traumatic brain injury, or a combination thereof.

The method may comprise further comprising administering an effective amount of an empathogenic agent and/or a 5-$HT_{2A}$ antagonist to the subject. The 5-$HT_{2A}$ antagonist may be selected from MDL-11,939, eplivanserin (SR-46,349), ketanserin, ritanserin, altanserin, acepromazine, mianserin, mirtazapine, quetiapine, SB204741, SB206553, SB242084, LY272015, SB243213, blonanserin, SB200646, RS102221, nefazodone, MDL-100,907, pimavanserin, nelotanserin and lorcaserin.

In any embodiments, administering the solid form of the compound comprises oral, parenteral, or topical administration. In certain embodiments, oral administration is used, but in other particular embodiments, administration is by injection, inhalation, intraocular, intravaginal, intrarectal or transdermal routes.

The foregoing and other objects, features, and advantages of the invention will become more apparent from the following detailed description.

Disclosed herein are solid forms of 4-hydroxy-N,N-diisopropyltryptamine hemi-succinate (4-OH-DIPT hemi-succinate), including salts, solid forms of the compound and salts thereof, as well as polymorphs of solid forms. In some embodiments, the solid form is not 4-OH-DIPT hemi-succinate hydrochloride.

Also disclosed are methods for making the solid forms and methods for using the solid forms of 4-OH-DIPT hemi-succinate. In some embodiments, the solid form of 4-OH-DIPT hemi-succinate is a polymorph of the free base form of the compound. In other embodiments, the solid form of 4-OH-DIPT hemi-succinate is a salt, and maybe a polymorph of the salt. The salt may be formed from an acid selected from fumaric acid, galactaric (mucic) acid, naphthalene-1,5-disulfonic acid, citric acid, sulfuric acid, d-glucuronic acid, ethane-1,2-disulfonic acid, lactobionic acid, p-toluenesulfonic acid, D-glucoheptonic acid, thiocyanic acid, (−)-L-pyroglutamic acid, methanesulfonic acid, L-malic acid, dodecylsulfuric acid, hippuric acid, naphthalene-2-sulfonic acid, D-gluconic acid, benzenesulfonic acid, D,L-lactic acid, oxalic acid, oleic acid, glycerophosphoric acid, succinic acid, ethanesulfonic acid 2-hydroxy, glutaric acid, L-aspartic acid, cinnamic acid, maleic acid, adipic acid, phosphoric acid, sebacic acid, ethanesulfonic acid, (+)-camphoric acid, glutamic acid, acetic acid, xinafoic acid, hydrobromic acid, or a combination thereof. In any embodiments, a stoichiometric ratio of acid to 4-OH-DIPT hemi-succinate is from about 0.4 to about 2.2, such as from about 0.5 to about 2, or from about 0.5, 1 or 2.

In any embodiments, the solid form may be a crystalline solid, a hydrate, or a combination thereof. The crystalline solid may be substantially a single form, such as a polymorph form. And the polymorph may be selected to have one or more desired properties, particularly improved properties, such as physical properties, chemical properties, pharmacokinetic properties, or a combination thereof. The one or more desired properties may comprise melting point, glass transition temperature, flowability, thermal stability, mechanical stability, shelf life, stability against polymorphic transition, hygroscopic properties, solubility in water and/or organic solvents, reactivity, compatibility with excipients and/or delivery vehicles, bioavailability, absorption, distribution, metabolism, excretion, toxicity including cytotoxicity, dissolution rate, half-life, or a combination thereof.

Also disclosed herein are embodiments of a pharmaceutical composition, comprising a solid form of a disclosed compound, and a pharmaceutically acceptable excipient.

A method for administering the solid form of 4-OH-DIPT hemi-succinate also is disclosed herein. In some embodiments, the method comprises administering to a subject an effective amount of a solid form of 4-OH-DIPT hemi-succinate, or a pharmaceutical composition thereof. In some embodiments, the subject is suffering from a neurological disease or a psychiatric disorder, or both, such as a neuro-degenerative disorder. The neurological disorder or psychiatric disorder, or both, may comprise depression, addiction, anxiety, or a post-traumatic stress disorder, and/or the neurological disorder or psychiatric disorder, or both, may comprise treatment resistant depression, suicidal ideation, major depressive disorder, bipolar disorder, schizophrenia, or substance use disorder. In some embodiments, the neurological disorder or psychiatric disorder, or both, comprises stroke, traumatic brain injury, or a combination thereof.

The method may comprise further comprising administering an effective amount of an empathogenic agent and/or a 5-$HT_{2A}$ antagonist to the subject. The 5-$HT_{2A}$ antagonist may be selected from MDL-11,939, eplivanserin (SR-46, 349), ketanserin, ritanserin, altanserin, acepromazine, mianserin, mirtazapine, quetiapine, SB204741, SB206553, SB242084, LY272015, SB243213, blonanserin, SB200646, RS102221, nefazodone, MDL-100,907, pimavanserin, nelotanserin and lorcaserin.

In any embodiments, administering the solid form of the compound comprises oral, parenteral, or topical administration. In certain embodiments, oral administration is used, but in other particular embodiments, administration is by injection, inhalation, intraocular, intravaginal, intrarectal or transdermal routes.

Disclosed herein are novel solid forms of 4-OH-DIPT hemi-glutarate hydrochloride. The solid form of 4-OH-DIPT hemi-glutarate hydrochloride may have at least one improved property compared to amorphous 4-OH-DIPT hemi-glutarate hydrochloride and to previously known crystalline forms of 4-OH-DIPT hemi-glutarate hydrochloride.

Also disclosed herein is a solid form of 4-OH-DIPT hemi-glutarate hydrochloride that is made by the method described in Examples 1 and/or 4. The solid form of 4-OH-DIPT hemi-glutarate hydrochloride made by the disclosed method may have at least one improved property compared to amorphous 4-OH-DIPT hemi-glutarate hydrochloride and previously known crystalline forms of 4-OH-DIPT hemi-glutarate hydrochloride. In some embodiments, the solid form of 4-OH-DIPT hemi-glutarate hydrochloride is a crystalline polymorph of 4-OH-DIPT hemi-glutarate, e.g., a crystalline polymorph of 4-OH-DIPT hemi-glutarate characterized by an XRPD profile substantially similar to that shown in FIG. 1 or FIG. 2.

In any embodiments, the at least one improved property of the solid form of 4-OH-DIPT hemi-glutarate hydrochloride may comprise a physical property, chemical property, pharmacokinetic property, or a combination thereof. In some embodiments, the at least one improved property comprises a melting point, glass transition temperature, flowability, thermal stability, shelf life, stability against polymorphic transition, hygroscopic properties, solubility in water and/or organic solvents, reactivity, compatibility with excipients and/or delivery vehicles, bioavailability, absorption, distribution, metabolism, excretion, toxicity including cytotoxicity, dissolution rate, half-life, or a combination thereof, that is improved compared to an amorphous sample of 4-OH-DIPT hemi-glutarate hydrochloride and/or a previously known crystalline form of 4-OH-DIPT hemi-glutarate hydrochloride.

In any embodiments, the solid form may be a crystalline solid, a hydrate, or a combination thereof. The crystalline solid may be substantially a single form, such as a polymorph form. And the polymorph may be selected to have one or more desired properties, particularly improved properties, such as physical properties, chemical properties, pharmacokinetic properties, or a combination thereof. The one or more desired properties may comprise melting point, glass transition temperature, flowability, thermal stability, mechanical stability, shelf life, stability against polymorphic transition, hygroscopic properties, solubility in water and/or organic solvents, reactivity, compatibility with excipients and/or delivery vehicles, bioavailability, absorption, distribution, metabolism, excretion, toxicity including cytotoxicity, dissolution rate, half-life, or a combination thereof.

Also disclosed herein are embodiments of a pharmaceutical composition, comprising a solid form of 4-OH-DIPT hemi-glutarate hydrochloride, and a pharmaceutically acceptable excipient.

A method for administering the solid form of 4-OH-DIPT hemi-glutarate hydrochloride also is disclosed herein. In some embodiments, the method comprises administering to a subject an effective amount of a solid form of 4-OH-DIPT hemi-glutarate hydrochloride, or a pharmaceutical composition thereof. In some embodiments, the subject is suffering from a neurological disease or a psychiatric disorder, or both, such as a neurodegenerative disorder. The neurological disorder or psychiatric disorder, or both, may comprise depression, addiction, anxiety, or a post-traumatic stress disorder, and/or the neurological disorder or psychiatric disorder, or both, may comprise treatment resistant depression, suicidal ideation, major depressive disorder, bipolar disorder, schizophrenia, or substance use disorder. In some embodiments, the neurological disorder or psychiatric disorder, or both, comprises stroke, traumatic brain injury, or a combination thereof.

The method may comprise further comprising administering an effective amount of an empathogenic agent and/or a 5-$HT_{2A}$ antagonist to the subject. The 5-$HT_{2A}$ antagonist may be selected from MDL-11,939, eplivanserin (SR-46, 349), ketanserin, ritanserin, altanserin, acepromazine, mianserin, mirtazapine, quetiapine, SB204741, SB206553, SB242084, LY272015, SB243213, blonanserin, SB200646, RS102221, nefazodone, MDL-100,907, pimavanserin, nelotanserin and lorcaserin.

In any embodiments, administering the solid form of the compound comprises oral, parenteral, or topical administration. In certain embodiments, oral administration is used, but in other particular embodiments, administration is by injection, inhalation, intraocular, intravaginal, intrarectal or transdermal routes.

The foregoing and other objects, features, and advantages of the invention will become more apparent from the following detailed description, which proceeds with reference to the accompanying figures.

Disclosed herein are novel solid forms of 4-OH-DIPT hemi-succinate hydrochloride. The solid form of 4-OH-DIPT hemi-succinate hydrochloride may have at least one improved property compared to amorphous 4-OH-DIPT hemi-succinate hydrochloride and to previously known crystalline forms of 4-OH-DIPT hemi-succinate hydrochloride.

Also disclosed herein is a solid form of 4-OH-DIPT hemi-succinate hydrochloride that is made by the method described in Example 1. The solid form of 4-OH-DIPT hemi-succinate hydrochloride made by the disclosed method may have at least one improved property compared to amorphous 4-OH-DIPT hemi-succinate hydrochloride and previously known crystalline forms of 4-OH-DIPT hemi-succinate hydrochloride.

In any embodiments, the at least one improved property of the solid form of 4-OH-DIPT hemi-succinate hydrochloride may comprise a physical property, chemical property, pharmacokinetic property, or a combination thereof. In some embodiments, the at least one improved property comprises a melting point, glass transition temperature, flowability, thermal stability, shelf life, stability against polymorphic transition, hygroscopic properties, solubility in water and/or organic solvents, reactivity, compatibility with excipients and/or delivery vehicles, bioavailability, absorption, distribution, metabolism, excretion, toxicity including cytotoxicity, dissolution rate, half-life, or a combination thereof, that is improved compared to an amorphous sample of 4-OH-DIPT hemi-succinate hydrochloride and/or a previously known crystalline form of 4-OH-DIPT hemi-succinate hydrochloride.

In any embodiments, the solid form may be a crystalline solid, a hydrate, or a combination thereof. The crystalline solid may be substantially a single form, such as a polymorph form. And the polymorph may be selected to have one or more desired properties, particularly improved properties, such as physical properties, chemical properties, pharmacokinetic properties, or a combination thereof. The one or more desired properties may comprise melting point, glass transition temperature, flowability, thermal stability, mechanical stability, shelf life, stability against polymorphic transition, hygroscopic properties, solubility in water and/or organic solvents, reactivity, compatibility with excipients and/or delivery vehicles, bioavailability, absorption, distribution, metabolism, excretion, toxicity including cytotoxicity, dissolution rate, half-life, or a combination thereof.

Also disclosed herein are embodiments of a pharmaceutical composition, comprising a solid form of 4-OH-DIPT hemi-succinate hydrochloride, and a pharmaceutically acceptable excipient.

A method for administering the solid form of 4-OH-DIPT hemi-succinate hydrochloride also is disclosed herein. In some embodiments, the method comprises administering to a subject an effective amount of a solid form of 4-OH-DIPT hemi-succinate hydrochloride, or a pharmaceutical composition thereof. In some embodiments, the subject is suffering from a neurological disease or a psychiatric disorder, or both, such as a neurodegenerative disorder. The neurological disorder or psychiatric disorder, or both, may comprise depression, addiction, anxiety, or a post-traumatic stress disorder, and/or the neurological disorder or psychiatric disorder, or both, may comprise treatment resistant depression, suicidal ideation, major depressive disorder, bipolar disorder, schizophrenia, or substance use disorder. In some embodiments, the neurological disorder or psychiatric disorder, or both, comprises stroke, traumatic brain injury, or a combination thereof.

The method may comprise further comprising administering an effective amount of an empathogenic agent and/or a 5-$HT_{2A}$ antagonist to the subject. The 5-$HT_{2A}$ antagonist may be selected from MDL-11,939, eplivanserin (SR-46,349), ketanserin, ritanserin, altanserin, acepromazine, mianserin, mirtazapine, quetiapine, SB204741, SB206553, SB242084, LY272015, SB243213, blonanserin, SB200646, RS102221, nefazodone, MDL-100,907, pimavanserin, nelotanserin and lorcaserin.

In any embodiments, administering the solid form of the compound comprises oral, parenteral, or topical administration. In certain embodiments, oral administration is used, but in other particular embodiments, administration is by injection, inhalation, intraocular, intravaginal, intrarectal or transdermal routes.

The foregoing and other objects, features, and advantages of the invention will become more apparent from the following detailed description.

DETAILED DESCRIPTION

Definitions

Figure 1:
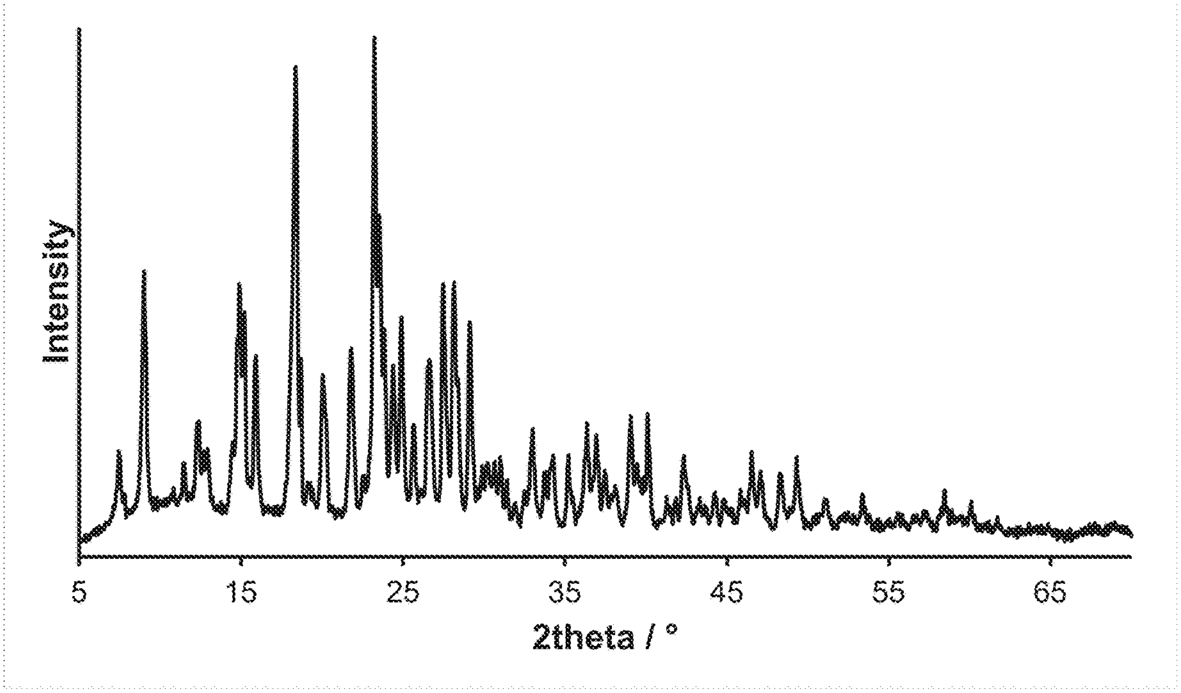
FIG. 1 is a plot of intensity versus 2θ, illustrating a stacked X-ray diffractogram plot of an exemplary solid form of 4-OH-DIPT hemi-glutarate hydrochloride, with the data normalized to 10,000 counts.

The following explanations of terms and methods are provided to better describe the present disclosure and to guide those of ordinary skill in the art in the practice of the present disclosure. The singular forms "a," "an," and "the" refer to one or more than one, unless the context clearly dictates otherwise. The term "or" refers to a single element of stated alternative elements or a combination of two or more elements, unless the context clearly indicates otherwise. As used herein, "comprises" means "includes." Thus, "comprising A or B," means "including A, B, or A and B," without excluding additional elements. All references, including patents and patent applications cited herein, are incorporated by reference in their entirety, unless otherwise specified.

Unless otherwise indicated, all numbers expressing quantities of components, molecular weights, percentages, temperatures, times, and so forth, as used in the specification or claims, are to be understood as being modified by the term "about." Accordingly, unless otherwise indicated, implicitly or explicitly, the numerical parameters set forth are approximations that may depend on the desired properties sought and/or limits of detection under standard test conditions/methods. When directly and explicitly distinguishing embodiments from discussed prior art, the embodiment numbers are not approximates unless the word "about" is expressly recited.

Unless explained otherwise, all technical and scientific terms used herein have the same meaning as commonly understood by one of ordinary skill in the art to which this disclosure pertains. Although methods and materials similar or equivalent to those described herein can be used in the practice or testing of the present disclosure, suitable methods and materials are described below. The materials, methods, and examples are illustrative only and not intended to be limiting.

"Administering" refers to any suitable mode of administration, including, oral administration, administration as a suppository, topical contact, parenteral, intravenous, intraperitoneal, intramuscular, intralesional, intranasal or subcutaneous administration, intrathecal administration, or the implantation of a slow-release device e.g., a mini-osmotic pump, to the subject.

"4-OH-DIPT hemi-glutarate" refers to the compound 5-((3-(2-(diisopropylamino)ethyl)-1H-indol-4-yl)oxy)-5-oxopentanoic acid. The compound also may be referred to as 4-hydroxy-N,N-diisopropyltryptamine hemi-glutarate.

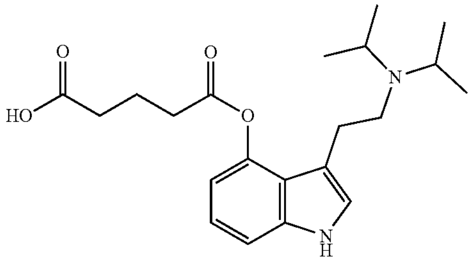

4-OH-DIPT hemi-glutarate

"4-OH-DIPT hemi-succinate" refers to the compound 4-((3-(2-(diisopropylamino)ethyl)-1H-indol-4-yl)oxy)-4-oxobutanoic acid. The compound also may be referred to as 4-hydroxy-N,N-diisopropyltryptamine hemi-succinate.

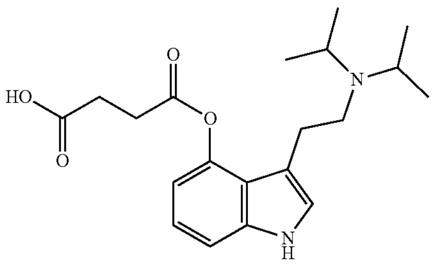

4-OH-DIPT hemi-succinate

"4-OH-DIPT hemi-glutarate hydrochloride" refers to the compound 5-((3-(2-(diisopropylamino)ethyl)-1H-indol-4-yl)oxy)-5-oxopentanoic acid hydrochloride. The compound also may be referred to as 4-hydroxy-N,N-diisopropyltryptamine hemi-glutarate hydrochloride.

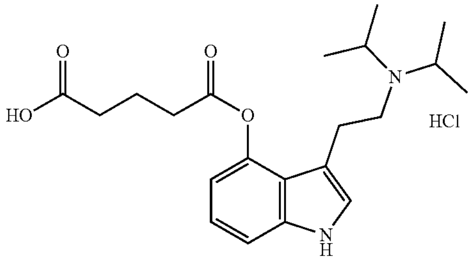

4-OH-DIPT hemi-glutarate hydrochloride

"4-OH-DIPT hemi-succinate hydrochloride" refers to the compound 4-((3-(2-(diisopropylamino)ethyl)-1H-indol-4-yl)oxy)-4-oxobutanoic acid hydrochloride. The compound also may be referred to as 4-hydroxy-N,N-diisopropyltryptamine hemi-succinate hydrochloride.

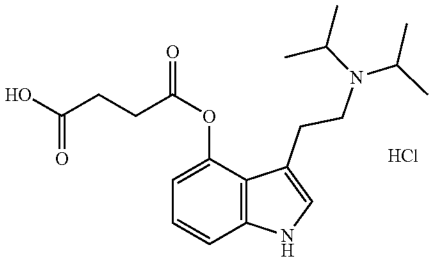

4-OH-DIPT hemi-succinate hydrochloride

"Subject" refers to an animal, such as a mammal, including, but not limited to, primates (e.g., humans), cows, sheep, goats, horses, dogs, cats, rabbits, rats, mice and the like. In certain embodiments, the subject is a human subject.

"Therapeutically effective amount" or "therapeutically sufficient amount" or "effective or sufficient amount" refers to a dose that produces therapeutic effects for which it is administered. The exact dose will depend on the purpose of the treatment, and will be ascertainable by one skilled in the art using known techniques (see, e.g., Lieberman, Pharmaceutical Dosage Forms (vols. 1-3, 1992); Lloyd, The Art, Science and Technology of Pharmaceutical Compounding (1999); Pickar, Dosage Calculations (1999); and Remington: The Science and Practice of Pharmacy, 20th Edition, 2003, Gennaro, Ed., Lippincott, Williams & Wilkins). In sensitized cells, the therapeutically effective dose can often be lower than the conventional therapeutically effective dose for non-sensitized cells.

"Neuronal plasticity" refers to the ability of the brain to change its structure and/or function continuously throughout a subject's life. Examples of the changes to the brain include, but are not limited to, the ability to adapt or respond to internal and/or external stimuli, such as due to an injury, and the ability to produce new neurites, dendritic spines, and synapses.

"Brain disorder" refers to a neurological disorder which affects the brain's structure and function. Brain disorders can include, but are not limited to, Alzheimer's, Parkinson's disease, psychological disorder, depression, treatment resistant depression, addiction, anxiety, post-traumatic stress disorder, suicidal ideation, major depressive disorder, bipolar disorder, schizophrenia, stroke, traumatic brain injury, and substance use disorder.

"Combination therapy" refers to a method of treating a disease or disorder, wherein two or more different pharmaceutical agents are administered in overlapping regimens so that the subject is simultaneously exposed to both agents. For example, the compounds of the invention can be used in combination with other pharmaceutically active compounds. The compounds of the invention can be administered simultaneously (as a single preparation or separate preparation) or sequentially to the other drug therapy. In general, a combination therapy envisions administration of two or more drugs during a single cycle or course of therapy.

"Neurotrophic factors" refers to a family of soluble peptides or proteins which support the survival, growth, and differentiation of developing and mature neurons.

"Modulate" or "modulating" or "modulation" refers to an increase or decrease in the amount, quality, or effect of a particular activity, function or molecule. By way of illustration and not limitation, agonists, partial agonists, antagonists, and allosteric modulators (e.g., a positive allosteric modulator) of a G protein-coupled receptor (e.g., $5HT_{2A}$) are modulators of the receptor.

"Agonism" refers to the activation of a receptor or enzyme by a modulator, or agonist, to produce a biological response.

"Agonist" refers to a modulator that binds to a receptor or enzyme and activates the receptor to produce a biological response. By way of example only, "$5HT_{2A}$ agonist" can be used to refer to a compound that exhibits an $EC_{50}$ with respect to $5HT_{2A}$ activity of no more than about 100 mM. In some embodiments, the term "agonist" includes full agonists or partial agonists. "Full agonist" refers to a modulator that binds to and activates a receptor with the maximum response that an agonist can elicit at the receptor. "Partial agonist" refers to a modulator that binds to and activates a given receptor, but has partial efficacy, that is, less than the maximal response, at the receptor relative to a full agonist.

"Positive allosteric modulator" refers to a modulator that binds to a site distinct from the orthosteric binding site and enhances or amplifies the effect of an agonist.

"Antagonism" refers to the inactivation of a receptor or enzyme by a modulator, or antagonist. Antagonism of a receptor, for example, is when a molecule binds to the receptor and does not allow activity to occur.

"Antagonist" or "neutral antagonist" refers to a modulator that binds to a receptor or enzyme and blocks a biological response. An antagonist has no activity in the absence of an agonist or inverse agonist but can block the activity of either, causing no change in the biological response.

"Composition" refers to a product comprising the specified ingredients in the specified amounts, as well as any product, which results, directly or indirectly, from combination of the specified ingredients in the specified amounts. By "pharmaceutically acceptable" it is meant the carrier, diluent or excipient must be compatible with the other ingredients of the formulation.

"Pharmaceutically acceptable excipient" refers to a substance that aids the administration of an active agent to and absorption by a subject. Pharmaceutical excipients useful in the present invention include, but are not limited to, binders, fillers, disintegrants, lubricants, coatings, sweeteners, flavors and colors. One of skill in the art will recognize that other pharmaceutical excipients are useful in the present invention.

Compounds

Disclosed herein are solid forms of 4-OH-DIPT hemi-glutarate that are useful to treat various disorders, such as brain disorders. Also disclosed are methods for making the solid forms of 4-OH-DIPT hemi-glutarate and method of administering the solid forms of 4-OH-DIPT hemi-glutarate.

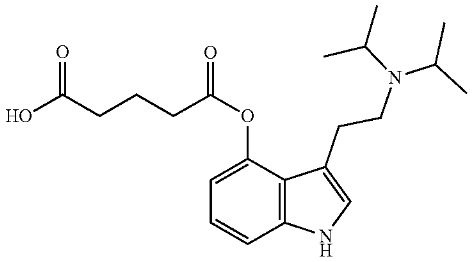

4-OH-DIPT hemi-glutarate

In some embodiments, the solid form of the compound is a crystalline form of 4-OH-DIPT hemi-glutarate. In some embodiments, the solid form of the compound is a salt of the compound. In some embodiments, the solid form of 4-OH-DIPT hemi-glutarate is a polymorph of 4-OH-DIPT hemi-glutarate, such as a polymorph of the free base (zwitterionic) compound or a polymorph of the salt. In some embodiments, the solid form of the compound is a crystalline salt form of the compound, such as an acid addition salt form.

Disclosed herein are solid forms of 4-OH-DIPT hemi-succinate that are useful to treat various disorders, such as brain disorders. Also disclosed are methods for making the solid forms of 4-OH-DIPT hemi-succinate and method of administering the solid forms of 4-OH-DIPT hemi-succinate.

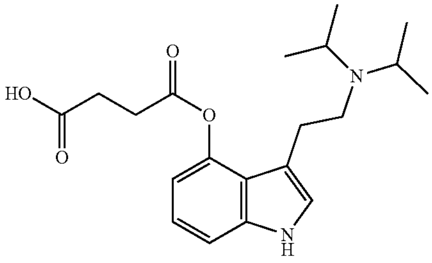

4-OH-DIPT hemi-succinate

In some embodiments, the solid form of the compound is a crystalline form of 4-OH-DIPT hemi-succinate. In some embodiments, the solid form of the compound is a salt of the compound. In some embodiments, the solid form of 4-OH-DIPT hemi-succinate is a polymorph of 4-OH-DIPT hemi-succinate, such as a polymorph of the free base (zwitterionic) compound or a polymorph of the salt. In some embodiments, the solid form of the compound is a crystalline salt form of the compound, such as an acid addition salt form.

Disclosed herein are solid forms of 4-OH-DIPT hemi-glutarate hydrochloride that are useful to treat various disorders, such as brain disorders. Also disclosed are methods for making the solid forms of 4-OH-DIPT hemi-glutarate hydrochloride and method of administering the solid forms of 4-OH-DIPT hemi-glutarate hydrochloride.

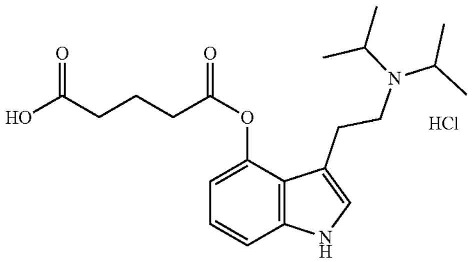

4-OH-DIPT hemi-glutarate hydrochloride

In some embodiments, the solid form of the compound is a crystalline form of 4-OH-DIPT hemi-glutarate hydrochloride. In some embodiments, the solid form of 4-OH-DIPT hemi-glutarate hydrochloride is a polymorph of 4-OH-DIPT hemi-glutarate hydrochloride, such as a novel polymorph that is not previously known in the art.

Disclosed herein are solid forms of 4-OH-DIPT hemi-succinate hydrochloride that are useful to treat various disorders, such as brain disorders. Also disclosed are methods for making the solid forms of 4-OH-DIPT hemi-succinate hydrochloride and method of administering the solid forms of 4-OH-DIPT hemi-succinate hydrochloride.

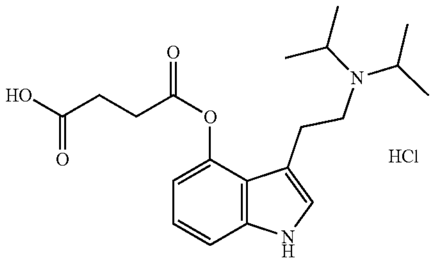

4-OH-DIPT hemi-succinate hydrochloride

In some embodiments, the solid form of the compound is a crystalline form of 4-OH-DIPT hemi-succinate hydrochloride. In some embodiments, the solid form of 4-OH-DIPT hemi-succinate hydrochloride is a polymorph of 4-OH-DIPT hemi-succinate hydrochloride, such as a novel polymorph that is not previously known in the art.

A) Salts

In some embodiments, the solid form of 4-OH-DIPT hemi-glutarate comprises a salt of 4-OH-DIPT hemi-glutarate. Suitable salts include a pharmaceutically acceptable salt of 4-OH-DIPT hemi-glutarate. In some embodiments, the salt is not a hydrochloride salt of 4-OH-DIPT hemi-glutarate. In some embodiments, the salt of 4-OH-DIPT hemi-glutarate may be formed from a suitable pharmaceutically acceptable acid, including, without limitation, inorganic acids such as hydrobromic acid, sulfuric acid, nitric acid, phosphoric acid, and the like, as well as organic acids such as formic acid, acetic acid, trifluoroacetic acid, propionic acid, glycolic acid, pyruvic acid, oxalic acid, maleic acid, malonic acid, succinic acid, tartaric acid, citric acid, benzoic acid, cinnamic acid, mandelic acid, benzene sulfonic acid, isethionic acid, methanesulfonic acid, ethanesulfonic acid, p-toluenesulfonic acid, salicylic acid, xinafoic acid, and the like.

In other embodiments, the salt of 4-OH-DIPT hemi-glutarate may be formed from a suitable pharmaceutically acceptable base, including, without limitation, inorganic bases such as sodium, potassium, lithium, ammonium, calcium, magnesium, iron, zinc, copper, manganese, aluminum salts and the like. Salts derived from pharmaceutically acceptable organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, tris(hydroxymethyl)aminomethane (Tris), ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Additional information concerning pharmaceutically acceptable salts can be found in, for example, S. M. Berge, et al., "Pharmaceutical Salts," *J. Pharm. Sci.,* 1977; 66:1-19 which is incorporated herein by reference.

In some embodiments, the solid form of 4-OH-DIPT hemi-succinate comprises a salt of 4-OH-DIPT hemi-succinate. Suitable salts include a pharmaceutically acceptable salt of 4-OH-DIPT hemi-succinate. In some embodiments, the salt is not a hydrochloride salt of 4-OH-DIPT hemi-succinate. In some embodiments, the salt of 4-OH-DIPT hemi-succinate may be formed from a suitable pharmaceutically acceptable acid, including, without limitation, inorganic acids such as hydrobromic acid, sulfuric acid, nitric acid, phosphoric acid, and the like, as well as organic acids such as formic acid, acetic acid, trifluoroacetic acid, propionic acid, glycolic acid, pyruvic acid, oxalic acid, maleic acid, malonic acid, succinic acid, tartaric acid, citric acid, benzoic acid, cinnamic acid, mandelic acid, benzene sulfonic acid, isethionic acid, methanesulfonic acid, ethanesulfonic acid, p-toluenesulfonic acid, salicylic acid, xinafoic acid, and the like.

In other embodiments, the salt of 4-OH-DIPT hemi-succinate may be formed from a suitable pharmaceutically acceptable base, including, without limitation, inorganic bases such as sodium, potassium, lithium, ammonium, calcium, magnesium, iron, zinc, copper, manganese, aluminum salts and the like. Salts derived from pharmaceutically acceptable organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, tris(hydroxymethyl)aminomethane (Tris), ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins, and the like. Additional information concerning pharmaceutically acceptable salts can be found in, for example, S. M. Berge, et al., "Pharmaceutical Salts," *J. Pharm. Sci.,* 1977; 66:1-19 which is incorporated herein by reference.

In some embodiments, the salt may be formed using an acid from Table 1.

TABLE 1

| | |
|---|---|
| naphthalene-1,5-disulfonic acid | citric acid |
| sulfuric acid | d-glucuronic acid |
| ethane-1,2-disulfonic acid | lactobionic acid |
| p-toluenesulfonic acid | D-glucoheptonic acid |
| thiocyanic acid | (−)-L-pyroglutamic acid |
| methanesulfonic acid | L-malic acid |
| dodecylsulfuric acid | hippuric acid |
| naphthalene-2-sulfonic acid | D-gluconic acid |
| benzenesulfonic acid | D,L-lactic acid |
| oxalic acid | oleic acid |
| glycerophosphoric acid | succinic acid |
| ethanesulfonic acid, 2-hydroxy | glutaric acid |
| L-aspartic acid | cinnamic acid |
| maleic acid | adipic acid |
| phosphoric acid | sebacic acid |
| ethanesulfonic acid | (+)-camphoric acid |
| glutamic acid | acetic acid |
| pamoic (embonic) acid | nicotinic acid |
| glutaric acid, 2-oxo- | isobutyric acid |
| 2-naphthoic acid, 1-hydroxy | propionic acid |
| malonic acid | lauric acid |
| gentisic acid | stearic acid |
| L-tartaric acid | orotic acid |
| galactaric (mucic) acid | carbonic acid |
| Xinafoic acid | Fumaric acid |
| Hydrobromic acid | |

The acid salts of 4-OH-DIPT hemi-glutarate disclosed herein can have any suitable stoichiometric ratio of acid to 4-OH-DIPT hemi-glutarate. In one embodiment, the molar ratio of acid to 4-OH-DIPT hemi-glutarate is from about 0.4 to about 2.2, such as forms wherein the salt has a stoichiometric ratio of acid to 4-OH-DIPT hemi-glutarate of from about 0.5 to about 2, such as about 0.5, about 1 or about 2.

The acid salts of 4-OH-DIPT hemi-succinate disclosed herein can have any suitable stoichiometric ratio of acid to 4-OH-DIPT hemi-succinate. In one embodiment, the molar ratio of acid to 4-OH-DIPT hemi-succinate is from about 0.4 to about 2.2, such as forms wherein the salt has a stoichiometric ratio of acid to 4-OH-DIPT hemi-succinate of from about 0.5 to about 2, such as about 0.5, about 1 or about 2.

B) Solid Forms

Embodiments of 4-OH-DIPT hemi-glutarate of the present disclosure are in a solid form. The solid form may be a crystalline form or an amorphous form. In some embodiments, the solid form is a crystalline form, such as a polymorph. In some embodiments, the solid form of 4-OH-DIPT hemi-glutarate is a salt. And in certain embodiments, the solid form is a crystalline salt form of the compound. A person of ordinary skill in the art understands that solid forms of 4-OH-DIPT hemi-glutarate such as crystalline forms including salt and non-salt crystalline forms of 4-OH-DIPT hemi-glutarate, may exist in more than one crystal form. Such different forms are referred to as polymorphs. In some embodiments, the disclosed compounds are particular polymorphs of 4-OH-DIPT hemi-glutarate or 4-OH-DIPT hemi-glutarate salts.

In some embodiments, the solid form of 4-OH-DIPT hemi-glutarate disclosed herein is selected to be a crystalline form, such as a particular polymorph of a crystalline form of 4-OH-DIPT hemi-glutarate that provides one or more desired properties. In one embodiment, the crystalline form offers advantages over the amorphous form of the molecule. In another embodiment, the disclosed polymorph offers improved properties as compared to another polymorph of 4-OH-DIPT hemi-glutarate. The 4-OH-DIPT hemi-glutarate may be a salt or free base (zwitterionic) compound. The one or more desired properties may include, but are not limited to, physical properties, including but not limited to, melting point, glass transition temperature, flowability, and/or stability, such as thermal stability, mechanical stability, shelf life, stability against polymorphic transition, etc.; chemical properties, such as, but not limited to, hygroscopic properties, solubility in water and/or organic solvents, reactivity, compatibility with excipients and/or delivery vehicles; and/or pharmacokinetic properties, such as, but not limited to, bioavailability, absorption, distribution, metabolism, excretion, toxicity including cytotoxicity, dissolution rate, and/or half-life.

Embodiments of 4-OH-DIPT hemi-succinate of the present disclosure are in a solid form. The solid form may be a crystalline form or an amorphous form. In some embodiments, the solid form is a crystalline form, such as a polymorph. In some embodiments, the solid form of 4-OH-DIPT hemi-succinate is a salt. And in certain embodiments, the solid form is a crystalline salt form of the compound. A person of ordinary skill in the art understands that solid forms of 4-OH-DIPT hemi-succinate such as crystalline forms including salt and non-salt crystalline forms of 4-OH-DIPT hemi-succinate, may exist in more than one crystal form. Such different forms are referred to as polymorphs. In some embodiments, the disclosed compounds are particular polymorphs of 4-OH-DIPT hemi-succinate or 4-OH-DIPT hemi-succinate salts.

In some embodiments, the solid form of 4-OH-DIPT hemi-succinate disclosed herein is selected to be a crystalline form, such as a particular polymorph of a crystalline form of 4-OH-DIPT hemi-succinate that provides one or more desired properties. In one embodiment, the crystalline form offers advantages over the amorphous form of the molecule. In another embodiment, the disclosed polymorph offers improved properties as compared to another polymorph of 4-OH-DIPT hemi-succinate. The 4-OH-DIPT hemi-succinate may be a salt or free base (zwitterionic) compound. The one or more desired properties may include, but are not limited to, physical properties, including but not limited to, melting point, glass transition temperature, flowability, and/or stability, such as thermal stability, mechanical stability, shelf life, stability against polymorphic transition, etc.; chemical properties, such as, but not limited to, hygroscopic properties, solubility in water and/or organic solvents, reactivity, compatibility with excipients and/or delivery vehicles; and/or pharmacokinetic properties, such as, but not limited to, bioavailability, absorption, distribution, metabolism, excretion, toxicity including cytotoxicity, dissolution rate, and/or half-life.

Embodiments of 4-OH-DIPT hemi-glutarate hydrochloride of the present disclosure are in a solid form. The solid form may be a crystalline form or an amorphous form. In some embodiments, the solid form is a crystalline form, such as a polymorph. In some embodiments, the solid form of 4-OH-DIPT hemi-glutarate hydrochloride is a crystalline form of the compound. A person of ordinary skill in the art understands that solid forms of 4-OH-DIPT hemi-glutarate hydrochloride may exist in more than one crystal form. Such different forms are referred to as polymorphs. In some embodiments, the disclosed compounds are particular polymorphs of 4-OH-DIPT hemi-glutarate hydrochloride.

In some embodiments, the present disclosure provides solid forms of 4-OH-DIPT hemi-glutarate hydrochloride, e.g., crystalline forms of 4-OH-DIPT hemi-glutarate hydrochloride. In some embodiments, the 4-OH-DIPT hemi-glutarate hydrochloride XRPD profile is substantially similar to that shown in FIG. 1 or 2.

In some embodiments, the solid form of 4-OH-DIPT hemi-glutarate hydrochloride is characterized by an XRPD signal at 18.4°2θ (±0.2°2θ; ±0.1°2θ; or ±0.0°2θ; Cu Kα1 radiation).

In some embodiments, the solid form of 4-OH-DIPT hemi-glutarate hydrochloride is characterized by XRPD signals at 18.4°2θ and 23.3°2θ (±0.2°2θ; ±0.1°2θ; or ±0.0°2θ; Cu Kα1 radiation).

In some embodiments, the solid form of 4-OH-DIPT hemi-glutarate hydrochloride is characterized by two or more, or three XRPD signals selected from the group consisting of 18.4°2θ, 23.3°2θ, and 24.9°2θ (±0.2°2θ; ±0.1°2θ; or ±0.0°2θ; Cu Kα1 radiation). In some embodiments, the solid form of 4-OH-DIPT hemi-glutarate hydrochloride is characterized by XRPD signals at 18.4°2θ, 23.3°2θ, and 24.9°2θ (±0.2°2θ; ±0.1°2θ; or ±0.0°2θ; Cu Kα1 radiation).

In some embodiments, the solid form of 4-OH-DIPT hemi-glutarate hydrochloride is characterized by two or more, or three or more XRPD signals selected from the group consisting of 18.4°2θ, 23.3°2θ, 24.9°2θ, and 24.3°2θ (±0.2°2θ; ±0.1°2θ; or ±0.0°2θ; Cu Kα1 radiation). In some embodiments, the solid form of 4-OH-DIPT hemi-glutarate hydrochloride is characterized by XRPD signals at 18.4°2θ, 23.3°2θ, 24.9°2θ, and 24.3°2θ (±0.2°2θ; ±0.1°2θ; or ±0.0°2θ; Cu Kα1 radiation).

In some embodiments, the solid form of 4-OH-DIPT hemi-glutarate hydrochloride is characterized by two or more, or three or more XRPD signals selected from the group consisting of 18.4°2θ, 23.3°2θ, 24.9°2θ, 24.3°2θ, and 15.9°2θ (±0.2°2θ; ±0.1°2θ; or ±0.0°2θ; Cu Kα1 radiation). In some embodiments, the solid form of 4-OH-DIPT hemi-glutarate hydrochloride is characterized by XRPD signals at 18.4°2θ, 23.3°2θ, 24.9°2θ, 24.3°2θ, and 15.9°2θ (±0.2°2θ; ±0.1°2θ; or ±0.0°2θ; Cu Kα1 radiation).

In some embodiments, the solid form of 4-OH-DIPT hemi-glutarate hydrochloride is characterized by two or more, or three or more XRPD signals selected from the group consisting of 18.4°2θ, 23.3°2θ, 24.9°2θ, 24.3°2θ, 15.9°2θ, and 20.0°2θ (±0.2°2θ; ±0.1°2θ; or ±0.0°2θ; Cu Kα1 radiation). In some embodiments, the solid form of 4-OH-DIPT hemi-glutarate hydrochloride is characterized by XRPD signals at 18.4°2θ, 23.3°2θ, 24.9°2θ, 24.3°2θ, 15.9°2θ, and 20.0°2θ (±0.2°2θ; ±0.1°2θ; or ±0.0°2θ; Cu Kα1 radiation).

In some embodiments, the solid form of 4-OH-DIPT hemi-glutarate hydrochloride is characterized by two or more, or three or more XRPD signals selected from the group consisting of 18.4°2θ, 23.3°2θ, 24.9°2θ, 24.3°2θ, 15.9°2θ, 20.0°2θ, and 26.6°2θ (±0.2°2θ; ±0.1°2θ; or ±0.0°2θ; Cu Kα1 radiation). In some embodiments, the solid form of 4-OH-DIPT hemi-glutarate hydrochloride is characterized by XRPD signals at 18.4°2θ, 23.3°2θ, 24.9°2θ, 24.3°2θ, 15.9°2θ, 20.0°2θ, and 26.6°2θ (±0.2°2θ; ±0.1°20; or ±0.0°2θ; Cu Kα1 radiation).

In some embodiments, the solid form of 4-OH-DIPT hemi-glutarate hydrochloride is characterized by two or more, or three or more XRPD signals selected from the group consisting of 18.4°2θ, 23.3°2θ, 24.9°2θ, 24.3°2θ, 15.9°2θ, 20.0°2θ, 26.6°2θ, and 15.0°2θ (±0.2°2θ; ±0.1°2θ; or ±0.0°2θ; Cu Kα1 radiation). In some embodiments, the solid form of 4-OH-DIPT hemi-glutarate hydrochloride is characterized by XRPD signals at 18.4°2θ, 23.3°2θ, 24.9°2θ, 24.3°2θ, 15.9°2θ, 20.0°2θ, 26.6°2θ, and 15.0°2θ (±0.2°2θ; ±0.1°2θ; or ±0.0°2θ; Cu Kα1 radiation).

In some embodiments, the solid form of 4-OH-DIPT hemi-glutarate hydrochloride is characterized by two or more, or three or more XRPD signals selected from the group consisting of 18.4°2θ, 23.3°2θ, 24.9°2θ, 24.3°2θ, 15.9°2θ, 20.0°2θ, 26.6°2θ, 15.0°2θ, and 28.3°2θ (±0.2°2θ; ±0.1°2θ; or ±0.0°2θ; Cu Kα1 radiation). In some embodiments, the solid form of 4-OH-DIPT hemi-glutarate hydrochloride is characterized by XRPD signals at 18.4°2θ, 23.3°2θ, 24.9°2θ, 24.3°2θ, 15.9°2θ, 20.0°2θ, 26.6°2θ, 15.0°2θ, and 28.3°2θ (±0.2°2θ; ±0.1°2θ; or ±0.0°2θ; Cu Kα1 radiation).

In some embodiments, the solid form of 4-OH-DIPT hemi-glutarate hydrochloride is characterized by two or more, or three or more XRPD signals selected from the group consisting of 18.4°2θ, 23.3°2θ, 24.9°2θ, 24.3°2θ, 15.9°2θ, 20.0°2θ, 26.6°2θ, 15.0°2θ, 28.3°2θ, and 21.8°2θ (±0.2°2θ; ±0.1°2θ; or ±0.0°2θ; Cu Kα1 radiation). In some embodiments, the solid form of 4-OH-DIPT hemi-glutarate hydrochloride is characterized by XRPD signals at 18.4°2θ, 23.3°2θ, 24.9°2θ, 24.3°2θ, 15.9°2θ, 20.0°2θ, 26.6°2θ, 15.0°2θ, 28.3°2θ, and 21.8°2θ (±0.2°2θ; ±0.1°2θ; or ±0.0°2θ; Cu Kα1 radiation).

In some embodiments, the crystalline 4-OH-DIPT hemi-glutarate hydrochloride is characterized by one, two, three, four, five, six, seven, eight, nine, ten, eleven, twelve, thirteen, fourteen, fifteen, sixteen, seventeen, eighteen, or nineteen XRPD signals selected from those set forth in Table 1A.

TABLE 1A

XRPD Signal Listing for 4-OH-DIPT hemi-glutarate hydrochloride

| Signal No. | Pos. [°2θ] | d-spacing [Å] | Rel. Int. [%] |
|---|---|---|---|
| 1 | 7.4 | 11.9 | 10.4 |
| 2 | 9.0 | 9.8 | 15.4 |
| 3 | 12.4 | 7.2 | 19.4 |
| 4 | 12.9 | 6.8 | 13.3 |
| 5 | 15.0 | 5.9 | 24.0 |
| 6 | 15.9 | 5.6 | 33.4 |
| 7 | 18.4 | 4.8 | 100.0 |
| 8 | 19.2 | 4.6 | 14.2 |
| 9 | 20.0 | 4.4 | 27.6 |
| 10 | 21.8 | 4.1 | 20.7 |
| 11 | 23.3 | 3.8 | 66.4 |
| 12 | 24.3 | 3.7 | 33.6 |
| 13 | 24.9 | 3.6 | 34.9 |
| 14 | 26.6 | 3.4 | 25.8 |
| 15 | 28.3 | 3.2 | 23.1 |
| 16 | 29.2 | 3.1 | 19.9 |
| 17 | 33.0 | 2.7 | 10.1 |
| 18 | 34.2 | 2.6 | 10.2 |
| 19 | 36.3 | 2.5 | 10.8 |

In some embodiments, the solid form of 4-OH-DIPT hemi-glutarate hydrochloride disclosed herein is selected to be a crystalline form, such as a particular polymorph of a crystalline form of 4-OH-DIPT hemi-glutarate hydrochloride that provides one or more desired properties. In one embodiment, the crystalline form offers advantages over the amorphous form of the molecule. In another embodiment, the disclosed polymorph offers improved properties as compared to another polymorph of 4-OH-DIPT hemi-glutarate hydrochloride. The one or more desired properties may include, but are not limited to, physical properties, including but not limited to, melting point, glass transition temperature, flowability, and/or stability, such as thermal stability, mechanical stability, shelf life, stability against polymorphic transition, etc.; chemical properties, such as, but not limited to, hygroscopic properties, solubility in water and/or organic solvents, reactivity, compatibility with excipients and/or delivery vehicles; and/or pharmacokinetic properties, such as, but not limited to, bioavailability, absorption, distribution, metabolism, excretion, toxicity including cytotoxicity, dissolution rate, and/or half-life.

Embodiments of 4-OH-DIPT hemi-succinate hydrochloride of the present disclosure are in a solid form. The solid form may be a crystalline form or an amorphous form. In some embodiments, the solid form is a crystalline form, such as a polymorph. In some embodiments, the solid form of 4-OH-DIPT hemi-succinate hydrochloride is a crystalline form of the compound. A person of ordinary skill in the art understands that solid forms of 4-OH-DIPT hemi-succinate hydrochloride may exist in more than one crystal form. Such different forms are referred to as polymorphs. In some embodiments, the disclosed compounds are particular polymorphs of 4-OH-DIPT hemi-succinate hydrochloride.

In some embodiments, the solid form of 4-OH-DIPT hemi-succinate hydrochloride disclosed herein is selected to be a crystalline form, such as a particular polymorph of a crystalline form of 4-OH-DIPT hemi-succinate hydrochloride that provides one or more desired properties. In one embodiment, the crystalline form offers advantages over the amorphous form of the molecule. In another embodiment, the disclosed polymorph offers improved properties as compared to another polymorph of 4-OH-DIPT hemi-succinate hydrochloride. The one or more desired properties may include, but are not limited to, physical properties, including but not limited to, melting point, glass transition temperature, flowability, and/or stability, such as thermal stability, mechanical stability, shelf life, stability against polymorphic transition, etc.; chemical properties, such as, but not limited to, hygroscopic properties, solubility in water and/or organic solvents, reactivity, compatibility with excipients and/or delivery vehicles; and/or pharmacokinetic properties, such as, but not limited to, bioavailability, absorption, distribution, metabolism, excretion, toxicity including cytotoxicity, dissolution rate, and/or half-life.

The desired polymorph may be produced by techniques known to persons of ordinary skill in the art. Such techniques include, but are not limited to, crystallization in particular solvents and/or at particular temperatures, supersaturation, using a precipitation agent, such as a salt, glycol, alcohol, etc., co-crystallization, lyophilization, spray drying, freeze drying, and/or complexing with an inert agent.

Techniques to identify a particular solid form of 4-OH-DIPT hemi-glutarate are known to persons of ordinary skill in the art, and include, but are not limited to, X-ray crystallography, X-ray diffraction, electron crystallography, powder diffraction, including X-ray, neutron, or electron diffraction, X-ray fiber diffraction, small-angle X-ray scattering, and/or melting point.

Techniques to identify a particular solid form of 4-OH-DIPT hemi-succinate are known to persons of ordinary skill in the art, and include, but are not limited to, X-ray crystallography, X-ray diffraction, electron crystallography, powder diffraction, including X-ray, neutron, or electron diffraction, X-ray fiber diffraction, small-angle X-ray scattering, and/or melting point.

Techniques to identify a particular solid form of 4-OH-DIPT hemi-glutarate hydrochloride are known to persons of ordinary skill in the art, and include, but are not limited to, X-ray crystallography, X-ray diffraction, electron crystallography, powder diffraction, including X-ray, neutron, or electron diffraction, X-ray fiber diffraction, small-angle X-ray scattering, and/or melting point.

Techniques to identify a particular solid form of 4-OH-DIPT hemi-succinate hydrochloride are known to persons of ordinary skill in the art, and include, but are not limited to, X-ray crystallography, X-ray diffraction, electron crystallography, powder diffraction, including X-ray, neutron, or electron diffraction, X-ray fiber diffraction, small-angle X-ray scattering, and/or melting point.

Pharmaceutical Compositions and Formulations

In some embodiments, the present disclosure provides a pharmaceutical composition comprising one or more of the solid forms of 4-OH-DIPT hemi-glutarate, illustrated above, and a pharmaceutically acceptable excipient. Such compositions are suitable for administration to a subject, such as a human subject.

In some embodiments, the present disclosure provides a pharmaceutical composition comprising one or more of the solid forms of 4-OH-DIPT hemi-succinate, illustrated above, and a pharmaceutically acceptable excipient. Such compositions are suitable for administration to a subject, such as a human subject.

In some embodiments, the present disclosure provides a pharmaceutical composition comprising one or more of the solid forms of 4-OH-DIPT hemi-succinate hydrochloride, illustrated above, and a pharmaceutically acceptable excipient. Such compositions are suitable for administration to a subject, such as a human subject.

In some embodiments, the present disclosure provides a pharmaceutical composition comprising one or more of the solid forms of 4-OH-DIPT hemi-glutarate hydrochloride, illustrated above, and a pharmaceutically acceptable excipient. Such compositions are suitable for administration to a subject, such as a human subject.

The presently disclosed pharmaceutical compositions can be prepared in a wide variety of oral, parenteral and topical dosage forms. Oral preparations include tablets, pills, powder, capsules, lozenges, cachets, slurries, suspensions, etc., suitable for ingestion by the patient. The compositions of the present disclosure can also be administered by injection, that is, intravenously, intramuscularly, intracutaneously, subcutaneously, intraduodenally, or intraperitoneally. Also, the compositions described herein can be administered by inhalation, for example, intranasally. Additionally, the compositions of the present disclosure can be administered transdermally. The compositions of this disclosure can also be administered by intraocular, intravaginal, and intrarectal routes including suppositories, insufflation, powders and aerosol formulations (for examples of steroid inhalants, see Rohatagi, *J. Clin. Pharmacol.* 35:1187-1193, 1995; Tjwa, *Ann. Allergy Asthma Immunol.* 75:107-111, 1995). Accordingly, the present disclosure also provides pharmaceutical compositions including a pharmaceutically acceptable carrier or excipient and the solid form of 4-OH-DIPT hemi-glutarate of the present disclosure. Accordingly, the present disclosure also provides pharmaceutical compositions including a pharmaceutically acceptable carrier or excipient and the solid form of 4-OH-DIPT hemi-succinate of the present disclosure. Accordingly, the present disclosure also provides pharmaceutical compositions including a pharmaceutically acceptable carrier or excipient and the solid form of 4-OH-DIPT hemi-succinate hydrochloride of the present disclosure. Accordingly, the present disclosure also provides pharmaceutical compositions including a pharmaceutically acceptable carrier or excipient and the solid form of 4-OH-DIPT hemi-glutarate hydrochloride of the present disclosure.

For preparing pharmaceutical compositions from the compounds disclosed herein, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Mack Publishing Co, Easton PA ("Remington's").

In powders, the carrier is a finely divided solid, which is in a mixture with the finely divided active component. In tablets, the active component is mixed with the carrier having the necessary binding properties in suitable proportions and compacted in the shape and size desired. The powders and tablets preferably contain from 5% to 70% or 10% to 70% of the compounds of the present disclosure.

Suitable solid excipients include, but are not limited to, magnesium carbonate; magnesium stearate; talc; pectin; dextrin; starch; tragacanth; a low melting wax; cocoa butter; carbohydrates; sugars including, but not limited to, lactose, sucrose, mannitol, or sorbitol, starch from corn, wheat, rice, potato, or other plants; cellulose such as methyl cellulose, hydroxypropylmethyl-cellulose, or sodium carboxymethylcellulose; and gums including arabic and tragacanth; as well as proteins including, but not limited to, gelatin and collagen.

If desired, disintegrating or solubilizing agents may be added, such as the cross-linked polyvinyl pyrrolidone, agar, alginic acid, or a salt thereof, such as sodium alginate.

For preparing suppositories, a low melting wax, such as a mixture of fatty acid glycerides or cocoa butter, is first melted and the compounds of the present disclosure are dispersed homogeneously therein, as by stirring. The molten homogeneous mixture is then poured into convenient sized molds, allowed to cool, and thereby to solidify.

Liquid form preparations include suspensions, for example, water or water/propylene glycol suspensions.

Aqueous suspensions suitable for oral use can be made by dispersing the finely divided active component in water with viscous material, such as natural or synthetic gums, resins, methylcellulose, sodium carboxymethylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan mono-oleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Also included are solid form preparations, which are intended to be converted, shortly before use, to liquid form preparations for oral administration. Such liquid forms include suspensions. These preparations may contain, in addition to the active component, colorants, flavors, stabilizers, buffers, artificial and natural sweeteners, dispersants, thickeners, solubilizing agents, and the like.

Oil suspensions can be formulated by suspending the compound of the present invention in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The compositions of the present disclosure can also be delivered as microspheres for slow release in the body. For example, microspheres can be formulated for administration via intradermal injection of drug-containing microspheres, which slowly release subcutaneously (see Rao, *J. Biomater Sci. Polym. Ed.* 7:623-645, 1995; as biodegradable and injectable gel formulations (see, e.g., Gao *Pharm. Res.* 12:857-863, 1995); or, as microspheres for oral administration (see, e.g., Eyles, *J. Pharm. Pharmacol.* 49:669-674, 1997). Both transdermal and intradermal routes afford constant delivery for weeks or months.

In some embodiments, the pharmaceutical compositions of the present disclosure can be formulated for parenteral administration, such as intravenous (IV) administration or administration into a body cavity or lumen of an organ. The formulations for administration will commonly comprise a solution or suspension of the compositions of the present disclosure dissolved or suspended in a pharmaceutically acceptable carrier. Among the acceptable vehicles and solvents that can be employed are water and Ringer's solution, an isotonic sodium chloride. In addition, sterile fixed oils can conventionally be employed as a solvent or suspending medium. For this purpose, any bland fixed oil can be employed including synthetic mono- or diglycerides. In addition, fatty acids such as oleic acid can likewise be used in the preparation of injectables. These solutions or suspensions are sterile and generally free of undesirable matter. These formulations may be sterilized by conventional, well known sterilization techniques. The formulations may contain pharmaceutically acceptable auxiliary substances as required to approximate physiological conditions such as pFI adjusting and buffering agents, toxicity adjusting agents, e.g., sodium acetate, sodium chloride, potassium chloride, calcium chloride, sodium lactate and the like. The concentration of the compositions of the present disclosure in these formulations can vary widely, and will be selected primarily based on fluid volumes, viscosities, body weight, and the like, in accordance with the particular mode of administration selected and the patient's needs. For IV administration, the formulation can be a sterile injectable preparation, such as a sterile injectable aqueous or oleaginous suspension. This suspension can be formulated according to the known art using those suitable dispersing or wetting agents and suspending agents. The sterile injectable preparation can also be a sterile injectable solution or suspension in a nontoxic parenterally-acceptable diluent or solvent, such as a solution of 1,3-butanediol.

In some embodiments, the formulations of the compositions of the present disclosure can be delivered by the use of liposomes which fuse with the cellular membrane or are endocytosed, for example, by employing ligands attached to the liposome, or attached directly to the oligonucleotide, that bind to surface membrane protein receptors of the cell resulting in endocytosis. By using liposomes, particularly where the liposome surface carries ligands specific for target cells, or are otherwise preferentially directed to a specific organ, one can focus the delivery of the compositions of the present invention into the target cells in vivo. (See, e.g., Al-Muhammed, *J. Microencapsul.* 13:293-306, 1996; Chonn, *Curr. Opin. Biotechnol.* 6:698-708, 1995; Ostro, *Am. J. Hosp. Pharm.* 46:1576-1587, 1989).

Administration

The compositions of the present disclosure can be administered by any suitable means, including oral, parenteral and topical methods. Transdermal administration methods, by a topical route, can be formulated as applicator sticks, suspensions, creams, ointments, pastes, jellies, paints, powders, and aerosols.

The pharmaceutical preparation is preferably in unit dosage form. In such form the preparation is subdivided into unit doses containing appropriate quantities of the compounds of the present invention. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The compound of the present invention can be present in any suitable amount, and can depend on various factors including, but not limited to, weight and age of the subject, state of the disease, and the like as is known to those of ordinary skill in the art. Suitable dosage ranges for the compounds disclosed herein include from about 0.1 mg to about 10,000 mg, or about 1 mg to about 1000 mg, or about 10 mg to about 750 mg, or about 25 mg to about 500 mg, or about 50 mg to about 250 mg. Suitable dosages for the compound of the present invention include about 1 mg, 5, 10, 20, 30, 40, 50, 60, 70, 80, 90, 100, 200, 300, 400, 500, 600, 700, 800, 900 or 1000 mg.

The compounds disclosed herein can be administered at any suitable frequency, interval and duration. For example, the compounds can be administered once an hour, or two, three or more times an hour, once a day, or two, three, or more times per day, or once every 2, 3, 4, 5, 6, or 7 days, so as to provide the preferred dosage level. When the compound of the present invention is administered more than once a day, representative intervals include 5, 10, 15, 20, 30, 45 and 60 minutes, as well as 1, 2, 4, 6, 8, 10, 12, 16, 20, and 24 hours. The compound of the present invention can be administered once, twice, or three or more times, for an hour, for 1 to 6 hours, for 1 to 12 hours, for 1 to 24 hours, for 6 to 12 hours, for 12 to 24 hours, for a single day, for 1 to 7 days, for a single week, for 1 to 4 weeks, for a month, for 1 to 12 months, for a year or more, or even indefinitely.

The composition can also contain other compatible therapeutic agents. The compounds described herein can be used in combination with one another, with other active agents known to be useful in modulating a glucocorticoid receptor, or with adjunctive agents that may not be effective alone, but may contribute to the efficacy of the active agent.

The compounds of the present disclosure can be co-administered with a second active agent. Co-administration includes administering the compound of the present disclosure and active agent within 0.5, 1, 2, 4, 6, 8, 10, 12, 16, 20, or 24 hours of each other. Co-administration also includes administering the compound of the present disclosure and active agent simultaneously, approximately simultaneously (e.g., within about 1, 5, 10, 15, 20, or 30 minutes of each other), or sequentially in any order. Moreover, the compound of the present disclosure and the active agent can each be administered once a day, or two, three, or more times per day so as to provide the preferred dosage level per day.

In some embodiments, co-administration can be accomplished by co-formulation, such as by preparing a single pharmaceutical composition including both the compound of the present disclosure and a second active agent. In other embodiments, the compound of the present disclosure and the second active agent can be formulated separately.

The disclosed compounds and the second active agent can be present in the compositions of the present disclosure in any suitable weight ratio, such as from about 1:100 to about 100:1 (w/w), or about 1:50 to about 50:1, or about 1:25 to about 25:1, or about 1:10 to about 10:1, or about 1:5 to about 5:1 (w/w). The compound of the present disclosure and the second active agent can be present in any suitable weight ratio, such as about 1:100 (w/w), 1:50, 1:25, 1:10, 1:5, 1:4, 1:3, 1:2, 1:1, 2:1, 3:1, 4:1, 5:1, 10:1, 25:1, 50:1 or 100:1 (w/w). Other dosages and dosage ratios of the compound of the present disclosure and the active agent are suitable in the compositions and methods disclosed herein.

Methods of Treatment

The solid forms of 4-OH-DIPT hemi-glutarate of the present disclosure can be used for increasing neuronal plasticity. The compounds of the present disclosure can also be used to treat any brain disease. The compounds of the present disclosure can also be used for increasing at least one of translation, transcription or secretion of neurotrophic factors.

The solid forms of 4-OH-DIPT hemi-succinate of the present disclosure can be used for increasing neuronal plasticity. The compounds of the present disclosure can also be used to treat any brain disease. The compounds of the present disclosure can also be used for increasing at least one of translation, transcription or secretion of neurotrophic factors.

The solid forms of 4-OH-DIPT hemi-succinate hydrochloride of the present disclosure can be used for increasing neuronal plasticity. The compounds of the present disclosure can also be used to treat any brain disease. The compounds of the present disclosure can also be used for increasing at least one of translation, transcription or secretion of neurotrophic factors.

The solid forms of 4-OH-DIPT hemi-glutarate hydrochloride of the present disclosure can be used for increasing neuronal plasticity. The compounds of the present disclosure can also be used to treat any brain disease. The compounds of the present disclosure can also be used for increasing at least one of translation, transcription or secretion of neurotrophic factors.

In some embodiments, a compound of the present disclosure is used to treat neurological diseases. In some embodiments, the compounds have, for example, anti-addictive properties, antidepressant properties, anxiolytic properties, or a combination thereof. In some embodiments, the neurological disease is a neuropsychiatric disease. In some embodiments, the neuropsychiatric disease is a mood or anxiety disorder. In some embodiments, the neurological disease is a migraine, headaches (e.g., cluster headache), post-traumatic stress disorder (PTSD), anxiety, depression, neurodegenerative disorder, Alzheimer's disease, Parkinson's disease, psychological disorder, treatment resistant depression, suicidal ideation, major depressive disorder, bipolar disorder, schizophrenia, stroke, traumatic brain injury, and addiction (e.g., substance use disorder). In some embodiments, the neurological disease is a migraine or cluster headache. In some embodiments, the neurological disease is a neurodegenerative disorder, Alzheimer's disease, or Parkinson's disease. In some embodiments, the neurological disease is a psychological disorder, treatment resistant depression, suicidal ideation, major depressive disorder, bipolar disorder, schizophrenia, post-traumatic stress disorder (PTSD), addiction (e.g., substance use disorder), depression, or anxiety. In some embodiments, the neuropsychiatric disease is a psychological disorder, treatment resistant depression, suicidal ideation, major depressive disorder, bipolar disorder, schizophrenia, post-traumatic stress disorder (PTSD), addiction (e.g., substance use disorder), depression, or anxiety. In some embodiments, the neuropsychiatric disease or neurological disease is post-traumatic stress disorder (PTSD), addiction (e.g., substance use disorder), schizophrenia, depression, or anxiety. In some embodiments, the neuropsychiatric disease or neurological disease is addiction (e.g., substance use disorder). In some embodiments, the neuropsychiatric disease or neurological disease is depression. In some embodiments, the neuropsychiatric disease or neurological disease is anxiety. In some embodiments, the neuropsychiatric disease or neurological disease is post-traumatic stress disorder (PTSD). In some embodiments, the neurological disease is stroke or traumatic brain injury. In some embodiments, the neuropsychiatric disease or neurological disease is schizophrenia.

In some embodiments, a compound of the present disclosure is used for increasing neuronal plasticity. In some embodiments, the compounds described herein are used for treating a brain disorder. In some embodiments, the compounds described herein are used for increasing at least one of translation, transcription, or secretion of neurotrophic factors.

In some embodiments, the present disclosure provides a method of treating a disease, including administering to a subject in need thereof, a therapeutically effective amount of a compound of the present disclosure. In some embodiments, the disease is a musculoskeletal pain disorder including fibromyalgia, muscle pain, joint stiffness, osteoarthritis, rheumatoid arthritis, muscle cramps. In some embodiments, the present invention provides a method of treating a disease of women's reproductive health including premenstrual dysphoric disorder (PMDD), premenstrual syndrome (PMS), post-partum depression, and menopause.

In some embodiments, the 4-OH-DIPT hemi-glutarate of the present disclosure have activity as 5-$HT_{2A}$ modulators. In some embodiments, the 4-OH-DIPT hemi-succinate of the present disclosure have activity as 5-$HT_{2A}$ modulators. In some embodiments, the 4-OH-DIPT hemi-glutarate hydrochloride of the present disclosure have activity as 5-$HT_{2A}$ modulators. In some embodiments, the 4-OH-DIPT hemi-succinate hydrochloride of the present disclosure have activity as 5-$HT_{2A}$ modulators.

In some embodiments, the compounds of the present disclosure elicit a biological response by activating the 5-$HT_{2A}$ receptor (e.g., allosteric modulation or modulation of a biological target that activates the 5-$HT_{2A}$ receptor). 5-$HT_{2A}$ agonism has been correlated with the promotion of neural plasticity (Ly et al., 2018). 5-$HT_{2A}$ antagonists abrogate the neuritogenesis and spinogenesis effects of hallucinogenic compounds with 5-$HT_{2A}$ agonist activity, for example, DMT, LSD and DOI. In some embodiments, the compounds of the present disclosure are 5-$HT_{2A}$ modulators and promote neural plasticity (e.g., cortical structural plasticity). In some embodiments, the compounds of the present disclosure are selective 5-$HT_{2A}$ modulators and promote neural plasticity (e.g., cortical structural plasticity). In some embodiments, promotion of neural plasticity includes, for example, increased dendritic spine growth, increased synthesis of synaptic proteins, strengthened synaptic responses, increased dendritic arbor complexity, increased dendritic branch content, increased spinogenesis, increased neuritogenesis, or any combination thereof. In some embodiments, increased neural plasticity includes, for example, increased cortical structural plasticity in the anterior parts of the brain.

In some embodiments, the 5-$HT_{2A}$ modulators (e.g., 5-$HT_{2A}$ agonists) are non-hallucinogenic. In some embodiments, non-hallucinogenic 5-$HT_{2A}$ modulators (e.g., 5-$HT_{2A}$ agonists) are used to treat neurological diseases, which modulators do not elicit dissociative side-effects. In some embodiments, the hallucinogenic potential of the compounds described herein is assessed in vitro. In some embodiments, the hallucinogenic potential assessed in vitro of the compounds described herein is compared to the hallucinogenic potential assessed in vitro of hallucinogenic homologs. In some embodiments, the compounds described herein elicit less hallucinogenic potential in vitro than the hallucinogenic homologs.

In some embodiments, serotonin receptor modulators, such as modulators of serotonin receptor 2A (5-$HT_{2A}$ modulators, e.g., 5-$HT_{2A}$ agonists), are used to treat a brain disorder. The presently disclosed compounds can function as 5-$HT_{2A}$ agonists alone, or in combination with a second therapeutic agent that also is a 5-$HT_{2A}$ modulator. In such cases the second therapeutic agent can be an agonist or an antagonist. In some instances, it may be helpful administer a 5-$HT_{2A}$ antagonist in combination with a compound of the present disclosure to mitigate undesirable effects of 5-$HT_{2A}$ agonism, such as potential hallucinogenic effects. Serotonin receptor modulators useful as second therapeutic agents for combination therapy as described herein are known to those of skill in the art and include, without limitation, ketanserin, volinanserin (MDL-100907), eplivanserin (SR-46349), pimavanserin (ACP-103), glemanserin (MDL-11939), ritanserin, flibanserin, nelotanserin, blonanserin, mianserin, mirtazapine, roluperiodone (CYR-101, MIN-101), quetiapine, olanzapine, altanserin, acepromazine, nefazodone, risperidone, pruvanserin, AC-90179, AC-279, adatanserin, fananserin, HY10275, benanserin, butanserin, manserin, iferanserin, lidanserin, pelanserin, seganserin, tropanserin, lorcaserin, ICI-169369, methysergide, trazodone, cinitapride, cyproheptadine, brexpiprazole, cariprazine, agomelatine, setoperone, 1-(1-Naphthyl) piperazine, LY-367265, pirenperone, metergoline, deramciclane, amperozide, cinanserin, LY-86057, GSK-215083, cyamemazine, mesulergine, BF-1, LY-215840, sergolexole, spiramide, LY-53857, amesergide, LY-108742, pipamperone, LY-314228, 5-1-R91150, 5-MeO-NBpBrT, 9-Aminomethyl-9,10-dihydroanthracene, niaprazine, SB-215505, SB-204741, SB-206553, SB-242084, LY-272015, SB-243213, SB-200646, RS-102221, zotepine, clozapine, chlorpromazine, sertindole, iloperidone, paliperidone, asenapine, amisulpride, aripiprazole, lurasidone, ziprasidone, lumateperone, perospirone, mosapramine, AMDA (9-Aminomethyl-9,10-dihydroanthracene), methiothepin, xanomeline, buspirone, an extended-release form of olanzapine (e.g., ZYPREXA RELPREVV), an extended-release form of quetiapine, an extended-release form of risperidone (e.g., Risperdal Consta), an extended-release form of paliperidone (e.g., Invega Sustenna and Invega Trinza), an extended-release form of fluphenazine decanoate including Prolixin Decanoate, an extended-release form of aripiprazole lauroxil including Aristada, an extended-release form of aripiprazole including Abilify Maintena, 3-(2-(4-(4-Fluorobenzoyl) piperazin-1-yl)ethyl)-5-methyl-5-phenylimidazolidine-2,4-dione, 3-(2-(4-Benzhydrylpiperazin-1-yl) ethyl)-5-methyl-5-phenylimidazolidine-2,4-dione, 3-(3-(4-(2-Fluorophenyl) piperazin-1-yl) propyl)-5-methyl-5-phenylimidazolidine-2,4-dione, 3-(3-(4-(3-Fluorophenyl) piperazin-1-yl) propyl)-5-methyl-5-phenylimidazolidine-2,4-dione, 3-(3-(4-(4-Fluorophenyl) piperazin-1-yl) propyl)-5-methyl-5-phenylimidazolidine-2,4-dione, 3-(3-(4-(4-Fluorobenzoyl) piperazin-1-yl) propyl)-5-methyl-5-phenylimidazolidine-2,4-dione, 3-(2-(4-(4-Fluorobenzoyl) piperazin-1-yl)ethyl)-8-phenyl-1,3-diazaspiro[4.5]decane-2,4-dione, 3-(2-(4-Benzhydrylpiperazin-1-yl)ethyl)-8-phenyl-1,3-diazaspiro[4.5]decane-2,4-dione, 3-(3-(4-(2-Fluorophenyl) piperazin-1-yl) propyl)-8-phenyl-1,3-diazaspiro [4.5]decane-2,4-dione, 3-(3-(4-(3-Fluorophenyl) piperazin-1-yl) propyl)-8-phenyl-1,3-diazaspiro[4.5]decane-2,4-dione, 3-(3-(4-(4-Fluorophenyl) piperazin-1-yl) propyl)-8-phenyl-1,3-diazaspiro[4.5]decane-2,4-dione, and 3-(3-(4-(4-

Fluorobenzoyl) piperazin-1-yl) propyl)-8-phenyl-1,3-diazaspiro[4.5]decane-2,4-dione, or a pharmaceutically acceptable salt, solvate, metabolite, deuterated analogue, derivative, prodrug, or combinations thereof. In some embodiments, the serotonin receptor modulator used as a second therapeutic is pimavanserin or a pharmaceutically acceptable salt, solvate, metabolite, derivative, or prodrug thereof. In some embodiments, the serotonin receptor modulator is administered prior to a compound disclosed herein, such as about three or about one hours prior to administration of a compound disclosed herein. In some embodiments, the serotonin receptor modulator is administered at most about one hour prior to the presently disclosed compound. Thus, in some embodiments of combination therapy with the presently disclosed compounds, the second therapeutic agent is a serotonin receptor modulator. In some embodiments the second therapeutic agent serotonin receptor modulator is provided at a dose of from about 10 mg to about 350 mg. In some embodiments, the serotonin receptor modulator is provided at a dose of from about 20 mg to about 200 mg. In some embodiments, the serotonin receptor modulator is provided at a dose of from about 10 mg to about 100 mg. In certain such embodiments, the compound of the present disclosure is provided at a dose of from about 10 mg to about 100 mg, or from about 20 mg to about 200 mg, or from about 15 mg to about 300 mg, and the serotonin receptor modulator is provided at a dose of about 10 mg to about 100 mg.

In some embodiments, non-hallucinogenic 5-$HT_{2A}$ modulators (e.g., 5-$HT_{2A}$ agonists) are used to treat neurological diseases. In some embodiments, the neurological diseases comprise decreased neural plasticity, decreased cortical structural plasticity, decreased 5-$HT_{2A}$ receptor content, decreased dendritic arbor complexity, loss of dendritic spines, decreased dendritic branch content, decreased spinogenesis, decreased neuritogenesis, retraction of neurites, or any combination thereof.

In some embodiments, non-hallucinogenic 5-$HT_{2A}$ modulators (e.g., 5-$HT_{2A}$ agonists) are used for increasing neuronal plasticity. In some embodiments, non-hallucinogenic 5-$HT_{2A}$ modulators (e.g., 5-$HT_{2A}$ agonists) are used for treating a brain disorder. In some embodiments, non-hallucinogenic 5-$HT_{2A}$ modulators (e.g., 5-$FIT_{2A}$ agonists) are used for increasing at least one of translation, transcription, or secretion of neurotrophic factors.

In some embodiments the presently disclosed compounds are given to patients in a low dose that is lower than would produce noticeable psychedelic effects but high enough to provide a therapeutic benefit. This dose range is predicted to be between 200 μg (micrograms) and 2 mg.

A) Methods for Increasing Neuronal Plasticity

Neuronal plasticity refers to the ability of the brain to change structure and/or function throughout a subject's life. New neurons can be produced and integrated into the central nervous system throughout the subject's life. Increasing neuronal plasticity includes, but is not limited to, promoting neuronal growth, promoting neuritogenesis, promoting synaptogenesis, promoting dendritogenesis, increasing dendritic arbor complexity, increasing dendritic spine density, and increasing excitatory synapsis in the brain. In some embodiments, increasing neuronal plasticity comprises promoting neuronal growth, promoting neuritogenesis, promoting synaptogenesis, promoting dendritogenesis, increasing dendritic arbor complexity, and increasing dendritic spine density.

In some embodiments, increasing neuronal plasticity by treating a subject with one or more of the disclosed compound can treat neurodegenerative disorder, Alzheimer's, Parkinson's disease, psychological disorder, depression, addiction, anxiety, post-traumatic stress disorder, treatment resistant depression, suicidal ideation, major depressive disorder, bipolar disorder, schizophrenia, stroke, traumatic brain injury, or substance use disorder.

In some embodiments, the present disclosure provides methods for increasing neuronal plasticity, comprising contacting a neuronal cell with a compound of the present disclosure. In some embodiments, increasing neuronal plasticity improves a brain disorder described herein.

In some embodiments, a compound of the present disclosure is used to increase neuronal plasticity. In some embodiments, the compounds used to increase neuronal plasticity have, for example, anti-addictive properties, antidepressant properties, anxiolytic properties, or a combination thereof. In some embodiments, decreased neuronal plasticity is associated with a neuropsychiatric disease. In some embodiments, the neuropsychiatric disease is a mood or anxiety disorder. In some embodiments, the neuropsychiatric disease includes, for example, migraine, cluster headache, post-traumatic stress disorder (PTSD), schizophrenia, anxiety, depression, and addiction (e.g., substance abuse disorder). In some embodiments, brain disorders include, for example, migraines, addiction (e.g., substance use disorder), depression, and anxiety.

In some embodiments, the experiment or assay to determine increased neuronal plasticity of any compound of the present disclosure is a phenotypic assay, a dendritogenesis assay, a spinogenesis assay, a synaptogenesis assay, a Sholl analysis, a concentration-response experiment, a 5-$HT_{2A}$ agonist assay, a 5-$HT_{2A}$ antagonist assay, a 5-$HT_{2A}$ binding assay, or a 5-$HT_{2A}$ blocking experiment (e.g., ketanserin blocking experiments). In some embodiments, the experiment or assay to determine the hallucinogenic potential of any compound of the present invention is a mouse head-twitch response (HTR) assay.

In some embodiments, the present disclosure provides a method for increasing neuronal plasticity, comprising contacting a neuronal cell with a compound disclosed herein.

B) Methods of Treating a Brain Disorder

In some embodiments, the present disclosure provides a method of treating a disease, including administering to a subject in need thereof, a therapeutically effective amount of 4-OH-DIPT hemi-glutarate of the present disclosure.

In some embodiments, the present disclosure provides a method of treating a disease, including administering to a subject in need thereof, a therapeutically effective amount of 4-OH-DIPT hemi-succinate of the present disclosure.

In some embodiments, the present disclosure provides a method of treating a disease, including administering to a subject in need thereof, a therapeutically effective amount of 4-OH-DIPT hemi-glutarate hydrochloride of the present disclosure.

In some embodiments, the present disclosure provides a method of treating a disease, including administering to a subject in need thereof, a therapeutically effective amount of 4-OH-DIPT hemi-succinate hydrochloride of the present disclosure.

In some embodiments, the disease is a musculoskeletal pain disorder including fibromyalgia, muscle pain, joint stiffness, osteoarthritis, rheumatoid arthritis, muscle cramps. In some embodiments, the present disclosure provides a method of treating a disease of women's reproductive health including premenstrual dysphoric disorder (PMDD), premenstrual syndrome (PMS), post-partum depression, and menopause. In some embodiments, the present disclosure provides a method of treating a brain disorder, including administering to a subject in need thereof, a therapeutically effective amount of a compound of the present disclosure. In some embodiments, the present disclosure provides a method of treating a brain disorder with combination therapy, including administering to a subject in need thereof, a therapeutically effective amount of a compound of the present disclosure and at least one additional therapeutic agent.

In some embodiments, 5-$HT_{2A}$ modulators (e.g., 5-$HT_{2A}$ agonists) are used to treat a brain disorder. In some embodiments, the brain disorders comprise decreased neural plasticity, decreased cortical structural plasticity, decreased 5-$HT_{2A}$ receptor content, decreased dendritic arbor complexity, loss of dendritic spines, decreased dendritic branch content, decreased spinogenesis, decreased neuritogenesis, retraction of neurites, or any combination thereof.

In some embodiments, a compound of the present disclosure is used to treat brain disorders. In some embodiments, the compounds have, for example, anti-addictive properties, antidepressant properties, anxiolytic properties, or a combination thereof. In some embodiments, the brain disorder is a neuropsychiatric disease. In some embodiments, the neuropsychiatric disease is a mood or anxiety disorder. In some embodiments, brain disorders include, for example, migraine, cluster headache, post-traumatic stress disorder (PTSD), anxiety, depression, panic disorder, suicidality, schizophrenia, and addiction (e.g., substance abuse disorder). In some embodiments, brain disorders include, for example, migraines, addiction (e.g., substance use disorder), depression, and anxiety.

In some embodiments, the present disclosure provides a method of treating a brain disorder, comprising administering to a subject in need thereof a therapeutically effective amount of a compound disclosed herein.

In some embodiments, the brain disorder is a neurodegenerative disorder, Alzheimer's, Parkinson's disease, psychological disorder, depression, addiction, anxiety, post-traumatic stress disorder, treatment resistant depression, suicidal ideation, major depressive disorder, bipolar disorder, schizophrenia, stroke, traumatic brain injury, or substance use disorder.

In some embodiments, the brain disorder is a neurodegenerative disorder, Alzheimer's, or Parkinson's disease. In some embodiments, the brain disorder is a psychological disorder, depression, addiction, anxiety, or a post-traumatic stress disorder. In some embodiments, the brain disorder is depression. In some embodiments, the brain disorder is addiction. In some embodiments, the brain disorder is treatment resistant depression, suicidal ideation, major depressive disorder, bipolar disorder, schizophrenia, stroke, traumatic brain injury, substance use disorder and/or anxiety. In some embodiments, the brain disorder is treatment resistant depression, suicidal ideation, major depressive disorder, bipolar disorder, schizophrenia, or substance use disorder. In some embodiments, the brain disorder is stroke or traumatic brain injury. In some embodiments, the brain disorder is treatment resistant depression, suicidal ideation, major depressive disorder, bipolar disorder, or substance use disorder. In some embodiments, the brain disorder comprises treatment resistant depression, suicidal ideation, major depressive disorder, bipolar disorder, schizophrenia, stroke, traumatic brain injury, substance use disorder and/or anxiety. In some embodiments, the brain disorder is treatment resistant depression, suicidal ideation, major depressive disorder, bipolar disorder, schizophrenia, or substance use disorder. In some embodiments, the brain disorder is stroke or traumatic brain injury. In some embodiments, the brain disorder is treatment resistant depression, suicidal ideation, major depressive disorder, bipolar disorder, or substance use disorder. In some embodiments, the brain disorder is schizophrenia. In some embodiments, the brain disorder is alcohol use disorder.

In some embodiments, the methods described herein are for treating a disease or disorder that is a neurological disease. For example, a compound provided herein can exhibit anti-addictive properties, antidepressant properties, anxiolytic properties, or a combination thereof. In some embodiments, the neurological disease is a neuropsychiatric disease. In some embodiments, the neuropsychiatric disease is a mood or anxiety disorder. In some embodiments, the neurological disease is selected from migraine, headaches (e.g., cluster headache), post-traumatic stress disorder (PTSD), anxiety, depression, neurodegenerative disorder, Alzheimer's disease, Parkinson's disease, psychological disorder, treatment resistant depression, suicidal ideation, major depressive disorder, bipolar disorder, schizophrenia, stroke, hypoxic brain injury, chronic traumatic encephalopathy (CTE), traumatic brain injury, dementia, and addiction (e.g., substance use disorder). In some embodiments, the neurological disease is a migraine or cluster headache. In some embodiments, the neurological disease is a neurodegenerative disorder, dementia, Alzheimer's disease, or Parkinson's disease. In some embodiments, the neurological disease is dementia. In some embodiments, the neurological disease is a psychological disorder, treatment resistant depression, suicidal ideation, major depressive disorder, bipolar disorder, schizophrenia, post-traumatic stress disorder (PTSD), addiction (e.g., substance use disorder), depression, or anxiety.

In some embodiments, the neuropsychiatric disease is a psychological disorder, treatment resistant depression, suicidal ideation, major depressive disorder, bipolar disorder, schizophrenia, post-traumatic stress disorder (PTSD), addiction (e.g., substance use disorder), depression, or anxiety. In some embodiments, the neuropsychiatric disease or neurological disease is post-traumatic stress disorder (PTSD), addiction (e.g., substance use disorder), schizophrenia, depression, or anxiety. In some embodiments, the neuropsychiatric disease or neurological disease is addiction (e.g., substance use disorder). In some embodiments, the neuropsychiatric disease or neurological disease is depression. In some embodiments, the neuropsychiatric disease or neurological disease is anxiety. In some embodiments, the neuropsychiatric disease or neurological disease is post-traumatic stress disorder (PTSD). In some embodiments, the neurological disease is stroke or traumatic brain injury. In some embodiments, the neuropsychiatric disease or neurological disease is schizophrenia.

In some embodiments, the method further comprises administering one or more additional therapeutic agent that is lithium, olanzapine (Zyprexa), quetiapine (Seroquel), risperidone (Risperdal), ariprazole (Abilify), ziprasidone (Geodon), clozapine (Clozaril), divalproex sodium (Depakote), lamotrigine (Lamictal), valproic acid (Depakene), carbamazepine (Equetro), topiramate (Topamax), levomilnacipran (Fetzima), duloxetine (Cymbalta, Yentreve), venlafaxine (Effexor), citalopram (Celexa), fluvoxamine (Luvox), escitalopram (Lexapro), fluoxetine (Prozac), paroxetine (Paxil), sertraline (Zoloft), clomipramine (Anafranil), amitriptyline (Elavil), desipramine (Norpramin), imipramine (Tofranil), nortriptyline (Pamelor), phenelzine (Nardil), tranylcypromine (Parnate), diazepam (Valium), alprazolam (Xanax), or clonazepam (Klonopin).

In certain embodiments of the method for treating a brain disorder with a solid form disclosed herein, a second therapeutic agent that is an empathogenic agent is administered. Examples of suitable empathogenic agents for use in combination with the present solid forms include phenethylamines, such as 3,4-methylene-dioxymethamphetamine (MDMA), and analogs thereof. Other suitable empathogenic agents for use in combination with the presently disclosed compounds include, without limitation, N-Allyl-3,4-methylenedioxy-amphetamine (MDAL)
N-Butyl-3,4-methylenedioxyamphetamine (MDBU)
N-Benzyl-3,4-methylenedioxyamphetamine (MDBZ)
N-Cyclopropylmethyl-3,4-methylenedioxyamphetamine (MDCPM)
N,N-Dimethyl-3,4-methylenedioxyamphetamine (MDDM)
N-Ethyl-3,4-methylenedioxyamphetamine (MDE; MDEA)
N-(2-Hydroxyethyl)-3,4-methylenedioxy amphetamine (MDHOET)
N-Isopropyl-3,4-methylenedioxyamphetamine (MDIP)
N-Methyl-3,4-ethylenedioxyamphetamine (MDMC)
N-Methoxy-3,4-methylenedioxyamphetamine (MDMEO)
N-(2-Methoxyethyl)-3,4-methylenedioxyamphetamine (MDMEOET)
alpha, alpha, N-Trimethyl-3,4-methylenedioxyphenethylamine (MDMP;
3,4-Methylenedioxy-N-methylphentermine)
N-Hydroxy-3,4-methylenedioxyamphetamine (MDOH)
3,4-Methylenedioxyphenethylamine (MDPEA)
alpha, alpha-Dimethyl-3,4-methylenedioxyphenethylamine (MDPH; 3,4-methylenedioxyphentermine)
N-Propargyl-3,4-methylenedioxyamphetamine (MDPL)
Methylenedioxy-2-aminoindane (MDAI)
1,3-Benzodioxolyl-N-methylbutanamine (MBDB)
3,4-methylenedioxy-N-methyl-α-ethylphenylethylamine
3,4-Methylenedioxyamphetamine (MDA)
Methylone (also known as "3,4-methylenedioxy-N-methylcathinone)
Ethylone, also known as 3,4-methylenedioxy-N-ethylcathinone
GHB or Gamma Hydroxybutyrate or sodium oxybate
N-Propyl-3,4-methylenedioxyamphetamine (MDPR), and the like.

In some embodiments, the compounds of the present disclosure are used in combination with the standard of care therapy for a neurological disease described herein. Non-limiting examples of the standard of care therapies, may include, for example, lithium, olanzapine, quetiapine, risperidone, ariprazole, ziprasidone, clozapine, divalproex sodium, lamotrigine, valproic acid, carbamazepine, topiramate, levomilnacipran, duloxetine, venlafaxine, citalopram, fluvoxamine, escitalopram, fluoxetine, paroxetine, sertraline, clomipramine, amitriptyline, desipramine, imipramine, nortriptyline, phenelzine, tranylcypromine, diazepam, alprazolam, clonazepam, or any combination thereof. Nonlimiting examples of standard of care therapy for depression are sertraline, fluoxetine, escitalopram, venlafaxine, or aripiprazole. Non-limiting examples of standard of care therapy for depression are citralopram, escitalopram, fluoxetine, paroxetine, diazepam, or sertraline. Additional examples of standard of care therapeutics are known to those of ordinary skill in the art.

C) Methods of Increasing at Least One of Translation, Transcription, or Secretion of Neurotrophic Factors Neurotrophic factors refers to a family of soluble peptides or proteins which support the survival, growth, and differentiation of developing and mature neurons. Increasing at least one of translation, transcription, or secretion of neurotrophic factors can be useful for, but not limited to, increasing neuronal plasticity, promoting neuronal growth, promoting neuritogenesis, promoting synaptogenesis, promoting dendritogenesis, increasing dendritic arbor complexity, increasing dendritic spine density, and increasing excitatory synapsis in the brain. In some embodiments, increasing at least one of translation, transcription, or secretion of neurotrophic factors can increasing neuronal plasticity. In some embodiments, increasing at least one of translation, transcription, or secretion of neurotrophic factors can promoting neuronal growth, promoting neuritogenesis, promoting synaptogenesis, promoting dendritogenesis, increasing dendritic arbor complexity, and/or increasing dendritic spine density.

In some embodiments, 5-$HT_{2A}$ modulators (e.g., 5-$HT_{2A}$ agonists) are used to increase at least one of translation, transcription, or secretion of neurotrophic factors. In some embodiments, a compound of the present disclosure is used to increase at least one of translation, transcription, or secretion of neurotrophic factors. In some embodiments, increasing at least one of translation, transcription or secretion of neurotrophic factors treats a migraine, headaches (e.g., cluster headache), post-traumatic stress disorder (PTSD), anxiety, depression, neurodegenerative disorder, Alzheimer's disease, Parkinson's disease, psychological disorder, treatment resistant depression, suicidal ideation, major depressive disorder, bipolar disorder, schizophrenia, stroke, traumatic brain injury, and addiction (e.g., substance use disorder).

In some embodiments, the experiment or assay used to determine increase translation of neurotrophic factors includes ELISA, western blot, immunofluorescence assays, proteomic experiments, and mass spectrometry. In some embodiments, the experiment or assay used to determine increase transcription of neurotrophic factors includes gene expression assays, PCR, and microarrays. In some embodiments, the experiment or assay used to determine increase secretion of neurotrophic factors includes ELISA, western blot, immunofluorescence assays, proteomic experiments, and mass spectrometry.

In some embodiments, the present disclosure provides a method for increasing at least one of translation, transcription or secretion of neurotrophic factors, comprising contacting a neuronal cell with a compound disclosed herein.

Combination Therapy

In some embodiments, the solid forms of 4-OH-DIPT hemi-glutarate hydrochloride disclosed herein function as serotonin receptor modulators, such as modulators of serotonin receptor 2A (5-$HT_{2A}$ modulators, e.g., 5-$HT_{2A}$ agonists), are used to treat a brain disorder. The presently disclosed solid forms can function as 5-$HT_{2A}$ agonists alone, or in combination with a second therapeutic agent that also is a 5-$HT_{2A}$ modulator. In such cases the second therapeutic agent can be an agonist or an antagonist. In some instances, it may be helpful administer a 5-$HT_{2A}$ antagonist in combination with a solid form of the present disclosure to mitigate undesirable effects of 5-$HT_{2A}$ agonism, such as potential hallucinogenic effects. Serotonin receptor modulators useful as second therapeutic agents for combination therapy as described herein are known to those of skill in the art and include, without limitation, ketanserin, volinanserin (MDL-100907), eplivanserin (SR-46349), pimavanserin (ACP-103), glemanserin (MDL-11939), ritanserin, flibanserin, nelotanserin, blonanserin, mianserin, mirtazapine, roluperiodone (CYR-101, MIN-101), quetiapine, olanzapine, altanserin, acepromazine, nefazodone, risperidone, pruvanserin, AC-90179, AC-279, adatanserin, fananserin, HY10275, benanserin, butanserin, manserin, iferanserin, lidanserin, pelanserin, seganserin, tropanserin, lorcaserin, ICI-169369, methysergide, trazodone, cinitapride, cyproheptadine, brexpiprazole, cariprazine, agomelatine, setoperone, 1-(1-Naphthyl) piperazine, LY-367265, pirenperone, metergoline, deramciclane, amperozide, cinanserin, LY-86057, GSK-215083, cyamemazine, mesulergine, BF-1, LY-215840, sergolexole, spiramide, LY-53857, amesergide, LY-108742, pipamperone, LY-314228, 5-1-R91150, 5-MeO-NBpBrT, 9-Aminomethyl-9,10-dihydroanthracene, niaprazine, SB-215505, SB-204741, SB-206553, SB-242084, LY-272015, SB-243213, SB-200646, RS-102221, zotepine, clozapine, chlorpromazine, sertindole, iloperidone, paliperidone, asenapine, amisulpride, aripiprazole, lurasidone, ziprasidone, lumateperone, perospirone, mosapramine, AMDA (9-Aminomethyl-9,10-dihydroanthracene), methiothepin, xanomeline, buspirone, an extended-release form of olanzapine (e.g., ZYPREXA RELPREVV), an extended-release form of quetiapine, an extended-release form of risperidone (e.g., Risperdal Consta), an extended-release form of paliperidone (e.g., Invega Sustenna and Invega Trinza), an extended-release form of fluphenazine decanoate including Prolixin Decanoate, an extended-release form of aripiprazole lauroxil including Aristada, an extended-release form of aripiprazole including Abilify Maintena, 3-(2-(4-(4-Fluorobenzoyl) piperazin-1-yl)ethyl)-5-methyl-5-phenylimidazolidine-2,4-dione, 3-(2-(4-Benzhydrylpiperazin-1-yl) ethyl)-5-methyl-5-phenylimidazolidine-2,4-dione, 3-(3-(4-(2-Fluorophenyl) piperazin-1-yl) propyl)-5-methyl-5-phenylimidazolidine-2,4-dione, 3-(3-(4-(3-Fluorophenyl) piperazin-1-yl) propyl)-5-methyl-5-phenylimidazolidine-2,4-dione, 3-(3-(4-(4-Fluorophenyl) piperazin-1-yl) propyl)-5-methyl-5-phenylimidazolidine-2,4-dione, 3-(3-(4-(4-Fluorobenzoyl) piperazin-1-yl) propyl)-5-methyl-5-phenylimidazolidine-2,4-dione, 3-(2-(4-(4-Fluorobenzoyl) piperazin-1-yl)ethyl)-8-phenyl-1,3-diazaspiro[4.5]decane-2,4-dione, 3-(2-(4-Benzhydrylpiperazin-1-yl)ethyl)-8-phenyl-1,3-diazaspiro[4.5]decane-2,4-dione, 3-(3-(4-(2-Fluorophenyl) piperazin-1-yl) propyl)-8-phenyl-1,3-diazaspiro [4.5]decane-2,4-dione, 3-(3-(4-(3-Fluorophenyl) piperazin-1-yl) propyl)-8-phenyl-1,3-diazaspiro[4.5]decane-2,4-dione, 3-(3-(4-(4-Fluorophenyl) piperazin-1-yl) propyl)-8-phenyl-1,3-diazaspiro[4.5]decane-2,4-dione, and 3-(3-(4-(4-Fluorobenzoyl) piperazin-1-yl) propyl)-8-phenyl-1,3-diazaspiro[4.5]decane-2,4-dione, or a pharmaceutically acceptable salt, solvate, metabolite, deuterated analogue, derivative, prodrug, or combinations thereof.

In some embodiments, the serotonin receptor modulator comprises glemanserin (MDL-11,939), eplivanserin (SR-46, 349), ketanserin, ritanserin, altanserin, acepromazine, mianserin, mirtazapine, quetiapine, SB204741, SB206553, SB242084, LY272015, SB243213, blonanserin, SB200646, RS102221, nefazodone, volinanserin (MDL-100,907), pimavanserin (ACO-103), pruvanserin, nelotanserin, lorcaserin, flibanserin, roluperiodone or a pharmaceutically acceptable salt, solvate, metabolite, deuterated analog, derivative, prodrug, or combinations thereof.

In certain embodiments the serotonin receptor modulator is selected from the group consisting of altanserin, blonanserin, eplivanserin, glemanserin, volinanserin, ketanserin, ritanserin, pimavanserin, nelotanserin, pruvanserin, and flibanserin. In one embodiment, the serotonin receptor modulator is selected from the group consisting of eplivanserin, volinanserin, ketanserin, ritanserin, pimavanserin, nelotanserin, pruvanserin, flibanserin, olanzapine, quetiapine, and risperidone.

In some embodiments, the serotonin receptor modulator is ketanserin or a pharmaceutically acceptable salt, solvate, metabolite, deuterated analog, derivative, or prodrug thereof. In some embodiments, the serotonin receptor modulator is pimavanserin or a pharmaceutically acceptable salt, solvate, metabolite, deuterated analog, derivative, or prodrug thereof. In some embodiments, the serotonin receptor modulator is eplivanserin or a pharmaceutically acceptable salt, solvate, metabolite, deuterated analog, derivative, or prodrug thereof. In some embodiments, the serotonin receptor modulator is flibanserin or a pharmaceutically acceptable salt, solvate, metabolite, deuterated analog, derivative, or prodrug thereof. In some embodiments, the serotonin receptor modulator is roluperiodone or a pharmaceutically acceptable salt, solvate, metabolite, deuterated analog, derivative, or prodrug thereof. In some embodiments, the serotonin receptor modulator is volinanserin or a pharmaceutically acceptable salt, solvate, metabolite, deuterated analog, derivative, or prodrug thereof. In some embodiments, the serotonin receptor modulator is ritanserin or a pharmaceutically acceptable salt, solvate, metabolite, deuterated analog, derivative, or prodrug thereof. In some embodiments, the serotonin receptor modulator is nelotanserin or a pharmaceutically acceptable salt, solvate, metabolite, deuterated analog, derivative, or prodrug thereof. In some embodiments, the serotonin receptor modulator is pruvanserin or a pharmaceutically acceptable salt, solvate, metabolite, deuterated analog, derivative, or prodrug thereof. In some embodiments, the serotonin receptor modulator is flibanserin or a pharmaceutically acceptable salt, solvate, metabolite, deuterated analog, derivative, or prodrug thereof.

In some embodiments, the serotonin receptor modulator for use with the solid forms of 4-OH-DIPT hemi-glutarate hydrochloride disclosed herein, including those described in Table 5, is eplivanserin, wherein the eplivanserin is administered in about 1 mg to about 40 mg, or about 5 mg to about 10 mg, and the 4-OH-DIPT hemi-glutarate hydrochloride forms disclosed herein, including those described in Table 5, are administered in about 1 mg to about 50 mg, or about 3 mg to about 10 mg, 15 mg, 20 mg, 25 mg, or 30 mg.

In some embodiments, the serotonin receptor modulator for use with the solid forms of 4-OH-DIPT hemi-glutarate hydrochloride disclosed herein, including those described in Table 5, is volinanserin, wherein the volinanserin is administered in about 1 mg to about 60 mg, or about 5 mg to about 20 mg, and the 4-OH-DIPT hemi-glutarate hydrochloride forms disclosed herein, including those described in Table 5, are administered in about 1 mg to about 50 mg, or about 3 mg to about 10 mg, 15 mg, 20 mg, 25 mg, or 30 mg.

In some embodiments, the serotonin receptor modulator for use with solid forms of 4-OH-DIPT hemi-glutarate hydrochloride disclosed herein, including those described in Table 5, is ketanserin, wherein the ketanserin is administered in about 10 mg to about 80 mg, about 30 mg to about 50 mg, or about 40 mg, and the 4-OH-DIPT hemi-glutarate hydrochloride forms disclosed herein, including those described in Table 5, are administered in about 1 mg to about 50 mg, or about 3 mg to about 10 mg, 15 mg, 20 mg, 25 mg, or 30 mg.

In some embodiments, the serotonin receptor modulator for use with the solid forms of 4-OH-DIPT hemi-glutarate hydrochloride disclosed herein, including those described in Table 5, is ritanserin, wherein the ritanserin is administered in about 1 mg to about 40 mg, or about 2.5 mg to about 10 mg, and the 4-OH-DIPT hemi-glutarate hydrochloride forms disclosed herein, including those described in Table 5, are administered in about 1 mg to about 50 mg, or about 3 mg to about 10 mg, 15 mg, 20 mg, 25 mg, or 30 mg.

In some embodiments, the serotonin receptor modulator for use with the solid forms of 4-OH-DIPT hemi-glutarate hydrochloride disclosed herein, including those described in Table 5, is pimavanserin, wherein the pimavanserin is administered in about 1 mg to about 60 mg, or about 17 mg to about 34 mg, and the 4-OH-DIPT hemi-glutarate hydrochloride forms disclosed herein, including those described in Table 5, are administered in about 1 mg to about 50 mg, or about 3 mg to about 10 mg, 15 mg, 20 mg, 25 mg, or 30 mg.

In some embodiments, the serotonin receptor modulator for use with the solid forms of 4-OH-DIPT hemi-glutarate hydrochloride disclosed herein, including those described in Table 5, is nelotanserin, wherein the nelotanserin is administered in about 1 mg to about 80 mg, or about 40 mg to about 80 mg, and the 4-OH-DIPT hemi-glutarate hydrochloride forms disclosed herein, including those described in Table 5, are administered in about 1 mg to about 50 mg, or about 3 mg to about 10 mg, 15 mg, 20 mg, 25 mg, or 30 mg.

In some embodiments, the serotonin receptor modulator for use with the solid forms of 4-OH-DIPT hemi-glutarate hydrochloride disclosed herein, including those described in Table 5, is pruvanserin, wherein the pruvanserin is administered in about 1 mg to about 40 mg, or about 3 mg to about 10 mg, and the 4-OH-DIPT hemi-glutarate hydrochloride forms disclosed herein, including those described in Table 5, are administered in about 1 mg to about 50 mg, or about 3 mg to about 10 mg, 15 mg, 20 mg, 25 mg, or 30 mg.

In some embodiments, the serotonin receptor modulator for use with the solid forms of 4-OH-DIPT hemi-glutarate hydrochloride disclosed herein, including those described in Table 5, is flibanserin, wherein the flibanserin is administered in about 10 mg to about 200 mg, or about 80 mg to about 120 mg, or about 100 mg, and the 4-OH-DIPT hemi-glutarate hydrochloride forms disclosed herein, including those described in Table 5, are administered in about 1 mg to about 50 mg, or about 3 mg to about 10 mg, 15 mg, 20 mg, 25 mg, or 30 mg.

In some embodiments, the serotonin receptor modulator for use with the solid forms of 4-OH-DIPT hemi-glutarate hydrochloride disclosed herein, including those described in Table 5, is olanzapine, wherein the olanzapine is administered in about 2.5 mg to about 30 mg, or about 5 mg or about 10 mg, or about 20 mg or about 25 mg, and the solid forms of 4-OH-DIPT hemi-glutarate hydrochloride disclosed herein, including those described in Table 5, are administered in about 1 mg to about 50 mg, or about 3 mg to about 10 mg, 15 mg, 20 mg, 25 mg, or 30 mg.

In some embodiments, the serotonin receptor modulator for use with the solid forms of 4-OH-DIPT hemi-glutarate hydrochloride disclosed herein, including those described in Table 5, is an extended-release of olanzapine such as ZYPREXA RELPREVV, wherein the extended release olanzapine is administered in about 50 mg to about 450 mg, or about 150 mg or about 210 mg, or about 300 mg or about 405 mg, and the solid forms of 4-OH-DIPT hemi-glutarate hydrochloride disclosed herein, including those described in Table 5, are administered in about 1 mg to about 50 mg, or about 3 mg to about 10 mg, 15 mg, 20 mg, 25 mg, or 30 mg.

In some embodiments, the serotonin receptor modulator for use with the solid forms of 4-OH-DIPT hemi-glutarate hydrochloride disclosed herein, including those described in Table 5, is quetiapine, wherein the quetiapine is administered in about 25 mg to about 800 mg, or about 50 mg to about 100 mg, or about 150 mg or about 200 mg or about 250 mg or about 300 mg, and the solid forms of 4-OH-DIPT hemi-glutarate hydrochloride disclosed herein, including those described in Table 5, are administered in about 1 mg to about 50 mg, or about 3 mg to about 10 mg, 15 mg, 20 mg, 25 mg, or 30 mg.

In some embodiments, the serotonin receptor modulator for use with the solid forms of 4-OH-DIPT hemi-glutarate hydrochloride disclosed herein, including those described in Table 5, is an extended-release of quetiapine, wherein the extended-release of quetiapine is administered in about 50 mg to about 300 mg, or about 50 mg or about 100 mg or about 200 mg, or about 300 mg, and the solid forms of 4-OH-DIPT hemi-glutarate hydrochloride disclosed herein, including those described in Table 5, are administered in about 1 mg to about 50 mg, or about 3 mg to about 10 mg, 15 mg, 20 mg, 25 mg, or 30 mg.

In some embodiments, the serotonin receptor modulator for use with the solid forms of 4-OH-DIPT hemi-glutarate hydrochloride disclosed herein, including those described in Table 5, is risperidone, wherein the risperidone is administered in about 0.5 mg to about 20 mg or about 0.5 mg, or about 1 mg, or about 2 mg, or about 3 mg or about 4 mg or about 5 mg or about 7.5 mg or about 10 mg or about 16 mg, and the solid forms of 4-OH-DIPT hemi-glutarate hydrochloride disclosed herein, including those described in Table 5, are administered in about 1 mg to about 50 mg, or about 3 mg to about 10 mg, 15 mg, 20 mg, 25 mg, or 30 mg.

In some embodiments, the serotonin receptor modulator for use with the solid forms of 4-OH-DIPT hemi-glutarate hydrochloride disclosed herein, including those described in Table 5, is an extended-release of risperidone including RISPERDAL CONSTA, wherein the extended-release of risperidone is administered in about 12.5 mg, or about 25 mg, or about 37.5 mg, or about 50 mg, and the solid forms of 4-OH-DIPT hemi-glutarate hydrochloride disclosed herein, including those described in Table 5, are administered in about 1 mg to about 50 mg, or about 3 mg to about 10 mg, 15 mg, 20 mg, 25 mg, or 30 mg.

In certain embodiments, such as those described above a solid form of 4-OH-DIPT hemi-glutarate hydrochloride disclosed herein, including those described in Table 5, is co-administered with a serotonin receptor modulator in the same or in separate compositions. In one embodiment, the serotonin receptor modulator is administered prior to the solid form of 4-OH-DIPT hemi-glutarate hydrochloride disclosed herein, including those described in Table 5. In one embodiment, the solid form of 4-OH-DIPT hemi-glutarate hydrochloride disclosed herein, including those described in Table 5, is administered in a modified release formulation such that the subject is effectively pretreated with serotonin receptor modulator prior to release of an effective amount of the 4-OH-DIPT hemi-glutarate hydrochloride. In some embodiments the serotonin receptor modulator is part of a single fixed dose formulation that releases serotonin receptor modulator first followed by the 4-OH-DIPT hemi-glutarate hydrochloride on two different release profiles. In another embodiment the serotonin receptor modulator is administered first as a single dosage and after a length of time, the solid form of 4-OH-DIPT hemi-glutarate hydrochloride disclosed herein, including those described in Table 5, is administered as a second dosage separate from the first dosage. Thus, in some embodiments, the serotonin receptor modulator is administered or released from a composition provided herein prior to the administration and/or release of the 4-OH-DIPT hemi-glutarate hydrochloride form disclosed herein, including those described in Table 5. This allows pretreatment to attenuate activation of the serotonin receptor by the 4-OH-DIPT hemi-glutarate hydrochloride form disclosed herein, including those described in Table 5.

In some embodiments, the serotonin receptor modulator is administered or released from the composition provided herein to pretreat a subject by at least about at about 5 minutes, 10 minutes, 20 minutes, 30 minutes, 40 minutes, 50 minutes, 1 hour, 1.25 hours, 1.5 hours, 2 hours, or 3 hours prior to the release of the solid form of 4-OH-DIPT hemi-glutarate hydrochloride disclosed herein, including those described in Table 5. In some embodiments, the serotonin receptor modulator attenuates the activation of the serotonin receptor when the serotonin receptor modulator is used to pretreat at most about 3 hours, 4 hours, 5 hours, 6 hours, 7 hours, 8 hours, 9 hours, or more than 9 hours prior to the release of the psychedelic. In some embodiments, the serotonin receptor modulator attenuates the activation of the serotonin receptor when the serotonin receptor modulator is used to pretreat in a range of about 5 minutes to about 3 hours, about 10 minutes to about 3 hours, about 20 minutes to about 3 hours, about 30 minutes to about 3 hours, about 40 minutes to about 3 hours, about 50 minutes to about 3 hours, about 1 hour to about 3 hours, about 5 minutes to about 2 hours, about 10 minutes to about 2 hours, about 20 minutes to about 2 hours, about 30 minutes to about 2 hours, about 40 minutes to about 2 hours, about 50 minutes to about 2 hours, about 1 hour to about 2 hours, about 5 minutes to about 1 hour, about 10 minutes to about 1 hour, about 20 minutes to about 1 hour, about 30 minutes to about 1 hour, about 40 minutes to about 1 hour, or about 50 minutes to about 1 hour prior to the release of the psychedelic.

In a preferred embodiment, the serotonin receptor modulator is administered at about 1 hour to about 3 hours prior to the administration of the psychedelic.

In some embodiments, the serotonin receptor modulator is eplivanserin, wherein the eplivanserin is administered to pretreat at least 15 minutes prior to the administration of the solid form of 4-OH-DIPT hemi-glutarate hydrochloride disclosed herein, including those described in Table 5. In some embodiments, the serotonin receptor modulator is eplivanserin, wherein the eplivanserin is administered to pretreat between at least 30 minutes prior and 360 minutes prior to the release or administration of the solid form of 4-OH-DIPT hemi-glutarate hydrochloride disclosed herein, including those described in Table 5. In some embodiments, the serotonin receptor modulator is eplivanserin, wherein the eplivanserin is administered to pretreat between at least 60 minutes prior and 360 minutes prior to the release or administration the solid form of 4-OH-DIPT hemi-glutarate hydrochloride disclosed herein, including those described in Table 5. In some embodiments, the serotonin receptor modulator is eplivanserin, wherein the eplivanserin is administered to pretreat between at least 90 minutes and 240 minutes prior to the solid form of 4-OH-DIPT hemi-glutarate hydrochloride disclosed herein, including those described in Table 5. In some embodiments, the serotonin receptor modulator is eplivanserin, wherein the eplivanserin is administered to pretreat at least 120 minutes prior to the solid form of 4-OH-DIPT hemi-glutarate hydrochloride disclosed herein, including those described in Table 5.

In some embodiments, the serotonin receptor modulator is eplivanserin, wherein the eplivanserin is administered to pretreat at least 150 minutes prior to the solid form of 4-OH-DIPT hemi-glutarate hydrochloride disclosed herein, including those described in Table 5. In some embodiments, the serotonin receptor modulator is eplivanserin, wherein the eplivanserin is administered to pretreat between about 15 minutes and about 150 minutes prior to the solid form of 4-OH-DIPT hemi-glutarate hydrochloride disclosed herein, including those described in Table 5. In some embodiments, the serotonin receptor modulator is eplivanserin, wherein the eplivanserin is administered to pretreat at least 180 minutes prior to the solid form of 4-OH-DIPT hemi-glutarate hydrochloride disclosed herein, including those described in Table 5. In some embodiments, the serotonin receptor modulator is eplivanserin, wherein the eplivanserin is administered to pretreat at least 210 minutes prior to the solid form of 4-OH-DIPT hemi-glutarate hydrochloride disclosed herein, including those described in Table 5. In some embodiments, the serotonin receptor modulator is eplivanserin, wherein the eplivanserin is administered to pretreat at least 240 minutes prior to the solid form of 4-OH-DIPT hemi-glutarate hydrochloride disclosed herein, including those described in Table 5.

In some embodiments, the serotonin receptor modulator is eplivanserin, wherein the eplivanserin is administered to pretreat at least 270 minutes prior to the solid form of 4-OH-DIPT hemi-glutarate hydrochloride disclosed herein, including those described in Table 5. In some embodiments, the serotonin receptor modulator is eplivanserin, wherein the eplivanserin is administered to pretreat at least 300 minutes prior to the solid form of 4-OH-DIPT hemi-glutarate hydrochloride disclosed herein, including those described in Table 5. In some embodiments, the serotonin receptor modulator is eplivanserin, wherein the eplivanserin is administered to pretreat at least 330 minutes prior to the solid form of 4-OH-DIPT hemi-glutarate hydrochloride disclosed herein, including those described in Table 5. In some embodiments, the serotonin receptor modulator is eplivanserin, wherein the eplivanserin is administered to pretreat at least 360 minutes prior to administration or release of the solid form of 4-OH-DIPT hemi-glutarate hydrochloride disclosed herein, including those described in Table 5.

In some preferred embodiments, the serotonin receptor modulator is eplivanserin, wherein eplivanserin is administered to pretreat between about 60 minutes and about 180 minutes prior to the administration or release of the solid form of 4-OH-DIPT hemi-glutarate hydrochloride disclosed herein, including those described in Table 5.

In some embodiments, the serotonin receptor modulator is volinanserin, wherein the volinanserin is administered to pretreat a subject between at least 15 minutes and 360 minutes prior to the administration or release of the solid form of 4-OH-DIPT hemi-glutarate hydrochloride disclosed herein, including those described in Table 5. In some embodiments, the serotonin receptor modulator is volinanserin, wherein the volinanserin is administered to pretreat between at least 30 minutes and 360 minutes prior to the administration or release of the solid form of 4-OH-DIPT hemi-glutarate hydrochloride disclosed herein, including those described in Table 5. In some embodiments, the serotonin receptor modulator is volinanserin, wherein the volinanserin is administered to pretreat between at least 60 minutes and 240 minutes prior to the administration or release of the solid form of 4-OH-DIPT hemi-glutarate hydrochloride disclosed herein, including those described in Table 5. In some embodiments, the serotonin receptor modulator is volinanserin, wherein the volinanserin is administered to pretreat at least 90 minutes prior to solid form of 4-OH-DIPT hemi-glutarate hydrochloride disclosed herein, including those described in Table 5. In some embodiments, the serotonin receptor modulator is volinanserin, wherein the volinanserin is administered to pretreat at least 120 minutes prior to the solid form of 4-OH-DIPT hemi-glutarate hydrochloride disclosed herein, including those described in Table 5.

In some embodiments, the serotonin receptor modulator is volinanserin, wherein the volinanserin is administered to pretreat at least 150 minutes prior to the solid form of 4-OH-DIPT hemi-glutarate hydrochloride disclosed herein, including those described in Table 5. In some embodiments, the serotonin receptor modulator is volinanserin, wherein the volinanserin is administered to pretreat between about 15 minutes and about 150 minutes prior to the solid form of 4-OH-DIPT hemi-glutarate hydrochloride disclosed herein, including those described in Table 5. In some embodiments, the serotonin receptor modulator is volinanserin, wherein the volinanserin is administered to pretreat at least 180 minutes prior to the solid form of 4-OH-DIPT hemi-glutarate hydrochloride disclosed herein, including those described in Table 5. In some embodiments, the serotonin receptor modulator is volinanserin, wherein the volinanserin is administered to pretreat at least 210 minutes prior to the solid form of 4-OH-DIPT hemi-glutarate hydrochloride disclosed herein, including those described in Table 5. In some embodiments, the serotonin receptor modulator is volinanserin, wherein the volinanserin is administered to pretreat at least 240 minutes prior to the solid form of 4-OH-DIPT hemi-glutarate hydrochloride disclosed herein, including those described in Table 5. In some embodiments, the serotonin receptor modulator is volinanserin, wherein the volinanserin is administered to pretreat at least 270 minutes prior to the solid form of 4-OH-DIPT hemi-glutarate hydrochloride disclosed herein, including those described in Table 5. In some embodiments, the serotonin receptor modulator is volinanserin, wherein the volinanserin is administered to pretreat at least 300 minutes prior to the solid form of 4-OH-DIPT hemi-glutarate hydrochloride disclosed herein, including those described in Table 5. In some embodiments, the serotonin receptor modulator is volinanserin, wherein the volinanserin is administered to pretreat at least 330 minutes prior to solid form of 4-OH-DIPT hemi-glutarate hydrochloride disclosed herein, including those described in Table 5. In some embodiments, the serotonin receptor modulator is volinanserin, wherein the volinanserin is administered to pretreat at least 360 minutes prior to the solid form of 4-OH-DIPT hemi-glutarate hydrochloride disclosed herein, including those described in Table 5. In some preferred embodiments, the serotonin receptor modulator is volinanserin, wherein volinanserin is administered to pretreat between about 60 minutes and about 180 minutes prior to the administration of the solid form of 4-OH-DIPT hemi-glutarate hydrochloride disclosed herein, including those described in Table 5.

In some embodiments, the serotonin receptor modulator is ketanserin, wherein the ketanserin is administered to pretreat at least 15 minutes prior to the administration of the solid form of 4-OH-DIPT hemi-glutarate hydrochloride disclosed herein, including those described in Table 5. In some embodiments, the serotonin receptor modulator is ketanserin, wherein the ketanserin is administered to pretreat between at least 30 minutes and 360 minutes prior to the administration or release of the solid form of 4-OH-DIPT hemi-glutarate hydrochloride disclosed herein, including those described in Table 5. In some embodiments, the serotonin receptor modulator is ketanserin, wherein the ketanserin is administered to pretreat between at least 60 minutes and 240 minutes prior to the administration or release of the solid form of 4-OH-DIPT hemi-glutarate hydrochloride disclosed herein, including those described in Table 5. In some embodiments, the serotonin receptor modulator is ketanserin, wherein the ketanserin is administered to pretreat at least 90 minutes prior to the solid form of 4-OH-DIPT hemi-glutarate hydrochloride disclosed herein, including those described in Table 5. In some embodiments, the serotonin receptor modulator is ketanserin, wherein the ketanserin is administered to pretreat at least 120 minutes prior to the solid form of 4-OH-DIPT hemi-glutarate hydrochloride disclosed herein, including those described in Table 5. In some embodiments, the serotonin receptor modulator is ketanserin, wherein the ketanserin is administered to pretreat at least 150 minutes prior to the solid form of 4-OH-DIPT hemi-glutarate hydrochloride disclosed herein, including those described in Table 5. In some embodiments, the serotonin receptor modulator is ketanserin, wherein the ketanserin is administered to pretreat between about 15 minutes and about 150 minutes prior to the solid form of 4-OH-DIPT hemi-glutarate hydrochloride disclosed herein, including those described in Table 5. In some embodiments, the serotonin receptor modulator is ketanserin, wherein the ketanserin is administered to pretreat at least 180 minutes prior to the solid form of 4-OH-DIPT hemi-glutarate hydrochloride disclosed herein, including those described in Table 5. In some embodiments, the serotonin receptor modulator is ketanserin, wherein the ketanserin is administered to pretreat at least 210 minutes prior to the solid form of 4-OH-DIPT hemi-glutarate hydrochloride disclosed herein, including those described in Table 5. In some embodiments, the serotonin receptor modulator is ketanserin, wherein the ketanserin is administered to pretreat at least 240 minutes prior to the solid form of 4-OH-DIPT hemi-glutarate hydrochloride disclosed herein, including those described in Table 5. In some embodiments, the serotonin receptor modulator is ketanserin, wherein the ketanserin is administered to pretreat at least 270 minutes prior to the solid form of 4-OH-DIPT hemi-glutarate hydrochloride disclosed herein, including those described in Table 5. In some embodiments, the serotonin receptor modulator is ketanserin, wherein the ketanserin is administered to pretreat at least 300 minutes prior to the solid form of 4-OH-DIPT hemi-glutarate hydrochloride disclosed herein, including those described in Table 5. In some embodiments, the serotonin receptor modulator is ketanserin, wherein the ketanserin is administered to pretreat at least 330 minutes prior to the solid form of 4-OH-DIPT hemi-glutarate hydrochloride disclosed herein, including those described in Table 5. In some embodiments, the serotonin receptor modulator is ketanserin, wherein the ketanserin is administered to pretreat at least 360 minutes prior to the solid form of 4-OH-DIPT hemi-glutarate hydrochloride disclosed herein, including those described in Table 5. In some preferred embodiments, the serotonin receptor modulator is ketanserin, wherein ketanserin is administered to pretreat between about 60 minutes and about 180 minutes prior to the administration of the solid form of 4-OH-DIPT hemi-glutarate hydrochloride disclosed herein, including those described in Table 5.

In some embodiments, the serotonin receptor modulator is ritanserin, wherein the ritanserin is administered to pretreat at least 15 minutes prior to the administration of the solid form of 4-OH-DIPT hemi-glutarate hydrochloride disclosed herein, including those described in Table 5. In some embodiments, the serotonin receptor modulator is ritanserin, wherein the ritanserin is administered to pretreat at least 30 minutes prior to the solid form of 4-OH-DIPT hemi-glutarate hydrochloride disclosed herein, including those described in Table 5. In some embodiments, the serotonin receptor modulator is ritanserin wherein the ritanserin is administered to pretreat between at least 60 minutes and 240 minutes prior to the administration or release of the solid form of 4-OH-DIPT hemi-glutarate hydrochloride disclosed herein, including those described in Table 5. In some embodiments, the serotonin receptor modulator is ritanserin, wherein the ritanserin is administered to pretreat at least 90 minutes prior to the solid form of 4-OH-DIPT hemi-glutarate hydrochloride disclosed herein, including those described in Table 5. In some embodiments, the serotonin receptor modulator is ritanserin, wherein the ritanserin is administered to pretreat at least 120 minutes prior to the solid form of 4-OH-DIPT hemi-glutarate hydrochloride disclosed herein, including those described in Table 5. In some embodiments, the serotonin receptor modulator is ritanserin, wherein the ritanserin is administered to pretreat at least 150 minutes prior to the solid form of 4-OH-DIPT hemi-glutarate hydrochloride disclosed herein, including those described in Table 5. In some embodiments, the serotonin receptor modulator is ritanserin, wherein the ritanserin is administered to pretreat between about 15 minutes and about 150 minutes prior to the solid form of 4-OH-DIPT hemi-glutarate hydrochloride disclosed herein, including those described in Table 5. In some embodiments, the serotonin receptor modulator is ritanserin, wherein the ritanserin is administered to pretreat at least 180 minutes prior to the solid form of 4-OH-DIPT hemi-glutarate hydrochloride disclosed herein, including those described in Table 5. In some embodiments, the serotonin receptor modulator is ritanserin, wherein the ritanserin is administered to pretreat at least 210 minutes prior to the solid form of 4-OH-DIPT hemi-glutarate hydrochloride disclosed herein, including those described in Table 5. In some embodiments, the serotonin receptor modulator is ritanserin, wherein the ritanserin is administered to pretreat at least 240 minutes prior to the solid form of 4-OH-DIPT hemi-glutarate hydrochloride disclosed herein, including those described in Table 5. In some embodiments, the serotonin receptor modulator is ritanserin, wherein the ritanserin is administered to pretreat at least 270 minutes prior to the solid form of 4-OH-DIPT hemi-glutarate hydrochloride disclosed herein, including those described in Table 5. In some embodiments, the serotonin receptor modulator is ritanserin, wherein the ritanserin is administered to pretreat at least 300 minutes prior to the solid form of 4-OH-DIPT hemi-glutarate hydrochloride disclosed herein, including those described in Table 5. In some embodiments, the serotonin receptor modulator is ritanserin, wherein the ritanserin is administered to pretreat at least 330 minutes prior to the solid form of 4-OH-DIPT hemi-glutarate hydrochloride disclosed herein, including those described in Table 5. In some embodiments, the serotonin receptor modulator is ritanserin, wherein the ritanserin is administered to pretreat at least 360 minutes prior to the solid form of 4-OH-DIPT hemi-glutarate hydrochloride disclosed herein, including those described in Table 5. In some preferred embodiments, the serotonin receptor modulator is ritanserin, wherein ritanserin is administered to pretreat between about 60 minutes and about 180 minutes prior to the administration of the solid form of 4-OH-DIPT hemi-glutarate hydrochloride disclosed herein, including those described in Table 5.

In some embodiments, the serotonin receptor modulator is pimavanserin, wherein the pimavanserin is administered to pretreat at least 15 minutes prior to the administration of the solid form of 4-OH-DIPT hemi-glutarate hydrochloride disclosed herein, including those described in Table 5. In some embodiments, the serotonin receptor modulator is pimavanserin, wherein the pimavanserin is administered to pretreat at least 30 minutes prior to the solid form of 4-OH-DIPT hemi-glutarate hydrochloride disclosed herein, including those described in Table 5. In some embodiments, the serotonin receptor modulator is pimavanserin, wherein the pimavanserin is administered to pretreat between at least 60 minutes and 240 minutes prior to the administration or release of the solid form of 4-OH-DIPT hemi-glutarate hydrochloride disclosed herein, including those described in Table 5. In some embodiments, the serotonin receptor modulator is pimavanserin, wherein the pimavanserin is administered to pretreat at least 90 minutes prior to the solid form of 4-OH-DIPT hemi-glutarate hydrochloride disclosed herein, including those described in Table 5. In some embodiments, the serotonin receptor modulator is pimavanserin, wherein the pimavanserin is administered to pretreat at least 120 minutes prior to the solid form of 4-OH-DIPT hemi-glutarate hydrochloride disclosed herein, including those described in Table 5. In some embodiments, the serotonin receptor modulator is pimavanserin, wherein the pimavanserin is administered to pretreat at least 150 minutes prior to the solid form of 4-OH-DIPT hemi-glutarate hydrochloride disclosed herein, including those described in Table 5. In some embodiments, the serotonin receptor modulator is pimavanserin, wherein the pimavanserin is administered to pretreat between about 15 minutes and about 150 minutes prior to the solid form of 4-OH-DIPT hemi-glutarate hydrochloride disclosed herein, including those described in Table 5. In some embodiments, the serotonin receptor modulator is pimavanserin, wherein the pimavanserin is administered to pretreat at least 180 minutes prior to the solid form of 4-OH-DIPT hemi-glutarate hydrochloride disclosed herein, including those described in Table 5. In some embodiments, the serotonin receptor modulator is pimavanserin, wherein the pimavanserin is administered to pretreat at least 210 minutes prior to the solid form of 4-OH-DIPT hemi-glutarate hydrochloride disclosed herein, including those described in Table 5. In some embodiments, the serotonin receptor modulator is pimavanserin, wherein the pimavanserin is administered to pretreat at least 240 minutes prior to the solid form of 4-OH-DIPT hemi-glutarate hydrochloride disclosed herein, including those described in Table 5. In some embodiments, the serotonin receptor modulator is pimavanserin, wherein the pimavanserin is administered to pretreat at least 270 minutes prior to the solid form of 4-OH-DIPT hemi-glutarate hydrochloride disclosed herein, including those described in Table 5. In some embodiments, the serotonin receptor modulator is pimavanserin, wherein the pimavanserin is administered to pretreat at least 300 minutes prior to the solid form of 4-OH-DIPT hemi-glutarate hydrochloride disclosed herein, including those described in Table 5. In some embodiments, the serotonin receptor modulator is pimavanserin, wherein the pimavanserin is administered to pretreat at least 330 minutes prior to the solid form of 4-OH-DIPT hemi-glutarate hydrochloride disclosed herein, including those described in Table 5. In some embodiments, the serotonin receptor modulator is pimavanserin, wherein the pimavanserin is administered to pretreat at least 360 minutes prior to the solid form of 4-OH-DIPT hemi-glutarate hydrochloride disclosed herein, including those described in Table 5. In some preferred embodiments, the serotonin receptor modulator is pimavanserin, wherein pimavanserin is administered to pretreat between about 60 minutes and about 180 minutes prior to the administration of the solid form of 4-OH-DIPT hemi-glutarate hydrochloride disclosed herein, including those described in Table 5.

In some embodiments, the serotonin receptor modulator is nelotanserin, wherein the nelotanserin is administered to pretreat at least 15 minutes prior to the administration of the solid form of 4-OH-DIPT hemi-glutarate hydrochloride disclosed herein, including those described in Table 5. In some embodiments, the serotonin receptor modulator is nelotanserin, wherein the nelotanserin is administered to pretreat at least 30 minutes prior to the solid form of 4-OH-DIPT hemi-glutarate hydrochloride disclosed herein, including those described in Table 5. In some embodiments, the serotonin receptor modulator is nelotanserin, wherein the nelotanserin is administered to pretreat between at least 60 minutes and 240 minutes prior to the administration or release of the solid form of 4-OH-DIPT hemi-glutarate hydrochloride disclosed herein, including those described in Table 5. In some embodiments, the serotonin receptor modulator is nelotanserin, wherein the nelotanserin is administered to pretreat at least 90 minutes prior to the solid form of 4-OH-DIPT hemi-glutarate hydrochloride disclosed herein, including those described in Table 5. In some embodiments, the serotonin receptor modulator is nelotanserin, wherein the nelotanserin is administered to pretreat at least 120 minutes prior to the solid form of 4-OH-DIPT hemi-glutarate hydrochloride disclosed herein, including those described in Table 5.

In some embodiments, the serotonin receptor modulator is nelotanserin, wherein the nelotanserin is administered to pretreat at least 150 minutes prior to the solid form of 4-OH-DIPT hemi-glutarate hydrochloride disclosed herein, including those described in Table 5. In some embodiments, the serotonin receptor modulator is nelotanserin, wherein the nelotanserin is administered to pretreat between about 15 minutes and about 150 minutes prior to the solid form of 4-OH-DIPT hemi-glutarate hydrochloride disclosed herein, including those described in Table 5. In some embodiments, the serotonin receptor modulator is nelotanserin, wherein the nelotanserin is administered to pretreat at least 180 minutes prior to the solid form of 4-OH-DIPT hemi-glutarate hydrochloride disclosed herein, including those described in Table 5. In some embodiments, the serotonin receptor modulator is nelotanserin, wherein the nelotanserin is administered to pretreat at least 210 minutes prior to the solid form of 4-OH-DIPT hemi-glutarate hydrochloride disclosed herein, including those described in Table 5. In some embodiments, the serotonin receptor modulator is nelotanserin, wherein the nelotanserin is administered to pretreat at least 240 minutes prior to the solid form of 4-OH-DIPT hemi-glutarate hydrochloride disclosed herein, including those described in Table 5. In some embodiments, the serotonin receptor modulator is nelotanserin, wherein the nelotanserin is administered to pretreat at least 270 minutes prior to the solid form of 4-OH-DIPT hemi-glutarate hydrochloride disclosed herein, including those described in Table 5.

In some embodiments, the serotonin receptor modulator is nelotanserin, wherein the nelotanserin is administered to pretreat at least 300 minutes prior to the solid form of 4-OH-DIPT hemi-glutarate hydrochloride disclosed herein, including those described in Table 5. In some embodiments, the serotonin receptor modulator is nelotanserin, wherein the nelotanserin is administered to pretreat at least 330 minutes prior to the solid form of 4-OH-DIPT hemi-glutarate hydrochloride disclosed herein, including those described in Table 5. In some embodiments, the serotonin receptor modulator is nelotanserin, wherein the nelotanserin is administered to pretreat at least 360 minutes prior to the solid form of 4-OH-DIPT hemi-glutarate hydrochloride disclosed herein, including those described in Table 5. In some preferred embodiments, the serotonin receptor modulator is nelotanserin, wherein nelotanserin is administered to pretreat between about 60 minutes and about 180 minutes prior to the administration of the solid form of 4-OH-DIPT hemi-glutarate hydrochloride disclosed herein, including those described in Table 5.

In some embodiments, the serotonin receptor modulator is pruvanserin, wherein the pruvanserin is administered to pretreat at least 15 minutes prior to the administration of the solid form of 4-OH-DIPT hemi-glutarate hydrochloride disclosed herein, including those described in Table 5. In some embodiments, the serotonin receptor modulator is pruvanserin, wherein the pruvanserin is administered to pretreat at least 30 minutes prior to the solid form of 4-OH-DIPT hemi-glutarate hydrochloride disclosed herein, including those described in Table 5. In some embodiments, the serotonin receptor modulator is pruvanserin, wherein the pruvanserin is administered to pretreat between at least 60 minutes and 240 minutes prior to the administration or release of the solid form of 4-OH-DIPT hemi-glutarate hydrochloride disclosed herein, including those described in Table 5. In some embodiments, the serotonin receptor modulator is pruvanserin, wherein the pruvanserin is administered to pretreat at least 90 minutes prior to the solid form of 4-OH-DIPT hemi-glutarate hydrochloride disclosed herein, including those described in Table 5. In some embodiments, the serotonin receptor modulator is pruvanserin, wherein the pruvanserin is administered to pretreat at least 120 minutes prior to the solid form of 4-OH-DIPT hemi-glutarate hydrochloride disclosed herein, including those described in Table 5. In some embodiments, the serotonin receptor modulator is pruvanserin, wherein the pruvanserin is administered to pretreat at least 150 minutes prior to the solid form of 4-OH-DIPT hemi-glutarate hydrochloride disclosed herein, including those described in Table 5. In some embodiments, the serotonin receptor modulator is pruvanserin, wherein the pruvanserin is administered to pretreat between about 15 minutes and about 150 minutes prior to the solid form of 4-OH-DIPT hemi-glutarate hydrochloride disclosed herein, including those described in Table 5. In some embodiments, the serotonin receptor modulator is pruvanserin, wherein the pruvanserin is administered to pretreat at least 180 minutes prior to the solid form of 4-OH-DIPT hemi-glutarate hydrochloride disclosed herein, including those described in Table 5. In some embodiments, the serotonin receptor modulator is pruvanserin, wherein the pruvanserin is administered to pretreat at least 210 minutes prior to the solid form of 4-OH-DIPT hemi-glutarate hydrochloride disclosed herein, including those described in Table 5.

In some embodiments, the serotonin receptor modulator is pruvanserin, wherein the pruvanserin is administered to pretreat at least 240 minutes prior to the solid form of 4-OH-DIPT hemi-glutarate hydrochloride disclosed herein, including those described in Table 5. In some embodiments, the serotonin receptor modulator is pruvanserin, wherein the pruvanserin is administered to pretreat at least 270 minutes prior to the solid form of 4-OH-DIPT hemi-glutarate hydrochloride disclosed herein, including those described in Table 5. In some embodiments, the serotonin receptor modulator is pruvanserin, wherein the pruvanserin is administered to pretreat at least 300 minutes prior to the solid form of 4-OH-DIPT hemi-glutarate hydrochloride disclosed herein, including those described in Table 5. In some embodiments, the serotonin receptor modulator is pruvanserin, wherein the pruvanserin is administered to pretreat at least 330 minutes prior to the solid form of 4-OH-DIPT hemi-glutarate hydrochloride disclosed herein, including those described in Table 5. In some embodiments, the serotonin receptor modulator is pruvanserin, wherein the pruvanserin is administered to pretreat at least 360 minutes prior to the solid form of 4-OH-DIPT hemi-glutarate hydrochloride disclosed herein, including those described in Table 5. In some preferred embodiments, the serotonin receptor modulator is pruvanserin, wherein pruvanserin is administered to pretreat between about 60 minutes and about 180 minutes prior to the administration of the solid form of 4-OH-DIPT hemi-glutarate hydrochloride disclosed herein, including those described in Table 5.

In some embodiments, the serotonin receptor modulator is flibanserin, wherein the flibanserin is administered to pretreat at least 15 minutes prior to the administration of the solid form of 4-OH-DIPT hemi-glutarate hydrochloride disclosed herein, including those described in Table 5. In some embodiments, the serotonin receptor modulator is flibanserin, wherein the flibanserin is administered to pretreat at least 30 minutes prior to the solid form of 4-OH-DIPT hemi-glutarate hydrochloride disclosed herein, including those described in Table 5. In some embodiments, the serotonin receptor modulator is flibanserin, wherein the flibanserin is administered to pretreat between at least 60 minutes and 240 minutes prior to the administration or release of the solid form of 4-OH-DIPT hemi-glutarate hydrochloride disclosed herein, including those described in Table 5. In some embodiments, the serotonin receptor modulator is flibanserin, wherein the flibanserin is administered to pretreat at least 90 minutes prior to the solid form of 4-OH-DIPT hemi-glutarate hydrochloride disclosed herein, including those described in Table 5. In some embodiments, the serotonin receptor modulator is flibanserin, wherein the flibanserin is administered to pretreat at least 120 minutes prior to the solid form of 4-OH-DIPT hemi-glutarate hydrochloride disclosed herein, including those described in Table 5. In some embodiments, the serotonin receptor modulator is flibanserin, wherein the flibanserin is administered to pretreat at least 150 minutes prior to the solid form of 4-OH-DIPT hemi-glutarate hydrochloride disclosed herein, including those described in Table 5. In some embodiments, the serotonin receptor modulator is flibanserin, wherein the flibanserin is administered to pretreat between about 15 minutes and about 150 minutes prior to the solid form of 4-OH-DIPT hemi-glutarate hydrochloride disclosed herein, including those described in Table 5. In some embodiments, the serotonin receptor modulator is flibanserin, wherein the flibanserin is administered to pretreat at least 180 minutes prior to the solid form of 4-OH-DIPT hemi-glutarate hydrochloride disclosed herein, including those described in Table 5. In some embodiments, the serotonin receptor modulator is flibanserin, wherein the flibanserin is administered to pretreat at least 210 minutes prior to the solid form of 4-OH-DIPT hemi-glutarate hydrochloride disclosed herein, including those described in Table 5.

In some embodiments, the serotonin receptor modulator is flibanserin, wherein the flibanserin is administered to pretreat at least 240 minutes prior to the solid form of 4-OH-DIPT hemi-glutarate hydrochloride disclosed herein, including those described in Table 5. In some embodiments, the serotonin receptor modulator is flibanserin, wherein the flibanserin is administered to pretreat at least 270 minutes prior to the solid form of 4-OH-DIPT hemi-glutarate hydrochloride disclosed herein, including those described in Table 5. In some embodiments, the serotonin receptor modulator is flibanserin, wherein the flibanserin is administered to pretreat at least 300 minutes prior to the solid form of 4-OH-DIPT hemi-glutarate hydrochloride disclosed herein, including those described in Table 5. In some embodiments, the serotonin receptor modulator is flibanserin, wherein the flibanserin is administered to pretreat at least 330 minutes prior to the solid form of 4-OH-DIPT hemi-glutarate hydrochloride disclosed herein, including those described in Table 5. In some embodiments, the serotonin receptor modulator is flibanserin, wherein the flibanserin is administered to pretreat at least 360 minutes prior to the solid form of 4-OH-DIPT hemi-glutarate hydrochloride disclosed herein, including those described in Table 5. In some preferred embodiments, the serotonin receptor modulator is flibanserin, wherein flibanserin is administered to pretreat between about 60 minutes and about 180 minutes prior to the administration of the solid form of 4-OH-DIPT hemi-glutarate hydrochloride disclosed herein, including those described in Table 5.

In some embodiments, the serotonin receptor modulator is olanzapine, wherein the olanzapine is administered to pretreat at least 15 minutes prior to the administration of the solid form of 4-OH-DIPT hemi-glutarate hydrochloride disclosed herein, including those described in Table 5. In some embodiments, the serotonin receptor modulator is olanzapine, wherein the olanzapine is administered to pretreat at least 30 minutes prior to the solid form of 4-OH-DIPT hemi-glutarate hydrochloride disclosed herein, including those described in Table 5. In some embodiments, the serotonin receptor modulator is olanzapine, wherein the olanzapine is administered to pretreat between at least 60 minutes and 240 minutes prior to the administration or release of the solid form of 4-OH-DIPT hemi-glutarate hydrochloride disclosed herein, including those described in Table 5. In some embodiments, the serotonin receptor modulator is olanzapine, wherein the olanzapine is administered to pretreat at least 90 minutes prior to the solid form of 4-OH-DIPT hemi-glutarate hydrochloride disclosed herein, including those described in Table 5. In some embodiments, the serotonin receptor modulator is olanzapine, wherein the olanzapine is administered to pretreat at least 120 minutes prior to the solid form of 4-OH-DIPT hemi-glutarate hydrochloride disclosed herein, including those described in Table 5. In some embodiments, the serotonin receptor modulator is olanzapine, wherein the olanzapine is administered to pretreat at least 150 minutes prior to the solid form of 4-OH-DIPT hemi-glutarate hydrochloride disclosed herein, including those described in Table 5. In some embodiments, the serotonin receptor modulator is olanzapine, wherein the olanzapine is administered to pretreat between about 15 minutes and about 150 minutes prior to the solid form of 4-OH-DIPT hemi-glutarate hydrochloride disclosed herein, including those described in Table 5. In some embodiments, the serotonin receptor modulator is olanzapine, wherein the olanzapine is administered to pretreat at least 180 minutes prior to the solid form of 4-OH-DIPT hemi-glutarate hydrochloride disclosed herein, including those described in Table 5. In some embodiments, the serotonin receptor modulator is olanzapine, wherein the olanzapine is administered to pretreat at least 210 minutes prior to the solid form of 4-OH-DIPT hemi-glutarate hydrochloride disclosed herein, including those described in Table 5.

In some embodiments, the serotonin receptor modulator is olanzapine, wherein the olanzapine is administered to pretreat at least 240 minutes prior to the solid form of 4-OH-DIPT hemi-glutarate hydrochloride disclosed herein, including those described in Table 5. In some embodiments, the serotonin receptor modulator is olanzapine, wherein the olanzapine is administered to pretreat at least 270 minutes prior to the solid form of 4-OH-DIPT hemi-glutarate hydrochloride disclosed herein, including those described in Table 5. In some embodiments, the serotonin receptor modulator is olanzapine, wherein the olanzapine is administered to pretreat at least 300 minutes prior to the solid form of 4-OH-DIPT hemi-glutarate hydrochloride disclosed herein, including those described in Table 5. In some embodiments, the serotonin receptor modulator is olanzapine, wherein the olanzapine is administered to pretreat at least 330 minutes prior to the solid form of 4-OH-DIPT hemi-glutarate hydrochloride disclosed herein, including those described in Table 5. In some embodiments, the serotonin receptor modulator is olanzapine, wherein the olanzapine is administered to pretreat at least 360 minutes prior to the solid form of 4-OH-DIPT hemi-glutarate hydrochloride disclosed herein, including those described in Table 5. In some preferred embodiments, the serotonin receptor modulator is olanzapine, wherein olanzapine is administered to pretreat between about 60 minutes and about 180 minutes prior to the administration of the solid form of 4-OH-DIPT hemi-glutarate hydrochloride disclosed herein, including those described in Table 5.

In some embodiments, the serotonin receptor modulator is risperidone, wherein the risperidone is administered to pretreat at least 15 minutes prior to the administration of the solid form of 4-OH-DIPT hemi-glutarate hydrochloride disclosed herein, including those described in Table 5. In some embodiments, the serotonin receptor modulator is risperidone, wherein the risperidone is administered to pretreat at least 30 minutes prior to the solid form of 4-OH-DIPT hemi-glutarate hydrochloride disclosed herein, including those described in Table 5. In some embodiments, the serotonin receptor modulator is risperidone, wherein the risperidone is administered to pretreat between at least 60 minutes and 240 minutes prior to the administration or release of the solid form of 4-OH-DIPT hemi-glutarate hydrochloride disclosed herein, including those described in Table 5. In some embodiments, the serotonin receptor modulator is risperidone, wherein the risperidone is administered to pretreat at least 90 minutes prior to the solid form of 4-OH-DIPT hemi-glutarate hydrochloride disclosed herein, including those described in Table 5. In some embodiments, the serotonin receptor modulator is risperidone, wherein the risperidone is administered to pretreat at least 120 minutes prior to the solid form of 4-OH-DIPT hemi-glutarate hydrochloride disclosed herein, including those described in Table 5. In some embodiments, the serotonin receptor modulator is risperidone, wherein the risperidone is administered to pretreat at least 150 minutes prior to the solid form of 4-OH-DIPT hemi-glutarate hydrochloride disclosed herein, including those described in Table 5. In some embodiments, the serotonin receptor modulator is risperidone, wherein the risperidone is administered to pretreat between about 15 minutes and about 150 minutes prior to the solid form of 4-OH-DIPT hemi-glutarate hydrochloride disclosed herein, including those described in Table 5. In some embodiments, the serotonin receptor modulator is risperidone, wherein the risperidone is administered to pretreat at least 180 minutes prior to the solid form of 4-OH-DIPT hemi-glutarate hydrochloride disclosed herein, including those described in Table 5. In some embodiments, the serotonin receptor modulator is risperidone, wherein the risperidone is administered to pretreat at least 210 minutes prior to the solid form of 4-OH-DIPT hemi-glutarate hydrochloride disclosed herein, including those described in Table 5.

In some embodiments, the serotonin receptor modulator is risperidone, wherein the risperidone is administered to pretreat at least 240 minutes prior to the solid form of 4-OH-DIPT hemi-glutarate hydrochloride disclosed herein, including those described in Table 5. In some embodiments, the serotonin receptor modulator is risperidone, wherein the risperidone is administered to pretreat at least 270 minutes prior to the solid form of 4-OH-DIPT hemi-glutarate hydrochloride disclosed herein, including those described in Table 5. In some embodiments, the serotonin receptor modulator is risperidone, wherein the risperidone is administered to pretreat at least 300 minutes prior to the solid form of 4-OH-DIPT hemi-glutarate hydrochloride disclosed herein, including those described in Table 5. In some embodiments, the serotonin receptor modulator is risperidone, wherein the risperidone is administered to pretreat at least 330 minutes prior to the solid form of 4-OH-DIPT hemi-glutarate hydrochloride disclosed herein, including those described in Table 5. In some embodiments, the serotonin receptor modulator is risperidone, wherein the risperidone is administered to pretreat at least 360 minutes prior to the solid form of 4-OH-DIPT hemi-glutarate hydrochloride disclosed herein, including those described in Table 5. In some preferred embodiments, the serotonin receptor modulator is risperidone, wherein risperidone is administered to pretreat between about 60 minutes and about 180 minutes prior to the administration of the solid form of 4-OH-DIPT hemi-glutarate hydrochloride disclosed herein, including those described in Table 5.

In some embodiments, the serotonin receptor modulator is quetiapine, wherein the quetiapine is administered to pretreat at least 15 minutes prior to the administration of the solid form of 4-OH-DIPT hemi-glutarate hydrochloride disclosed herein, including those described in Table 5. In some embodiments, the serotonin receptor modulator is quetiapine, wherein the quetiapine is administered to pretreat at least 30 minutes prior to the solid form of 4-OH-DIPT hemi-glutarate hydrochloride disclosed herein, including those described in Table 5. In some embodiments, the serotonin receptor modulator is quetiapine, wherein the quetiapine is administered to pretreat between at least 60 minutes and 240 minutes prior to the administration or release of the solid form of 4-OH-DIPT hemi-glutarate hydrochloride disclosed herein, including those described in Table 5. In some embodiments, the serotonin receptor modulator is quetiapine, wherein the quetiapine is administered to pretreat at least 90 minutes prior to the solid form of 4-OH-DIPT hemi-glutarate hydrochloride disclosed herein, including those described in Table 5. In some embodiments, the serotonin receptor modulator is quetiapine, wherein the quetiapine is administered to pretreat at least 120 minutes prior to the solid form of 4-OH-DIPT hemi-glutarate hydrochloride disclosed herein, including those described in Table 5. In some embodiments, the serotonin receptor modulator is quetiapine, wherein the quetiapine is administered to pretreat at least 150 minutes prior to the solid form of 4-OH-DIPT hemi-glutarate hydrochloride disclosed herein, including those described in Table 5. In some embodiments, the serotonin receptor modulator is quetiapine, wherein the quetiapine is administered to pretreat between about 15 minutes and about 150 minutes prior to the solid form of 4-OH-DIPT hemi-glutarate hydrochloride disclosed herein, including those described in Table 5. In some embodiments, the serotonin receptor modulator is quetiapine, wherein the quetiapine is administered to pretreat at least 180 minutes prior to the solid form of 4-OH-DIPT hemi-glutarate hydrochloride disclosed herein, including those described in Table 5. In some embodiments, the serotonin receptor modulator is quetiapine, wherein the quetiapine is administered to pretreat at least 210 minutes prior to the solid form of 4-OH-DIPT hemi-glutarate hydrochloride disclosed herein, including those described in Table 5.

In some embodiments, the serotonin receptor modulator is quetiapine, wherein the quetiapine is administered to pretreat at least 240 minutes prior to the solid form of 4-OH-DIPT hemi-glutarate hydrochloride disclosed herein, including those described in Table 5. In some embodiments, the serotonin receptor modulator is quetiapine, wherein the quetiapine is administered to pretreat at least 270 minutes prior to the solid form of 4-OH-DIPT hemi-glutarate hydrochloride disclosed herein, including those described in Table 5. In some embodiments, the serotonin receptor modulator is quetiapine, wherein the quetiapine is administered to pretreat at least 300 minutes prior to the solid form of 4-OH-DIPT hemi-glutarate hydrochloride disclosed herein, including those described in Table 5. In some embodiments, the serotonin receptor modulator is quetiapine, wherein the quetiapine is administered to pretreat at least 330 minutes prior to the solid form of 4-OH-DIPT hemi-glutarate hydrochloride disclosed herein, including those described in Table 5. In some embodiments, the serotonin receptor modulator is quetiapine, wherein the quetiapine is administered to pretreat at least 360 minutes prior to the solid form of 4-OH-DIPT hemi-glutarate hydrochloride disclosed herein, including those described in Table 5. In some preferred embodiments, the serotonin receptor modulator is quetiapine, wherein quetiapine is administered to pretreat between about 60 minutes and about 180 minutes prior to the administration of the solid form of 4-OH-DIPT hemi-glutarate hydrochloride disclosed herein, including those described in Table 5. In certain embodiments, such as those described above a solid form of 4-OH-DIPT hemi-glutarate hydrochloride disclosed herein, including those described in Table 5 is co-administered with a serotonin receptor modulator in the same or in separate compositions. In one embodiment, the serotonin receptor modulator is administered after the solid form of 4-OH-DIPT hemi-glutarate hydrochloride disclosed herein, including those described in Table 5. In one embodiment, the solid form of 4-OH-DIPT hemi-glutarate hydrochloride disclosed herein, including those described in Table 5 is administered in a modified release formulation such that the subject is effectively post-treated with serotonin receptor modulator post to release of an effective amount of the 4-OH-DIPT hemi-glutarate hydrochloride. In some embodiments, the serotonin receptor modulator is part of a single fixed dose formulation that releases the 4-OH-DIPT hemi-glutarate hydrochloride first followed by serotonin receptor modulator on two different release profiles. In another embodiment, the solid form of 4-OH-DIPT hemi-glutarate hydrochloride disclosed herein, including those described in Table 5 is administered first as a single dosage and, after a length of time, serotonin receptor modulator is administered as a second dosage separate from the first dosage. Thus, in some embodiments, the serotonin receptor modulator is administered or released from a composition provided herein after the administration and/or release of the 4-OH-DIPT hemi-glutarate hydrochloride form disclosed herein, including those described in Table 5. This allows post-treatment to attenuate activation of the serotonin receptor by the 4-OH-DIPT hemi-glutarate hydrochloride form disclosed herein, including those described in Table 5.

In some embodiments, the serotonin receptor modulator is administered or released from the composition provided herein to post-treat a subject by at least about at about 5 minutes, 10 minutes, 20 minutes, 30 minutes, 40 minutes, 50 minutes, 1 hour, 1.25 hours, 1.5 hours, 2 hours, or 3 hours after the release of the solid form of 4-OH-DIPT hemi-glutarate hydrochloride disclosed herein, including those described in Table 5. In some embodiments, the serotonin receptor modulator attenuates the activation of the serotonin receptor when the serotonin receptor modulator is used to post-treat at most about 3 hours, 4 hours, 5 hours, 6 hours, 7 hours, 8 hours, 9 hours, or more than 9 hours after the release of the psychedelic. In some embodiments, the serotonin receptor modulator attenuates the activation of the serotonin receptor when the serotonin receptor modulator is used to post-treat in a range of about 5 minutes to about 3 hours, about 10 minutes to about 3 hours, about 20 minutes to about 3 hours, about 30 minutes to about 3 hours, about 40 minutes to about 3 hours, about 50 minutes to about 3 hours, about 1 hour to about 3 hours, about 5 minutes to about 2 hours, about 10 minutes to about 2 hours, about 20 minutes to about 2 hours, about 30 minutes to about 2 hours, about 40 minutes to about 2 hours, about 50 minutes to about 2 hours, about 1 hour to about 2 hours, about 5 minutes to about 1 hour, about 10 minutes to about 1 hour, about 20 minutes to about 1 hour, about 30 minutes to about 1 hour, about 40 minutes to about 1 hour, or about 50 minutes to about 1 hour after the release of the psychedelic.

In a preferred embodiment, the serotonin receptor modulator is administered at about 1 hour to about 3 hours after the administration of the psychedelic.

In some embodiments, the serotonin receptor modulator is eplivanserin, wherein the eplivanserin is administered to post-treat at least 15 minutes after the administration of the solid form of 4-OH-DIPT hemi-glutarate hydrochloride disclosed herein, including those described in Table 5. In some embodiments, the serotonin receptor modulator is eplivanserin, wherein the eplivanserin is administered to post-treat between at least 30 minutes after and 360 minutes after the release or administration of the solid form of 4-OH-DIPT hemi-glutarate hydrochloride disclosed herein, including those described in Table 5. In some embodiments, the serotonin receptor modulator is eplivanserin, wherein the eplivanserin is administered to post-treat between at least 60 minutes after and 360 minutes after the release or administration the solid form of 4-OH-DIPT hemi-glutarate hydrochloride disclosed herein, including those described in Table 5. In some embodiments, the serotonin receptor modulator is eplivanserin, wherein the eplivanserin is administered to post-treat between at least 90 minutes and 240 minutes after the solid form of 4-OH-DIPT hemi-glutarate hydrochloride disclosed herein, including those described in Table 5. In some embodiments, the serotonin receptor modulator is eplivanserin, wherein the eplivanserin is administered to post-treat at least 120 minutes after the solid form of 4-OH-DIPT hemi-glutarate hydrochloride disclosed herein, including those described in Table 5.

In some embodiments, the serotonin receptor modulator is eplivanserin, wherein the eplivanserin is administered to post-treat at least 150 minutes after the solid form of 4-OH-DIPT hemi-glutarate hydrochloride disclosed herein, including those described in Table 5. In some embodiments, the serotonin receptor modulator is eplivanserin, wherein the eplivanserin is administered to post-treat between about 15 minutes and about 150 minutes after the solid form of 4-OH-DIPT hemi-glutarate hydrochloride disclosed herein, including those described in Table 5. In some embodiments, the serotonin receptor modulator is eplivanserin, wherein the eplivanserin is administered to post-treat at least 180 minutes after the solid form of 4-OH-DIPT hemi-glutarate hydrochloride disclosed herein, including those described in Table 5. In some embodiments, the serotonin receptor modulator is eplivanserin, wherein the eplivanserin is administered to post-treat at least 210 minutes after the solid form of 4-OH-DIPT hemi-glutarate hydrochloride disclosed herein, including those described in Table 5. In some embodiments, the serotonin receptor modulator is eplivanserin, wherein the eplivanserin is administered to post-treat at least 240 minutes after the solid form of 4-OH-DIPT hemi-glutarate hydrochloride disclosed herein, including those described in Table 5.

In some embodiments, the serotonin receptor modulator is eplivanserin, wherein the eplivanserin is administered to post-treat at least 270 minutes after the solid form of 4-OH-DIPT hemi-glutarate hydrochloride disclosed herein, including those described in Table 5. In some embodiments, the serotonin receptor modulator is eplivanserin, wherein the eplivanserin is administered to post-treat at least 300 minutes after the solid form of 4-OH-DIPT hemi-glutarate hydrochloride disclosed herein, including those described in Table 5. In some embodiments, the serotonin receptor modulator is eplivanserin, wherein the eplivanserin is administered to post-treat at least 330 minutes after the solid form of 4-OH-DIPT hemi-glutarate hydrochloride disclosed herein, including those described in Table 5. In some embodiments, the serotonin receptor modulator is eplivanserin, wherein the eplivanserin is administered to post-treat at least 360 minutes after administration or release of the solid form of 4-OH-DIPT hemi-glutarate hydrochloride disclosed herein, including those described in Table 5.

In some preferred embodiments, the serotonin receptor modulator is eplivanserin, wherein eplivanserin is administered to post-treat between about 60 minutes and about 180 minutes after the administration or release of the solid form of 4-OH-DIPT hemi-glutarate hydrochloride disclosed herein, including those described in Table 5.

In some embodiments, the serotonin receptor modulator is volinanserin, wherein the volinanserin is administered to post-treat a subject between at least 15 minutes and 360 minutes after the administration or release of the solid form of 4-OH-DIPT hemi-glutarate hydrochloride disclosed herein, including those described in Table 5. In some embodiments, the serotonin receptor modulator is volinanserin, wherein the volinanserin is administered to post-treat between at least 30 minutes and 360 minutes after the administration or release of the solid form of 4-OH-DIPT hemi-glutarate hydrochloride disclosed herein, including those described in Table 5. In some embodiments, the serotonin receptor modulator is volinanserin, wherein the volinanserin is administered to post-treat between at least 60 minutes and 240 minutes after the administration or release of the solid form of 4-OH-DIPT hemi-glutarate hydrochloride disclosed herein, including those described in Table 5. In some embodiments, the serotonin receptor modulator is volinanserin, wherein the volinanserin is administered to post-treat at least 90 minutes after solid form of 4-OH-DIPT hemi-glutarate hydrochloride disclosed herein, including those described in Table 5. In some embodiments, the serotonin receptor modulator is volinanserin, wherein the volinanserin is administered to post-treat at least 120 minutes after the solid form of 4-OH-DIPT hemi-glutarate hydrochloride disclosed herein, including those described in Table 5.

In some embodiments, the serotonin receptor modulator is volinanserin, wherein the volinanserin is administered to post-treat at least 150 minutes after the solid form of 4-OH-DIPT hemi-glutarate hydrochloride disclosed herein, including those described in Table 5. In some embodiments, the serotonin receptor modulator is volinanserin, wherein the volinanserin is administered to post-treat between about 15 minutes and about 150 minutes after the solid form of 4-OH-DIPT hemi-glutarate hydrochloride disclosed herein, including those described in Table 5. In some embodiments, the serotonin receptor modulator is volinanserin, wherein the volinanserin is administered to post-treat at least 180 minutes after the solid form of 4-OH-DIPT hemi-glutarate hydrochloride disclosed herein, including those described in Table 5. In some embodiments, the serotonin receptor modulator is volinanserin, wherein the volinanserin is administered to post-treat at least 210 minutes after the solid form of 4-OH-DIPT hemi-glutarate hydrochloride disclosed herein, including those described in Table 5. In some embodiments, the serotonin receptor modulator is volinanserin, wherein the volinanserin is administered to post-treat at least 240 minutes after the solid form of 4-OH-DIPT hemi-glutarate hydrochloride disclosed herein, including those described in Table 5. In some embodiments, the serotonin receptor modulator is volinanserin, wherein the volinanserin is administered to post-treat at least 270 minutes after the solid form of 4-OH-DIPT hemi-glutarate hydrochloride disclosed herein, including those described in Table 5. In some embodiments, the serotonin receptor modulator is volinanserin, wherein the volinanserin is administered to post-treat at least 300 minutes after the solid form of 4-OH-DIPT hemi-glutarate hydrochloride disclosed herein, including those described in Table 5. In some embodiments, the serotonin receptor modulator is volinanserin, wherein the volinanserin is administered to post-treat at least 330 minutes after solid form of 4-OH-DIPT hemi-glutarate hydrochloride disclosed herein, including those described in Table 5. In some embodiments, the serotonin receptor modulator is volinanserin, wherein the volinanserin is administered to post-treat at least 360 minutes after the solid form of 4-OH-DIPT hemi-glutarate hydrochloride disclosed herein, including those described in Table 5. In some preferred embodiments, the serotonin receptor modulator is volinanserin, wherein volinanserin is administered to post-treat between about 60 minutes and about 180 minutes after the administration of the solid form of 4-OH-DIPT hemi-glutarate hydrochloride disclosed herein, including those described in Table 5.

In some embodiments, the serotonin receptor modulator is ketanserin, wherein the ketanserin is administered to post-treat at least 15 minutes after the administration of the solid form of 4-OH-DIPT hemi-glutarate hydrochloride disclosed herein, including those described in Table 5. In some embodiments, the serotonin receptor modulator is ketanserin, wherein the ketanserin is administered to post-treat between at least 30 minutes and 360 minutes after the administration or release of the solid form of 4-OH-DIPT hemi-glutarate hydrochloride disclosed herein, including those described in Table 5. In some embodiments, the serotonin receptor modulator is ketanserin, wherein the ketanserin is administered to post-treat between at least 60 minutes and 240 minutes after the administration or release of the solid form of 4-OH-DIPT hemi-glutarate hydrochloride disclosed herein, including those described in Table 5. In some embodiments, the serotonin receptor modulator is ketanserin, wherein the ketanserin is administered to post-treat at least 90 minutes after the solid form of 4-OH-DIPT hemi-glutarate hydrochloride disclosed herein, including those described in Table 5. In some embodiments, the serotonin receptor modulator is ketanserin, wherein the ketanserin is administered to post-treat at least 120 minutes after the solid form of 4-OH-DIPT hemi-glutarate hydrochloride disclosed herein, including those described in Table 5. In some embodiments, the serotonin receptor modulator is ketanserin, wherein the ketanserin is administered to post-treat at least 150 minutes after the solid form of 4-OH-DIPT hemi-glutarate hydrochloride disclosed herein, including those described in Table 5. In some embodiments, the serotonin receptor modulator is ketanserin, wherein the ketanserin is administered to post-treat between about 15 minutes and about 150 minutes after the solid form of 4-OH-DIPT hemi-glutarate hydrochloride disclosed herein, including those described in Table 5. In some embodiments, the serotonin receptor modulator is ketanserin, wherein the ketanserin is administered to post-treat at least 180 minutes after the solid form of 4-OH-DIPT hemi-glutarate hydrochloride disclosed herein, including those described in Table 5. In some embodiments, the serotonin receptor modulator is ketanserin, wherein the ketanserin is administered to post-treat at least 210 minutes after the solid form of 4-OH-DIPT hemi-glutarate hydrochloride disclosed herein, including those described in Table 5. In some embodiments, the serotonin receptor modulator is ketanserin, wherein the ketanserin is administered to post-treat at least 240 minutes after the solid form of 4-OH-DIPT hemi-glutarate hydrochloride disclosed herein, including those described in Table 5. In some embodiments, the serotonin receptor modulator is ketanserin, wherein the ketanserin is administered to post-treat at least 270 minutes after the solid form of 4-OH-DIPT hemi-glutarate hydrochloride disclosed herein, including those described in Table 5. In some embodiments, the serotonin receptor modulator is ketanserin, wherein the ketanserin is administered to post-treat at least 300 minutes after the solid form of 4-OH-DIPT hemi-glutarate hydrochloride disclosed herein, including those described in Table 5. In some embodiments, the serotonin receptor modulator is ketanserin, wherein the ketanserin is administered to post-treat at least 330 minutes after the solid form of 4-OH-DIPT hemi-glutarate hydrochloride disclosed herein, including those described in Table 5. In some embodiments, the serotonin receptor modulator is ketanserin, wherein the ketanserin is administered to post-treat at least 360 minutes after the solid form of 4-OH-DIPT hemi-glutarate hydrochloride disclosed herein, including those described in Table 5. In some preferred embodiments, the serotonin receptor modulator is ketanserin, wherein ketanserin is administered to post-treat between about 60 minutes and about 180 minutes after the administration of the solid form of 4-OH-DIPT hemi-glutarate hydrochloride disclosed herein, including those described in Table 5.

In some embodiments, the serotonin receptor modulator is ritanserin, wherein the ritanserin is administered to post-treat at least 15 minutes after the administration of the solid form of 4-OH-DIPT hemi-glutarate hydrochloride disclosed herein, including those described in Table 5. In some embodiments, the serotonin receptor modulator is ritanserin, wherein the ritanserin is administered to post-treat at least 30 minutes after the solid form of 4-OH-DIPT hemi-glutarate hydrochloride disclosed herein, including those described in Table 5. In some embodiments, the serotonin receptor modulator is ritanserin wherein the ritanserin is administered to post-treat between at least 60 minutes and 240 minutes after the administration or release of the solid form of 4-OH-DIPT hemi-glutarate hydrochloride disclosed herein, including those described in Table 5. In some embodiments, the serotonin receptor modulator is ritanserin, wherein the ritanserin is administered to post-treat at least 90 minutes after the solid form of 4-OH-DIPT hemi-glutarate hydrochloride disclosed herein, including those described in Table 5. In some embodiments, the serotonin receptor modulator is ritanserin, wherein the ritanserin is administered to post-treat at least 120 minutes after the solid form of 4-OH-DIPT hemi-glutarate hydrochloride disclosed herein, including those described in Table 5. In some embodiments, the serotonin receptor modulator is ritanserin, wherein the ritanserin is administered to post-treat at least 150 minutes after the solid form of 4-OH-DIPT hemi-glutarate hydrochloride disclosed herein, including those described in Table 5. In some embodiments, the serotonin receptor modulator is ritanserin, wherein the ritanserin is administered to post-treat between about 15 minutes and about 150 minutes after the solid form of 4-OH-DIPT hemi-glutarate hydrochloride disclosed herein, including those described in Table 5. In some embodiments, the serotonin receptor modulator is ritanserin, wherein the ritanserin is administered to post-treat at least 180 minutes after the solid form of 4-OH-DIPT hemi-glutarate hydrochloride disclosed herein, including those described in Table 5. In some embodiments, the serotonin receptor modulator is ritanserin, wherein the ritanserin is administered to post-treat at least 210 minutes after the solid form of 4-OH-DIPT hemi-glutarate hydrochloride disclosed herein, including those described in Table 5. In some embodiments, the serotonin receptor modulator is ritanserin, wherein the ritanserin is administered to post-treat at least 240 minutes after the solid form of 4-OH-DIPT hemi-glutarate hydrochloride disclosed herein, including those described in Table 5. In some embodiments, the serotonin receptor modulator is ritanserin, wherein the ritanserin is administered to post-treat at least 270 minutes after the solid form of 4-OH-DIPT hemi-glutarate hydrochloride disclosed herein, including those described in Table 5. In some embodiments, the serotonin receptor modulator is ritanserin, wherein the ritanserin is administered to post-treat at least 300 minutes after the solid form of 4-OH-DIPT hemi-glutarate hydrochloride disclosed herein, including those described in Table 5. In some embodiments, the serotonin receptor modulator is ritanserin, wherein the ritanserin is administered to post-treat at least 330 minutes after the solid form of 4-OH-DIPT hemi-glutarate hydrochloride disclosed herein, including those described in Table 5. In some embodiments, the serotonin receptor modulator is ritanserin, wherein the ritanserin is administered to post-treat at least 360 minutes after the solid form of 4-OH-DIPT hemi-glutarate hydrochloride disclosed herein, including those described in Table 5. In some preferred embodiments, the serotonin receptor modulator is ritanserin, wherein ritanserin is administered to post-treat between about 60 minutes and about 180 minutes after the administration of the solid form of 4-OH-DIPT hemi-glutarate hydrochloride disclosed herein, including those described in Table 5.

In some embodiments, the serotonin receptor modulator is pimavanserin, wherein the pimavanserin is administered to post-treat at least 15 minutes after the administration of the solid form of 4-OH-DIPT hemi-glutarate hydrochloride disclosed herein, including those described in Table 5. In some embodiments, the serotonin receptor modulator is pimavanserin, wherein the pimavanserin is administered to post-treat at least 30 minutes after the solid form of 4-OH-DIPT hemi-glutarate hydrochloride disclosed herein, including those described in Table 5. In some embodiments, the serotonin receptor modulator is pimavanserin, wherein the pimavanserin is administered to post-treat between at least 60 minutes and 240 minutes after the administration or release of the solid form of 4-OH-DIPT hemi-glutarate hydrochloride disclosed herein, including those described in Table 5. In some embodiments, the serotonin receptor modulator is pimavanserin, wherein the pimavanserin is administered to post-treat at least 90 minutes after the solid form of 4-OH-DIPT hemi-glutarate hydrochloride disclosed herein, including those described in Table 5. In some embodiments, the serotonin receptor modulator is pimavanserin, wherein the pimavanserin is administered to post-treat at least 120 minutes after the solid form of 4-OH-DIPT hemi-glutarate hydrochloride disclosed herein, including those described in Table 5. In some embodiments, the serotonin receptor modulator is pimavanserin, wherein the pimavanserin is administered to post-treat at least 150 minutes after the solid form of 4-OH-DIPT hemi-glutarate hydrochloride disclosed herein, including those described in Table 5. In some embodiments, the serotonin receptor modulator is pimavanserin, wherein the pimavanserin is administered to post-treat between about 15 minutes and about 150 minutes after the solid form of 4-OH-DIPT hemi-glutarate hydrochloride disclosed herein, including those described in Table 5. In some embodiments, the serotonin receptor modulator is pimavanserin, wherein the pimavanserin is administered to post-treat at least 180 minutes after the solid form of 4-OH-DIPT hemi-glutarate hydrochloride disclosed herein, including those described in Table 5. In some embodiments, the serotonin receptor modulator is pimavanserin, wherein the pimavanserin is administered to post-treat at least 210 minutes after the solid form of 4-OH-DIPT hemi-glutarate hydrochloride disclosed herein, including those described in Table 5. In some embodiments, the serotonin receptor modulator is pimavanserin, wherein the pimavanserin is administered to post-treat at least 240 minutes after the solid form of 4-OH-DIPT hemi-glutarate hydrochloride disclosed herein, including those described in Table 5. In some embodiments, the serotonin receptor modulator is pimavanserin, wherein the pimavanserin is administered to post-treat at least 270 minutes after the solid form of 4-OH-DIPT hemi-glutarate hydrochloride disclosed herein, including those described in Table 5. In some embodiments, the serotonin receptor modulator is pimavanserin, wherein the pimavanserin is administered to post-treat at least 300 minutes after the solid form of 4-OH-DIPT hemi-glutarate hydrochloride disclosed herein, including those described in Table 5. In some embodiments, the serotonin receptor modulator is pimavanserin, wherein the pimavanserin is administered to post-treat at least 330 minutes after the solid form of 4-OH-DIPT hemi-glutarate hydrochloride disclosed herein, including those described in Table 5. In some embodiments, the serotonin receptor modulator is pimavanserin, wherein the pimavanserin is administered to post-treat at least 360 minutes after the solid form of 4-OH-DIPT hemi-glutarate hydrochloride disclosed herein, including those described in Table 5. In some preferred embodiments, the serotonin receptor modulator is pimavanserin, wherein pimavanserin is administered to post-treat between about 60 minutes and about 180 minutes after the administration of the solid form of 4-OH-DIPT hemi-glutarate hydrochloride disclosed herein, including those described in Table 5.

In some embodiments, the serotonin receptor modulator is nelotanserin, wherein the nelotanserin is administered to post-treat at least 15 minutes after the administration of the solid form of 4-OH-DIPT hemi-glutarate hydrochloride disclosed herein, including those described in Table 5. In some embodiments, the serotonin receptor modulator is nelotanserin, wherein the nelotanserin is administered to post-treat at least 30 minutes after the solid form of 4-OH-DIPT hemi-glutarate hydrochloride disclosed herein, including those described in Table 5. In some embodiments, the serotonin receptor modulator is nelotanserin, wherein the nelotanserin is administered to post-treat between at least 60 minutes and 240 minutes after the administration or release of the solid form of 4-OH-DIPT hemi-glutarate hydrochloride disclosed herein, including those described in Table 5. In some embodiments, the serotonin receptor modulator is nelotanserin, wherein the nelotanserin is administered to post-treat at least 90 minutes after the solid form of 4-OH-DIPT hemi-glutarate hydrochloride disclosed herein, including those described in Table 5. In some embodiments, the serotonin receptor modulator is nelotanserin, wherein the nelotanserin is administered to post-treat at least 120 minutes after the solid form of 4-OH-DIPT hemi-glutarate hydrochloride disclosed herein, including those described in Table 5.

In some embodiments, the serotonin receptor modulator is nelotanserin, wherein the nelotanserin is administered to post-treat at least 150 minutes after the solid form of 4-OH-DIPT hemi-glutarate hydrochloride disclosed herein, including those described in Table 5. In some embodiments, the serotonin receptor modulator is nelotanserin, wherein the nelotanserin is administered to post-treat between about 15 minutes and about 150 minutes after the solid form of 4-OH-DIPT hemi-glutarate hydrochloride disclosed herein, including those described in Table 5. In some embodiments, the serotonin receptor modulator is nelotanserin, wherein the nelotanserin is administered to post-treat at least 180 minutes after the solid form of 4-OH-DIPT hemi-glutarate hydrochloride disclosed herein, including those described in Table 5. In some embodiments, the serotonin receptor modulator is nelotanserin, wherein the nelotanserin is administered to post-treat at least 210 minutes after the solid form of 4-OH-DIPT hemi-glutarate hydrochloride disclosed herein, including those described in Table 5. In some embodiments, the serotonin receptor modulator is nelotanserin, wherein the nelotanserin is administered to post-treat at least 240 minutes after the solid form of 4-OH-DIPT hemi-glutarate hydrochloride disclosed herein, including those described in Table 5. In some embodiments, the serotonin receptor modulator is nelotanserin, wherein the nelotanserin is administered to post-treat at least 270 minutes after the solid form of 4-OH-DIPT hemi-glutarate hydrochloride disclosed herein, including those described in Table 5.

In some embodiments, the serotonin receptor modulator is nelotanserin, wherein the nelotanserin is administered to post-treat at least 300 minutes after the solid form of 4-OH-DIPT hemi-glutarate hydrochloride disclosed herein, including those described in Table 5. In some embodiments, the serotonin receptor modulator is nelotanserin, wherein the nelotanserin is administered to post-treat at least 330 minutes after the solid form of 4-OH-DIPT hemi-glutarate hydrochloride disclosed herein, including those described in Table 5. In some embodiments, the serotonin receptor modulator is nelotanserin, wherein the nelotanserin is administered to post-treat at least 360 minutes after the solid form of 4-OH-DIPT hemi-glutarate hydrochloride disclosed herein, including those described in Table 5. In some preferred embodiments, the serotonin receptor modulator is nelotanserin, wherein nelotanserin is administered to post-treat between about 60 minutes and about 180 minutes after the administration of the solid form of 4-OH-DIPT hemi-glutarate hydrochloride disclosed herein, including those described in Table 5.

In some embodiments, the serotonin receptor modulator is pruvanserin, wherein the pruvanserin is administered to post-treat at least 15 minutes after the administration of the solid form of 4-OH-DIPT hemi-glutarate hydrochloride disclosed herein, including those described in Table 5. In some embodiments, the serotonin receptor modulator is pruvanserin, wherein the pruvanserin is administered to post-treat at least 30 minutes after the solid form of 4-OH-DIPT hemi-glutarate hydrochloride disclosed herein, including those described in Table 5. In some embodiments, the serotonin receptor modulator is pruvanserin, wherein the pruvanserin is administered to post-treat between at least 60 minutes and 240 minutes after the administration or release of the solid form of 4-OH-DIPT hemi-glutarate hydrochloride disclosed herein, including those described in Table 5. In some embodiments, the serotonin receptor modulator is pruvanserin, wherein the pruvanserin is administered to post-treat at least 90 minutes after the solid form of 4-OH-DIPT hemi-glutarate hydrochloride disclosed herein, including those described in Table 5. In some embodiments, the serotonin receptor modulator is pruvanserin, wherein the pruvanserin is administered to post-treat at least 120 minutes after the solid form of 4-OH-DIPT hemi-glutarate hydrochloride disclosed herein, including those described in Table 5. In some embodiments, the serotonin receptor modulator is pruvanserin, wherein the pruvanserin is administered to post-treat at least 150 minutes after the solid form of 4-OH-DIPT hemi-glutarate hydrochloride disclosed herein, including those described in Table 5. In some embodiments, the serotonin receptor modulator is pruvanserin, wherein the pruvanserin is administered to post-treat between about 15 minutes and about 150 minutes after the solid form of 4-OH-DIPT hemi-glutarate hydrochloride disclosed herein, including those described in Table 5. In some embodiments, the serotonin receptor modulator is pruvanserin, wherein the pruvanserin is administered to post-treat at least 180 minutes after the solid form of 4-OH-DIPT hemi-glutarate hydrochloride disclosed herein, including those described in Table 5. In some embodiments, the serotonin receptor modulator is pruvanserin, wherein the pruvanserin is administered to post-treat at least 210 minutes after the solid form of 4-OH-DIPT hemi-glutarate hydrochloride disclosed herein, including those described in Table 5.

In some embodiments, the serotonin receptor modulator is pruvanserin, wherein the pruvanserin is administered to post-treat at least 240 minutes after the solid form of 4-OH-DIPT hemi-glutarate hydrochloride disclosed herein, including those described in Table 5. In some embodiments, the serotonin receptor modulator is pruvanserin, wherein the pruvanserin is administered to post-treat at least 270 minutes after the solid form of 4-OH-DIPT hemi-glutarate hydrochloride disclosed herein, including those described in Table 5. In some embodiments, the serotonin receptor modulator is pruvanserin, wherein the pruvanserin is administered to post-treat at least 300 minutes after the solid form of 4-OH-DIPT hemi-glutarate hydrochloride disclosed herein, including those described in Table 5. In some embodiments, the serotonin receptor modulator is pruvanserin, wherein the pruvanserin is administered to post-treat at least 330 minutes after the solid form of 4-OH-DIPT hemi-glutarate hydrochloride disclosed herein, including those described in Table 5. In some embodiments, the serotonin receptor modulator is pruvanserin, wherein the pruvanserin is administered to post-treat at least 360 minutes after the solid form of 4-OH-DIPT hemi-glutarate hydrochloride disclosed herein, including those described in Table 5. In some preferred embodiments, the serotonin receptor modulator is pruvanserin, wherein pruvanserin is administered to post-treat between about 60 minutes and about 180 minutes after the administration of the solid form of 4-OH-DIPT hemi-glutarate hydrochloride disclosed herein, including those described in Table 5.

In some embodiments, the serotonin receptor modulator is flibanserin, wherein the flibanserin is administered to post-treat at least 15 minutes post to the administration of the solid form of 4-OH-DIPT hemi-glutarate hydrochloride disclosed herein, including those described in Table 5. In some embodiments, the serotonin receptor modulator is flibanserin, wherein the flibanserin is administered to post-treat at least 30 minutes post to the solid form of 4-OH-DIPT hemi-glutarate hydrochloride disclosed herein, including those described in Table 5. In some embodiments, the serotonin receptor modulator is flibanserin, wherein the flibanserin is administered to post-treat between at least 60 minutes and 240 minutes post to the administration or release of the solid form of 4-OH-DIPT hemi-glutarate hydrochloride disclosed herein, including those described in Table 5. In some embodiments, the serotonin receptor modulator is flibanserin, wherein the flibanserin is administered to post-treat at least 90 minutes post to the solid form of 4-OH-DIPT hemi-glutarate hydrochloride disclosed herein, including those described in Table 5. In some embodiments, the serotonin receptor modulator is flibanserin, wherein the flibanserin is administered to post-treat at least 120 minutes post to the solid form of 4-OH-DIPT hemi-glutarate hydrochloride disclosed herein, including those described in Table 5. In some embodiments, the serotonin receptor modulator is flibanserin, wherein the flibanserin is administered to post-treat at least 150 minutes post to the solid form of 4-OH-DIPT hemi-glutarate hydrochloride disclosed herein, including those described in Table 5. In some embodiments, the serotonin receptor modulator is flibanserin, wherein the flibanserin is administered to post-treat between about 15 minutes and about 150 minutes post to the solid form of 4-OH-DIPT hemi-glutarate hydrochloride disclosed herein, including those described in Table 5. In some embodiments, the serotonin receptor modulator is flibanserin, wherein the flibanserin is administered to post-treat at least 180 minutes post to the solid form of 4-OH-DIPT hemi-glutarate hydrochloride disclosed herein, including those described in Table 5. In some embodiments, the serotonin receptor modulator is flibanserin, wherein the flibanserin is administered to post-treat at least 210 minutes post to the solid form of 4-OH-DIPT hemi-glutarate hydrochloride disclosed herein, including those described in Table 5.

In some embodiments, the serotonin receptor modulator is flibanserin, wherein the flibanserin is administered to post-treat at least 240 minutes post to the solid form of 4-OH-DIPT hemi-glutarate hydrochloride disclosed herein, including those described in Table 5. In some embodiments, the serotonin receptor modulator is flibanserin, wherein the flibanserin is administered to post-treat at least 270 minutes post to the solid form of 4-OH-DIPT hemi-glutarate hydrochloride disclosed herein, including those described in Table 5. In some embodiments, the serotonin receptor modulator is flibanserin, wherein the flibanserin is administered to post-treat at least 300 minutes post to the solid form of 4-OH-DIPT hemi-glutarate hydrochloride disclosed herein, including those described in Table 5. In some embodiments, the serotonin receptor modulator is flibanserin, wherein the flibanserin is administered to post-treat at least 330 minutes post to the solid form of 4-OH-DIPT hemi-glutarate hydrochloride disclosed herein, including those described in Table 5. In some embodiments, the serotonin receptor modulator is flibanserin, wherein the flibanserin is administered to post-treat at least 360 minutes post to the solid form of 4-OH-DIPT hemi-glutarate hydrochloride disclosed herein, including those described in Table 5. In some preferred embodiments, the serotonin receptor modulator is flibanserin, wherein flibanserin is administered to post-treat between about 60 minutes and about 180 minutes post to the administration of the solid form of 4-OH-DIPT hemi-glutarate hydrochloride disclosed herein, including those described in Table 5.

In some embodiments, the serotonin receptor modulator is olanzapine, wherein the olanzapine is administered to post-treat at least 15 minutes post to the administration of the solid form of 4-OH-DIPT hemi-glutarate hydrochloride disclosed herein, including those described in Table 5. In some embodiments, the serotonin receptor modulator is olanzapine, wherein the olanzapine is administered to post-treat at least 30 minutes post to the solid form of 4-OH-DIPT hemi-glutarate hydrochloride disclosed herein, including those described in Table 5. In some embodiments, the serotonin receptor modulator is olanzapine, wherein the olanzapine is administered to post-treat between at least 60 minutes and 240 minutes post to the administration or release of the solid form of 4-OH-DIPT hemi-glutarate hydrochloride disclosed herein, including those described in Table 5. In some embodiments, the serotonin receptor modulator is olanzapine, wherein the olanzapine is administered to post-treat at least 90 minutes post to the solid form of 4-OH-DIPT hemi-glutarate hydrochloride disclosed herein, including those described in Table 5. In some embodiments, the serotonin receptor modulator is olanzapine, wherein the olanzapine is administered to post-treat at least 120 minutes post to the solid form of 4-OH-DIPT hemi-glutarate hydrochloride disclosed herein, including those described in Table 5. In some embodiments, the serotonin receptor modulator is olanzapine, wherein the olanzapine is administered to post-treat at least 150 minutes post to the solid form of 4-OH-DIPT hemi-glutarate hydrochloride disclosed herein, including those described in Table 5. In some embodiments, the serotonin receptor modulator is olanzapine, wherein the olanzapine is administered to post-treat between about 15 minutes and about 150 minutes post to the solid form of 4-OH-DIPT hemi-glutarate hydrochloride disclosed herein, including those described in Table 5. In some embodiments, the serotonin receptor modulator is olanzapine, wherein the olanzapine is administered to post-treat at least 180 minutes post to the solid form of 4-OH-DIPT hemi-glutarate hydrochloride disclosed herein, including those described in Table 5. In some embodiments, the serotonin receptor modulator is olanzapine, wherein the olanzapine is administered to post-treat at least 210 minutes post to the solid form of 4-OH-DIPT hemi-glutarate hydrochloride disclosed herein, including those described in Table 5.

In some embodiments, the serotonin receptor modulator is olanzapine, wherein the olanzapine is administered to post-treat at least 240 minutes post to the solid form of 4-OH-DIPT hemi-glutarate hydrochloride disclosed herein, including those described in Table 5. In some embodiments, the serotonin receptor modulator is olanzapine, wherein the olanzapine is administered to post-treat at least 270 minutes post to the solid form of 4-OH-DIPT hemi-glutarate hydrochloride disclosed herein, including those described in Table 5. In some embodiments, the serotonin receptor modulator is olanzapine, wherein the olanzapine is administered to post-treat at least 300 minutes post to the solid form of 4-OH-DIPT hemi-glutarate hydrochloride disclosed herein, including those described in Table 5. In some embodiments, the serotonin receptor modulator is olanzapine, wherein the olanzapine is administered to post-treat at least 330 minutes post to the solid form of 4-OH-DIPT hemi-glutarate hydrochloride disclosed herein, including those described in Table 5. In some embodiments, the serotonin receptor modulator is olanzapine, wherein the olanzapine is administered to post-treat at least 360 minutes post to the solid form of 4-OH-DIPT hemi-glutarate hydrochloride disclosed herein, including those described in Table 5. In some preferred embodiments, the serotonin receptor modulator is olanzapine, wherein olanzapine is administered to post-treat between about 60 minutes and about 180 minutes post to the administration of the solid form of 4-OH-DIPT hemi-glutarate hydrochloride disclosed herein, including those described in Table 5.

In some embodiments, the serotonin receptor modulator is quetiapine, wherein the quetiapine is administered to post-treat at least 15 minutes post to the administration of the solid form of 4-OH-DIPT hemi-glutarate hydrochloride disclosed herein, including those described in Table 5. In some embodiments, the serotonin receptor modulator is quetiapine, wherein the quetiapine is administered to post-treat at least 30 minutes post to the solid form of 4-OH-DIPT hemi-glutarate hydrochloride disclosed herein, including those described in Table 5. In some embodiments, the serotonin receptor modulator is quetiapine, wherein the quetiapine is administered to post-treat between at least 60 minutes and 240 minutes post to the administration or release of the solid form of 4-OH-DIPT hemi-glutarate hydrochloride disclosed herein, including those described in Table 5. In some embodiments, the serotonin receptor modulator is quetiapine, wherein the quetiapine is administered to post-treat at least 90 minutes post to the solid form of 4-OH-DIPT hemi-glutarate hydrochloride disclosed herein, including those described in Table 5. In some embodiments, the serotonin receptor modulator is quetiapine, wherein the quetiapine is administered to post-treat at least 120 minutes post to the solid form of 4-OH-DIPT hemi-glutarate hydrochloride disclosed herein, including those described in Table 5. In some embodiments, the serotonin receptor modulator is quetiapine, wherein the quetiapine is administered to post-treat at least 150 minutes post to the solid form of 4-OH-DIPT hemi-glutarate hydrochloride disclosed herein, including those described in Table 5. In some embodiments, the serotonin receptor modulator is quetiapine, wherein the quetiapine is administered to post-treat between about 15 minutes and about 150 minutes post to the solid form of 4-OH-DIPT hemi-glutarate hydrochloride disclosed herein, including those described in Table 5. In some embodiments, the serotonin receptor modulator is quetiapine, wherein the quetiapine is administered to post-treat at least 180 minutes post to the solid form of 4-OH-DIPT hemi-glutarate hydrochloride disclosed herein, including those described in Table 5. In some embodiments, the serotonin receptor modulator is quetiapine, wherein the quetiapine is administered to post-treat at least 210 minutes post to the solid form of 4-OH-DIPT hemi-glutarate hydrochloride disclosed herein, including those described in Table 5.

In some embodiments, the serotonin receptor modulator is quetiapine, wherein the quetiapine is administered to post-treat at least 240 minutes post to the solid form of 4-OH-DIPT hemi-glutarate hydrochloride disclosed herein, including those described in Table 5. In some embodiments, the serotonin receptor modulator is quetiapine, wherein the quetiapine is administered to post-treat at least 270 minutes post to the solid form of 4-OH-DIPT hemi-glutarate hydrochloride disclosed herein, including those described in Table 5. In some embodiments, the serotonin receptor modulator is quetiapine, wherein the quetiapine is administered to post-treat at least 300 minutes post to the solid form of 4-OH-DIPT hemi-glutarate hydrochloride disclosed herein, including those described in Table 5. In some embodiments, the serotonin receptor modulator is quetiapine, wherein the quetiapine is administered to post-treat at least 330 minutes post to the solid form of 4-OH-DIPT hemi-glutarate hydrochloride disclosed herein, including those described in Table 5. In some embodiments, the serotonin receptor modulator is quetiapine, wherein the quetiapine is administered to post-treat at least 360 minutes post to the solid form of 4-OH-DIPT hemi-glutarate hydrochloride disclosed herein, including those described in Table 5. In some preferred embodiments, the serotonin receptor modulator is quetiapine, wherein quetiapine is administered to post-treat between about 60 minutes and about 180 minutes post to the administration of the solid form of 4-OH-DIPT hemi-glutarate hydrochloride disclosed herein, including those described in Table 5.

In some embodiments, the serotonin receptor modulator is risperidone, wherein the risperidone is administered to post-treat at least 15 minutes post to the administration of the solid form of 4-OH-DIPT hemi-glutarate hydrochloride disclosed herein, including those described in Table 5. In some embodiments, the serotonin receptor modulator is risperidone, wherein the risperidone is administered to post-treat at least 30 minutes post to the solid form of 4-OH-DIPT hemi-glutarate hydrochloride disclosed herein, including those described in Table 5. In some embodiments, the serotonin receptor modulator is risperidone, wherein the risperidone is administered to post-treat between at least 60 minutes and 240 minutes post to the administration or release of the solid form of 4-OH-DIPT hemi-glutarate hydrochloride disclosed herein, including those described in Table 5. In some embodiments, the serotonin receptor modulator is risperidone, wherein the risperidone is administered to post-treat at least 90 minutes post to the solid form of 4-OH-DIPT hemi-glutarate hydrochloride disclosed herein, including those described in Table 5. In some embodiments, the serotonin receptor modulator is risperidone, wherein the risperidone is administered to post-treat at least 120 minutes post to the solid form of 4-OH-DIPT hemi-glutarate hydrochloride disclosed herein, including those described in Table 5. In some embodiments, the serotonin receptor modulator is risperidone, wherein the risperidone is administered to post-treat at least 150 minutes post to the solid form of 4-OH-DIPT hemi-glutarate hydrochloride disclosed herein, including those described in Table 5. In some embodiments, the serotonin receptor modulator is risperidone, wherein the risperidone is administered to post-treat between about 15 minutes and about 150 minutes post to the solid form of 4-OH-DIPT hemi-glutarate hydrochloride disclosed herein, including those described in Table 5. In some embodiments, the serotonin receptor modulator is risperidone, wherein the risperidone is administered to post-treat at least 180 minutes post to the solid form of 4-OH-DIPT hemi-glutarate hydrochloride disclosed herein, including those described in Table 5. In some embodiments, the serotonin receptor modulator is risperidone, wherein the risperidone is administered to post-treat at least 210 minutes post to the solid form of 4-OH-DIPT hemi-glutarate hydrochloride disclosed herein, including those described in Table 5.

In some embodiments, the serotonin receptor modulator is risperidone, wherein the risperidone is administered to post-treat at least 240 minutes post to the solid form of 4-OH-DIPT hemi-glutarate hydrochloride disclosed herein, including those described in Table 5. In some embodiments, the serotonin receptor modulator is risperidone, wherein the risperidone is administered to post-treat at least 270 minutes post to the solid form of 4-OH-DIPT hemi-glutarate hydrochloride disclosed herein, including those described in Table 5. In some embodiments, the serotonin receptor modulator is risperidone, wherein the risperidone is administered to post-treat at least 300 minutes post to the solid form of 4-OH-DIPT hemi-glutarate hydrochloride disclosed herein, including those described in Table 5. In some embodiments, the serotonin receptor modulator is risperidone, wherein the risperidone is administered to post-treat at least 330 minutes post to the solid form of 4-OH-DIPT hemi-glutarate hydrochloride disclosed herein, including those described in Table 5. In some embodiments, the serotonin receptor modulator is risperidone, wherein the risperidone is administered to post-treat at least 360 minutes post to the solid form of 4-OH-DIPT hemi-glutarate hydrochloride disclosed herein, including those described in Table 5. In some preferred embodiments, the serotonin receptor modulator is risperidone, wherein risperidone is administered to post-treat between about 60 minutes and about 180 minutes post to the administration of the solid form of 4-OH-DIPT hemi-glutarate hydrochloride disclosed herein, including those described in Table 5.

EXAMPLES

Example 1

Salt Screen

4-OH-DIPT hemi-glutarate is characterized to evaluate its physical properties. The evaluation is performed by X-ray powder diffraction (XRPD), polarized light microscopy (PLM), differential scanning calorimetry (DSC), thermogravimetry (TG), dynamic vapor sorption/desorption (DVS), and/or solubility testing in organic solvents, water, and mixed solvent systems. XRPD data is used to assess crystallinity. PLM data is used to evaluate crystallinity and particle size/morphology. DSC data is used to evaluate melting point, thermal stability, and crystalline form conversion. TG data is used to evaluate if the free base is a solvate or hydrate, and to evaluate thermal stability. DVS data is used to evaluate hygroscopicity of the free base and if hydrates can be formed at high relative humidity. About 10 to 15 solvents are selected from the list below, based on their properties (polarity, dielectric constant and dipole moment).

4-OH-DIPT hemi-succinate is characterized to evaluate its physical properties. The evaluation is performed by X-ray powder diffraction (XRPD), polarized light microscopy (PLM), differential scanning calorimetry (DSC), thermogravimetry (TG), dynamic vapor sorption/desorption (DVS), and/or solubility testing in organic solvents, water, and mixed solvent systems. XRPD data is used to assess crystallinity. PLM data is used to evaluate crystallinity and particle size/morphology. DSC data is used to evaluate melting point, thermal stability, and crystalline form conversion. TG data is used to evaluate if the free base is a solvate or hydrate, and to evaluate thermal stability. DVS data is used to evaluate hygroscopicity of the free base and if hydrates can be formed at high relative humidity. About 10 to 15 solvents are selected from the list below, based on their properties (polarity, dielectric constant and dipole moment).

The active pharmaceutical ingredient (API), 4-OH-DIPT hemi-glutarate hydrochloride, is characterized to evaluate its physical properties. The evaluation is performed by X-ray powder diffraction (XRPD), polarized light microscopy (PLM), differential scanning calorimetry (DSC), thermogravimetry (TG), dynamic vapor sorption/desorption (DVS), and/or solubility testing in organic solvents, water, and mixed solvent systems. XRPD data is used to assess crystallinity. PLM data is used to evaluate crystallinity and particle size/morphology. DSC data is used to evaluate melting point, thermal stability, and crystalline form conversion. TG data is used to evaluate if the API is a solvate or hydrate, and to evaluate thermal stability. DVS data is used to evaluate hygroscopicity of the API and if hydrates can be formed at high relative humidity. About 10 to 15 solvents may be selected from the list below, based on their properties (polarity, dielectric constant and dipole moment).

TABLE 2

| Solvents | |
|---|---|
| acetic acid | n-heptane |
| Acetone | n-hexane |
| Acetonitrile | 1,1,1,3,3,3-hexafluoro-2-propanol |
| benzyl alcohol | isobutanol (2-methyl-1-propanol) |
| 1-butanol | isopentanol (3-methyl-1-butanol) |
| 2-butanol | isopropyl alcohol (2-propanol) |
| butyl acetate | isopropylbenzene (cumene) |
| t-butyl methyl ether | Methanol |
| Chlorobenzene | methoxybenzene (anisole) |
| Chloroform | methyl acetate |
| di(ethylene glycol) | methyl ethyl ketone (2-butanone ) |
| Dichloromethane | methyl isobutyl ketone |
| diethyl ether | Nitromethane |
| Diethylamine | N-methyl-2-pyrrolidone (NMP) |
| Dimethylacetamide (DMA) | 1-octanol |
| diisopropyl ether | 1-pentanol |
| N,N-dimethyl-formamide (DMF) | 1-propanol |
| dimethyl sulfoxide | Perfluorohexane |
| 1,4-dioxane | propyl acetate |
| 1,2-ethanediol (ethylene glycol) | 1,1,2,2-tetrachloroethane |
| Ethanol | Tetrahydrofuran |
| Ethanolamine | Toluene |
| 2-ethoxyethanol (Cellusolve) | 1,1,1-trichloroethane |
| ethyl acetate | 2,2,2-trifluoroethanol |
| ethyl formate | Water |
| formic acid | o-xylene (1,2-dimethylbenzene) |
| Glycerol | p-xylene (1,4-dimethylbenzene) |

The information obtained is used for designing the subsequent salt screen. The salt screen is performed by reacting the free base with pharmaceutically acceptable acids under various conditions in attempts to generate crystalline salts. Pharmaceutically acceptable acids that may be used are listed below. Specific acids are selected based on the pKa of the free base, and typically 15 to 20 acids are selected. Experiments are performed using 0.5 molar equivalent, 1 molar equivalent and/or 2 molar equivalents of the acid.

TABLE 3

| Exemplary Acids | |
|---|---|
| naphthalene-1,5-disulfonic acid | citric acid |
| sulfuric acid | d-glucuronic acid |
| ethane-1,2-disulfonic acid | lactobionic acid |
| p-toluenesulfonic acid | D-glucoheptonic acid |
| thiocyanic acid | (−)-L-pyroglutamic acid |
| methanesulfonic acid | L-malic acid |
| dodecylsulfuric acid | hippuric acid |
| naphthalene-2-sulfonic acid | D-gluconic acid |
| benzenesulfonic acid | D,L-lactic acid |
| oxalic acid | oleic acid |
| glycerophosphoric acid | succinic acid |
| ethanesulfonic acid, 2-hydroxy | glutaric acid |
| L-aspartic acid | cinnamic acid |
| maleic acid | adipic acid |
| phosphoric acid | sebacic acid |
| ethanesulfonic acid | (+)-camphoric acid |

TABLE 3-continued

| Exemplary Acids | |
|---|---|
| glutamic acid | acetic acid |
| pamoic (embonic) acid | nicotinic acid |
| glutaric acid, 2-oxo- | isobutyric acid |
| 2-naphthoic acid, 1-hydroxy | propionic acid |
| malonic acid | lauric acid |
| gentisic acid | stearic acid |
| L-tartaric acid | orotic acid |
| galactaric (mucic) acid | carbonic acid |
| Xinafoic acid | Fumaric acid |
| Hydrobromic acid | |

Solvent systems for the salt crystallization experiments are selected based on the solubility of the free base and the selected acid. Solvents are used as a single solvent or as solvent mixtures, some containing water. The techniques that are used for salt crystallization are chosen based on the solvent selected and properties of the free base. The following techniques (or combination of techniques) may be used for salt crystallization:

Free base and acid are dissolved in a solvent or mixture of solvents, and the solvents are evaporated at different rates (slow evaporation or fast evaporation) and at different temperatures (ambient or elevated).

Free base and acid are dissolved in a solvent or mixture of solvents (at ambient temperature or an elevated temperature), and the final solution is cooled to a sub-ambient temperature (between −78° C. to 15° C.). The cooling method can be a fast cooling (by plunging the sample into an ice bath or a dry ice/acetone bath), or slow cooling. The solids formed will be recovered by filtration and dried (air dried or vacuum dried).

Free base and acid are dissolved in a solvent or mixture of solvents, and an antisolvent is added to precipitate the salt. The solids formed will be recovered by filtration and dried (air dried or vacuum dried).

Free base and acid are added to a solvent or mixture of solvents, where one or both components are not fully dissolved. The slurry is agitated at different temperatures for a number of days. The solids formed will be recovered by filtration and dried (air dried or vacuum dried). The same experiment can be also performed in solvent systems where the solvents are not miscible.

Free base and acid are milled together (by mechanical milling or by mortar and pestle), with a drop of solvent, or without any solvent.

Free base and acid are melted together, and cooled to various temperatures using various cooling rates.

If an amorphous form of a salt is obtained, the amorphous salt will be exposed to elevated humidity, or elevated temperature (or combination of both), or solvent vapors at various temperatures to form crystalline salts.

The stoichiometric ratio of acid to 4-OH-DIPT hemi-glutarate is confirmed by $^1$H NMR, HPLC, or both as is known to those of ordinary skill in the art.

The stoichiometric ratio of acid to 4-OH-DIPT hemi-succinate is confirmed by $^1$H NMR, HPLC, or both as is known to those of ordinary skill in the art.

The salts obtained are analyzed by XRPD to determine if they are crystalline and, if so, by DSC to see the melting point and by TG to see if they are hydrated/solvated, and by 1H NMR spectroscopy to ensure chemical integrity. KF water titration is performed on salts that are hydrated. DVS analysis is performed to evaluate hygroscopicity of the salt and if hydrated form is present.

Example 2

Polymorph Screen

The active pharmaceutical ingredient (API), which may be a free base or a salt, is characterized to evaluate its physical properties. In some embodiments, the active pharmaceutical ingredient (API), 4-OH-DIPT hemi-succinate hydrochloride, is characterized to evaluate its physical properties. The evaluation is performed by X-ray powder diffraction (XRPD), polarized light microscopy (PLM), differential scanning calorimetry (DSC), thermogravimetry (TG), dynamic vapor sorption/desorption (DVS), and/or solubility testing in organic solvents, water, and mixed solvent systems. XRPD data is used to assess crystallinity. PLM data is used to evaluate crystallinity and particle size/morphology. DSC data is used to evaluate melting point, thermal stability, and crystalline form conversion. TG data is used to evaluate if the API is a solvate or hydrate, and to evaluate thermal stability. DVS data is used to evaluate hygroscopicity of the API and if hydrates can be formed at high relative humidity. About 10 to 15 solvents may be selected from the list below, based on their properties (polarity, dielectric constant and dipole moment).

TABLE 4

| Solvents | |
|---|---|
| acetic acid | n-heptane |
| acetone | n-hexane |
| acetonitrile | 1,1,1,3,3,3-hexafluoro-2-propanol |
| benzyl alcohol | isobutanol (2-methyl-1-propanol) |
| 1-butanol | isopentanol (3-methyl-1-butanol) |
| 2-butanol | isopropyl alcohol (2-propanol) |
| butyl acetate | isopropylbenzene (cumene) |
| t-butyl methyl ether | methanol |
| chlorobenzene | methoxybenzene (anisole) |
| chloroform | methyl acetate |
| di(ethylene glycol) | methyl ethyl ketone (2-butanone ) |
| dichloromethane | methyl isobutyl ketone |
| diethyl ether | nitromethane |
| diethylamine | N-methyl-2-pyrrolidone (NMP) |
| Dimethylacetamide (DMA) | 1-octanol |
| diisopropyl ether | 1-pentanol |
| N,N-dimethyl-formamide (DMF) | 1-propanol |
| dimethyl sulfoxide | perfluorohexane |
| 1,4-dioxane | propyl acetate |
| 1,2-ethanediol (ethylene glycol) | 1,1,2,2-tetrachloroethane |
| ethanol | tetrahydrofuran |
| ethanolamine | toluene |
| 2-ethoxyethanol (Cellusolve) | 1,1,1-trichloroethane |
| ethyl acetate | 2,2,2-trifluoroethanol |
| ethyl formate | water |
| formic acid | o-xylene (1,2-dimethylbenzene) |
| glycerol | p-xylene (1,4-dimethylbenzene) |

The information obtained is used for designing the subsequent polymorph screen. Solvents are used as a single solvent or as solvent mixtures, some containing water. The techniques used for the polymorph screen are chosen based on the solvent selected and properties of the API. The following techniques (or a combination of techniques) may be used for the polymorph screening:

- API is dissolved in a solvent or mixture of solvents, and the solvents are evaporated at different rates (slow evaporation or fast evaporation) and at different temperatures (ambient or elevated).
- API is dissolved in a solvent or mixture of solvents (at ambient temperature or an elevated temperature), and the final solution is cooled (between −78° C. to 20° C.). The cooling method can be a fast cooling (by plunging the sample to an ice bath or a dry ice/acetone bath), or slow cooling. The solids formed will be recovered by filtration and dried (air dried or vacuum dried).
- API is dissolved in a solvent or mixture of solvents, and an antisolvent is added to precipitate the salt. The solids formed will be recovered by filtration and dried (air dried or vacuum dried).
- API is added to a solvent or mixture of solvents, where the API is not fully dissolved. The slurry will be agitated at different temperatures for a number of days. The solids formed will be recovered by filtration and (air dried or vacuum dried).
- API is milled (by mechanical milling or by mortar and pestle), with a drop of solvent, or without any solvent.
- API is melted and cooled (at different cooling rates, fast and slow, and cooled to different temperatures) to obtain solids.
- API is suspended in a solvent or mixture of solvents, and the slurry is placed in a heating/cooling cycle for multiple cycles. The remaining solids after the final cooling cycle will be filtered and (air dried or vacuum dried).
- API is processed to obtain an amorphous form (by melting, milling, solvent evaporation, spray drying or lyophilization). The amorphous form will then be exposed to elevated humidity (or elevated temperature, or combination thereof), or to solvent vapors for extended period of days.
- API is exposed to elevated humidity (or elevated temperature, or combination thereof), or to solvent vapors for extended period of days.
- Two or more polymorphs of the API are mixed in a solvent or solvent systems (some solvent mixtures containing variable amount of water) to obtain a slurry, and the slurry will be agitated (at various temperatures) for an extended period of time (days). The solvent system used can be pre-saturated with the API. The final solids will be filtered and dried (air dried or vacuum dried).
- API is heated to a specific temperature and cooled (at ambient conditions or in a dry box).

The solids obtained are analyzed by XRPD to determine if they are crystalline and, if so, by DSC to see the melting point and by TG to see if they are hydrated/solvated, and by 1H NMR spectroscopy to ensure chemical integrity. KF water titration is performed on forms that are hydrated. DVS analysis is performed to evaluate hygroscopicity of the form and if hydrated form is present. In particular variable temperature analyses, including variable temperature XRPD, are performed to assess the stability of each physical form as well as its crystallinity.

Differential scanning calorimetry (DSC) thermograms are obtained using a DSC Q 100 (TA Instruments, New Castle, DE). The temperature axis and cell constant of the DSC cell are calibrated with indium (10 mg, 99.9% pure, melting point 156.6° C., heat of fusion 28.4 J/g). Samples (2.0-5.0 mg) are weighed in aluminum pans on an analytical balance. Aluminum pans without lids are used for the analysis. The samples are equilibrated at 25° C. and heated to 250-300° C. at a heating rate of 10° C./min under continuous nitrogen flow. TG analysis of the samples is performed with a Q 50 (TA Instruments, New Castle, DE). Samples (2.0-5.0 mg) are analyzed in open aluminum pans under a nitrogen flow (50 mL/min) at 25° C. to 210° C. with a heating rate of 10° C./min.

The sample for moisture analysis is allowed to dry at 25° C. for up to 4 hours under a stream of dry nitrogen. The relative humidity is then increased stepwise from 10 to 90% relative humidity (adsorption scan) allowing the sample to equilibrate for a maximum of four hours before weighing and moving on to the next step. The desorption scan is measured from 85 to 0% relative humidity with the same equilibration time. The sample is then dried under a stream of dry nitrogen at 80° C. for 2 hours or until no weight loss is observed.

X-ray powder diffraction data are collected using a Miniflex Tabletop XRD system (Rigaku/MSC, The Woodlands, TX) from 5° to 45°2θ with steps of 0.1°, and the measuring time is 1.0 second/step. All samples are ground to similar size before exposure to radiation. The powder samples are illuminated using CuKα radiation (λ=1.54056 Å) at 30 kV and 15 mA.

Variable temperature XRPD data are collected using a Huber Imaging Plate Guinier Camera 670 employing Ni-filtered $CuK\alpha_1$ radiation (λ=1.5405981 Å) produced at 40 kV and 20 mA by a Philips PW1120/00 generator fitted with a Huber long fine-focus tube PW2273/20 and a Huber Guinier Monochromator Series 611/15. The original powder is packed into a Lindemann capillary (Hilgenberg, Germany) with an internal diameter of 1 mm and a wall thickness of 0.01 mm. The sample is heated at an average rate of 5 $Kmin^{-1}$ using a Huber High Temperature Controller HTC 9634 unit with the capillary rotation device 670.2. The temperature is held constant at selected intervals for 10 min while the sample is exposed to X-rays and multiple scans were recorded. A 2θ-range of 4.00-100.0° is used with a step size of 0.005°2θ.

In certain embodiments wherein the solid form is a solvate, such as a hydrate, the DSC thermogram reveals endothermic transitions. In accordance with the observed DSC transitions, TGA analysis indicates stages of weight change corresponding to desolvation or dehydration and/or melting of the sample. In the case of hydrates, these results are in harmony with Karl Fisher titration data which indicate the water content of the sample.

The moisture sorption profile of a sample can be generated to assess the stability of a solid form is stable over a range of relative humidities. In certain embodiments, the change in moisture content over 10.0 to 95.0% relative humidity is small. In other embodiments the change in moisture content over 10.0 to 95.0% relative humidity is reversible.

In certain embodiments, the XRPD pattern of a sample of solid form indicates that the sample has a well-defined crystal structure and a high degree of crystallinity.

Example 3

Powder X-Ray Diffraction

Powder X-ray diffraction analysis was performed on free flowing powder samples of 4-OH-DIPT hemi-glutarate hydrochloride. Samples were placed in a Si zero background holder, and a preliminary scan in the 2θ range of 5-120° was performed to determine the extent of the crystallinity, and the appropriate settings to use for the full scan. The parameters used were as follows.

Incident optics: Soller slit=0.04 rad, Programmable Divergence Slit, fixed to 10 mm, Beam mask=20 mm, Anti-scatter slit=2°.

Diffracted optics: Soller slit=0.04 rad, Ni Kβ filter.

2 theta range: 5-70°, step size=0.0334°, 0.5 s $step^{-1}$.

Figure 2:
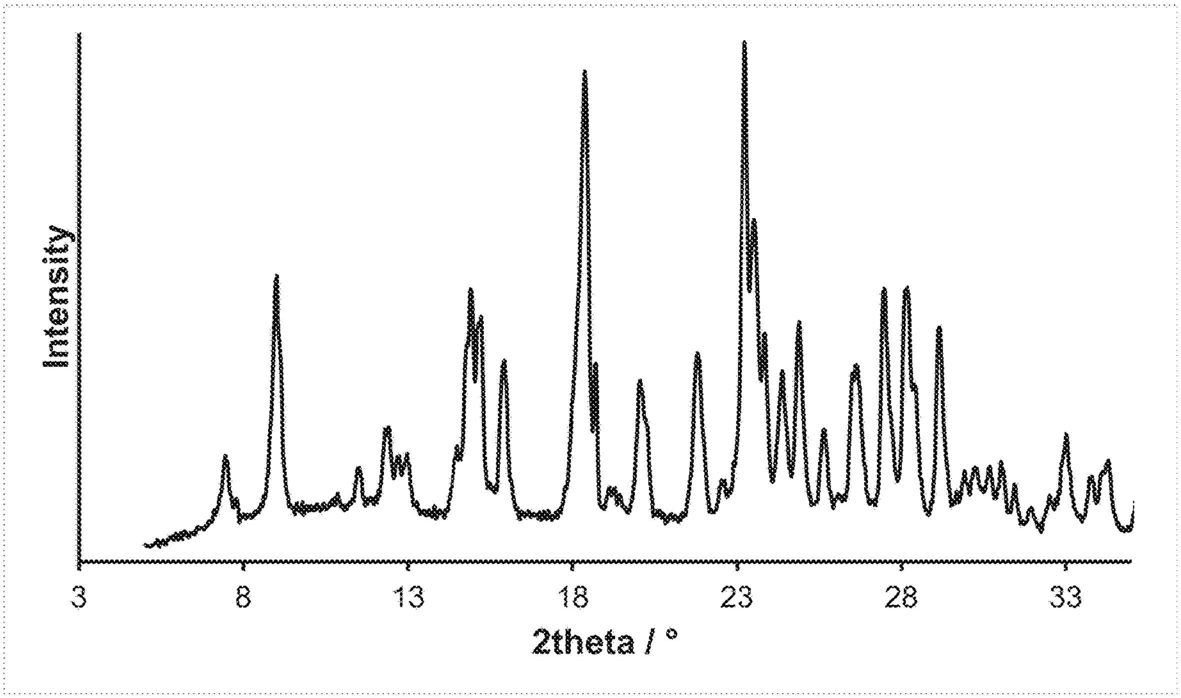
FIG. 2 is a plot of intensity versus 2θ, illustrating an expanded view of the 2 theta region from 3° to 33° of the plot in FIG. 1.

A stacked diffractogram plot of the samples is provided in FIG. 1, and FIG. 2 provides an expanded view of the 2 theta region from 3° to 33°.

The solid form of crystalline 4-OH-DIPT hemi-glutarate hydrochloride analyzed is listed in Table 5.

TABLE 5

| | |
|---|---|
| Solid form of 4-OH-DIPT hemi-glutarate HCl | FIG. 1 |

Example 4

Synthesis of 4-OH-DIPT Hemi-Glutarate Hydrochloride

Materials and Methods

Chemicals were purchased primarily from Sigma-Aldrich (Merck Life Science U.K. Ltd, The Old Brickyard, New Rd, Gillingham, Dorset SP8 4XT, U.K.); Alfa Aesar, Heysham, Morecambe, Lancashire LA3 2XY and were used without further purification. Solvents were purchased as anhydrous. Petrol (pet ether) was the alkane fraction boiling between 40-60° C.

TLC was carried out using aluminum plates pre-coated with silica gel (Kieselgel 60 F254, 0.2 mm, Merck, Darmstadt, Germany). Visualisation was by UV light.

$^1H$ NMR spectra were recorded on a Bruker Avance BVT3200 spectrometer using the residual proton(s) in the deuterated solvents as internal standards.

HPLC analyses were performed with a Shimadzu Prominence instrument (Shimadzu UK Ltd., Unit 1A Mill Court, Featherstone Road, Milton Keynes MK12 5RD, U.K.) with diode array detection and a Kinetex EVO C18, 5 μm, 250 mm×4.6 mm column. Chiral HPLC analysis were performed using a Phenomenex Lux Cellulose 2, 250 mm×4.6 mm column.

LC-MS analyses were performed on a Shimadzu 2020 instrument operating in positive or negative ESI mode with UV detection at 254 nm.

Automated chromatography was performed on a Biotage Selekt purification system (Biotage GB Limited, Distribution Way, Dyffryn Business Park, Ystrad Mynach, Hengoed, Mid Glamorgan CF82 7TS, Wales).

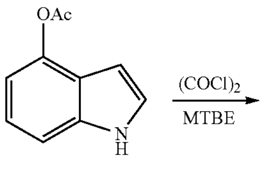

-continued

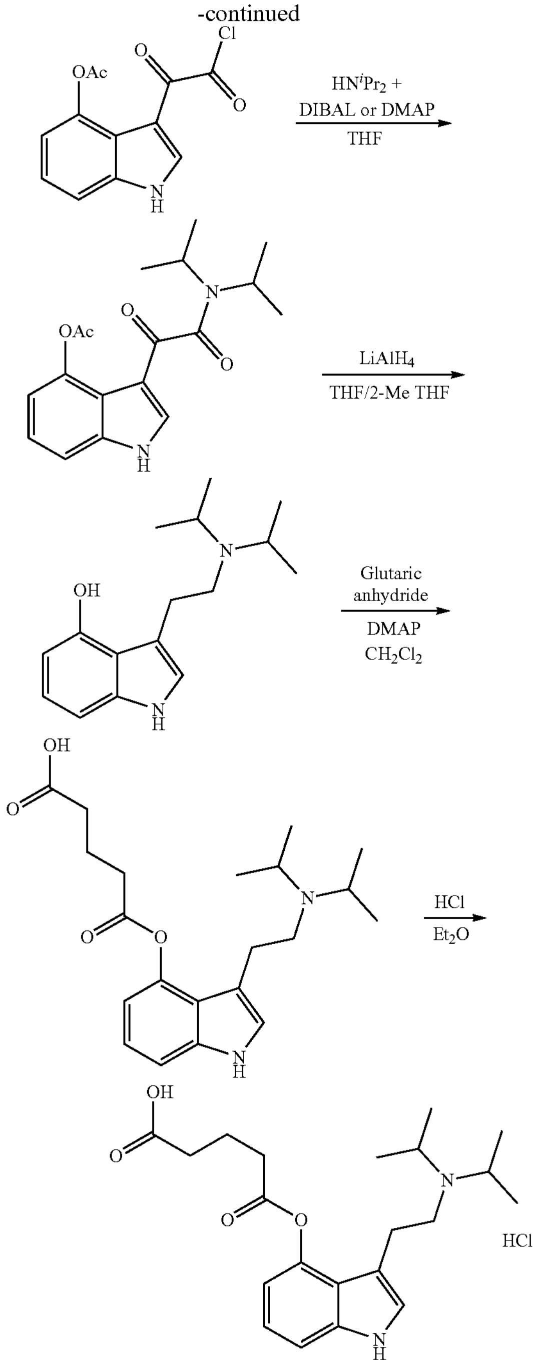

Step 1: Synthesis of 3-(2-chloro-2-oxoacetyl)-1H-indol-4-yl acetate

A mixture of 1H-indol-4-yl acetate (20.0 g, 114.2 mmol) in methyl tert-butyl ether (MTBE, 120 mL) was added slowly to a stirred mixture of oxalyl chloride (17.4 g, 11.6 mL, 137.0 mmol) in MTBE (40 mL) at 0° C. under an atmosphere of $N_2$. The mixture was warmed to rt and stirred for 2 h during which time, a precipitate formed. Heptane (100 mL) was added, the product was collected by filtration, and the filter cake was washed with heptane (2×50 mL), and dried to give 3-(2-chloro-2-oxoacetyl)-1H-indol-4-yl acetate (25.6 g, 84%) as a solid. Mpt: 130-135° C.; LC-MS: m/z 262.05 (as methyl ester), consistent for protonated parent ion $[M+H]^+$.

Step 2: Synthesis of 3-(2-(diisopropylamino)-2-oxoacetyl)-1H-indol-4-yl acetate Using DIBAL To diisopropylamine (4.37 g, 6.05 mL, 45.2 mmol) in THF (100 mL) at rt under an atmosphere of $N_2$ was added DIBAL-H, 1M in THF (41.4 mL, 41.4 mmol). The mixture was stirred at rt for 3 h, then a mixture of 3-(2-chloro-2-oxoacetyl)-1H-indol-4-yl acetate (10.0 g, 37.6 mmol) in THF (60 mL) was cautiously added in portions via a dropping funnel, allowing evolved HCl to vent. The colored mixture was stirred at rt overnight, then the solvent was removed under reduced pressure, and the residue taken up in DCM (100 mL), transferred to a separating funnel and washed with saturated aqueous Rochelle's salt solution (2×100 mL). The aqueous phase was extracted with DCM (100 mL) and the combined organic layers were washed with $H_2O$ (4×100 mL), saturated brine (100 mL), dried ($MgSO_4$), filtered and the filtrate was concentrated under reduced pressure to give 3-(2-(diisopropylamino)-2-oxoacetyl)-1H-indol-4-yl acetate (7.63 g, 61%) as a solid. Mpt: 233-235° C.; LC-MS: m/z=331.20 $[M+H]^+$; $^1H$ NMR (300 MHz, DMSO-$d_6$) δ 12.4 (s, 1H, NH), 7.97 (s, 1H, ArH), 7.47 (dd, J=8.2, 1.0 Hz, 1H, ArH), 7.30 (pseudo t, J=7.9 Hz, 1H, ArH), 6.92 (dd, J=7.7, 1.0 Hz, 1H, ArH), 3.65 (m, 2H, 2×CH), 2.34 (s, 3H, Ac), 1.46 (d, J=6.7 Hz, 6H, 2×$CH_3$), 1.09 (d, J=6.6 Hz, 6H, 2×$CH_3$); $^{13}C$ NMR (75.5 MHz, DMSO-$d_6$) δ 186.0, 169.7, 167.8, 144.5, 139.7, 138.6, 124.6, 115.9, 113.2, 111.2, 50.1, 45.1, 30.9, 21.7, 20.4.

Alternative Synthesis of 3-(2-(diisopropylamino)-2-oxoacetyl)-1H-indol-4-yl acetate Using DMAP To a mixture of 3-(2-chloro-2-oxoacetyl)-1H-indol-4-yl acetate (5.00 g, 18.9 mmol) in THF (60 mL) was added diisopropylamine (4.09 g, 5.7 mL, 40.5 mmol) followed by DMAP (120 mg, 0.94 mmol). The mixture was stirred at rt overnight, then silica gel (ca. 5 g) was added and the solvent was removed under reduced pressure. The residue was loaded onto a pad of silica gel and the product was eluted with THE (ca. 100 mL), then the filtrate was evaporated under reduced pressure to give 3-(2-(diisopropylamino)-2-oxoacetyl)-1H-indol-4-yl acetate (2.61 g, 42%) as a solid.

Step 3: Synthesis of 3-(2-(diisopropylamino)ethyl)-1H-indol-4-ol 3-(2-(Diisopropylamino)-2-oxoacetyl)-1H-indol-4-yl acetate (7.63 g, 23.1 mmol) was suspended in 2-methyltetrahydrofuran (120 mL) and the mixture was stirred at rt under an atmosphere of $N_2$. $LiAlH_4$, 2.4M in THF (35.7 mL, 86.7 mmol) was added dropwise (caution), the temperature increased to ~50° C. and a thick precipitate formed which dissolved once addition was nearing completion. The mixture was heated to 80° C. and stirred for 4 h (note: the colored solution quickly became clear orange and gradually pale yellow over time). The mixture was cooled to 0° C., and quenched cautiously with THF/$H_2O$ (10:3, v/v, 26 mL) to give a thick precipitate. Silica gel (5 g) and $Na_2SO_4$ (5 g) were added followed by DCM/MeOH (9:1 60 mL). The mixture became green upon stirring and was filtered through Celite, washing with DCM/MeOH (9:1, v/v, 2×60 mL). The filtrate was concentrated under reduced pressure to give a pale-yellow semi-solid. The residue was dissolved in a minimal amount of DCM (approx. 10 mL) and heptane was added in 1 mL volumes whilst swirling until a cloudy suspension persisted alongside a brown tarry residue. The suspension was decanted to a separate vessel and the process repeated twice. The combined decanted fractions were evaporated to give 3-(2-(diisopropylamino)ethyl)-1H-indol-4-ol (4.18 g, 70%) as an off-white semi-solid. LC-MS m/z=261.15 $[M+H]^+$; $^1H$ NMR (300 MHz, $CDCl_3$) δ 12.90 (br. s, 1H, NH), 7.82 (s, 1H, ArH), 6.95 (t, J=7.9 Hz, 1H), 6.75 (dd, J=8.1, 0.9 Hz, 1H, ArH), 6.72 (s, 1H, OH), 6.47 (dd, J=7.6, 0.9 Hz, 1H, ArH), 3.04 (m, 2H, 2×CH), 2.90 (m, 2H, $CH_2$), 2.71 (m, 2H, $CH_2$), 0.95 (d, J=6.5 Hz, 4×12H, $CH_3$); $^{13}C$ NMR (75.5 MHz, $CDCl_3$) δ 151.9, 138.5, 123.4, 120.6, 118.9, 114.5, 106.5, 102.4, 50.4, 48.3, 27.8, 19.4.

Step 4: Synthesis of 5-((3-(2-(diisopropylamino)ethyl)-1H-indol-4-yl)oxy)-5-oxopentanoic acid To a stirred mixture of 3-(2-(diisopropylamino)ethyl)-1H-indol-4-ol (4.00 g, 15.4 mmol) in DCM (20 mL) was added glutaric anhydride (3.16 g, 27.7 mmol) in small portions, followed by DMAP (564 mg, 4.61 mmol) in the same manner. A solid aggregate was rapidly formed which dispersed within an hour to give a white precipitate. The mixture was stirred at rt overnight, then concentrated under reduced pressure and EtOH (50 mL) was added with stirring briefly to break up the solid. The product was collected by filtration and the filter cake was washed with EtOH (2×50 mL) and DCM (20 mL). The resulting solid was dried in vacuo to give 5-((3-(2-(diisopropylamino)ethyl)-1H-indol-4-yl)oxy)-5-oxopentanoic acid (3.68 g, 64%) as a solid. Mpt 153-155° C.; LC-MS m/z=375.20 $[M+H]^+$; $^1H$ NMR (300 MHz, DMSO-$d_6$) δ 11.04 (br. s, 1H, NH), 7.23 (dd, J=8.2, 0.9 Hz, 1H, ArH), 7.17 (d, J=2.3 Hz, 1H, ArH), 7.03 (pseudo t, J=7.9 Hz, 1H, ArH), 6.65 (dd, J=7.6, 0.8 Hz, 1H, ArH), 3.11 (heptet, J=6.6 Hz, 1H, 2×CH), 2.71 (m, 6H, 3×$CH_2$), 2.32 (t, J=7.2 Hz, 2H, $CH_2$), 1.89 (m, 2H, $CH_2$), 1.02 (d, J=6.6 Hz, 12H, 4×$CH_3$); $^{13}C$ NMR (75.5 MHz, DMSO-$d_6$) δ174.6, 172.4, 144.2, 138.9, 123.8, 121.3, 120.1, 111.9, 111.7, 109.8, 49.0, 46.7, 33.8, 33.3, 27.7, 20.7, 20.5.

Step 5: Synthesis of 5-((3-(2-(diisopropylamino)ethyl)-1H-indol-4-yl)oxy)-5-oxopentanoic acid HCl Salt 5-((3-(2-(Diisopropylamino)ethyl)-1H-indol-4-yl)oxy)-5-oxopentanoic acid (4.17 g, 11.15 mmol) was suspended in $Et_2O$ (44 mL). 2M HCl in $Et_2O$ (6.13 mL, 12.3 mmol) was added dropwise with vigorous stirring. The reaction mixture was stirred at rt for 10 min, then the precipitate was left to settle. The supernatant was removed by decanting and replaced by fresh $Et_2O$ (30 mL). The precipitate was collected by filtration, and the filter cake was washed with $Et_2O$ (2×20 mL) to give of 5-((3-(2-(diisopropylamino)ethyl)-1H-indol-4-yl)oxy)-5-oxopentanoic acid hydrochloride (4.15 g, 91%) as a white solid. Mpt 162-166° C.; LC-MS m/z=375.1 $[M+H]^+$; $^1H$ NMR (300 MHz, DMSO-$d_6$) δ 11.31 (br. s, 1H, NH), 9.94 (br. m, 1H, $NH^+$), 7.38 (d, J=2.4 Hz, 1H, ArH), 7.27 (dd, J=8.2, 0.9 Hz, 1H, ArH), 7.07 (t, J=7.9 Hz, 1H, ArH), 6.71 (dd, J=7.9, 0.8 Hz, 1H), 3.66 (m, 2H, 2×CH), 3.30 (m, 2H, $CH_2$), 3.17 (m, 2H, $CH_2$), 2.90 (t, J=7.4 Hz, 2H, $CH_2$), 2.41 (t, J=7.5 Hz, 2H, $CH_2$) 1.87 (m, 2H, $CH_2$), 1.38 (d, J=6.5 Hz, 6H, 2×$CH_3$), 1.33 (d, J=6.4 Hz, 6H, 2×$CH_3$); $^{13}C$ NMR: (75.5 MHz, DMSO-$d_6$) δ 174.6, 172.6, 144.0, 138.8, 124.3, 121.8, 119.6, 112.3, 109.9, 108.7, 54.7, 47.5, 33.1, 24.2, 20.3.

Example 5

Evaluation of Metabolic Stability in Human Liver Microsomes

Microsomal Assay: Human liver microsomes (20 mg/mL) are obtained. β-nicotinamide adenine dinucleotide phosphate, reduced form (NADPH), magnesium chloride ($MgCl_2$), and dimethyl sulfoxide (DMSO) are purchased.

Determination of Metabolic Stability: 7.5 mM stock preparations of test compounds of the disclosed compounds are prepared in a suitable solvent, such as DMSO. The 7.5 mM stock preparations are diluted to 12.5-50 μM in acetonitrile (ACN). The 20 mg/mL human liver microsomes are diluted to 0.625 mg/mL in 0.1 M potassium phosphate buffer, pH 7.4, containing 3 mM $MgCl_2$. The diluted microsomes are added to wells of a 96-well deep-well polypropylene plate in triplicate. A 10 pL aliquot of the 12.5-50 μM test compound is added to the microsomes and the mixture is pre-warmed for 10 minutes. Reactions are initiated by addition of pre-warmed NADPH solution. The final reaction volume is 0.5 mL and contains 4.0 mg/mL human liver microsomes, 0.25 UM test compound, and 2 mM NADPH in 0.1 M potassium phosphate buffer, pH 7.4, and 3 mM $MgCl_2$. The reaction mixtures are incubated at 37° C., and 50 pL aliquots are removed at 0, 5, 10, 20, and 30 minutes and added to shallow-well 96-well plates which contain 50 μL of ice-cold ACN (acetonitrile) with internal standard to stop the reactions. The plates are stored at 4° C. for 20 minutes after which 100 μL of water is added to the wells of the plate before centrifugation to pellet precipitated proteins. Supernatants are transferred to another 96-well plate and analyzed for amounts of parent remaining by LC-MS/MS using an Applied Bio-systems API 4000 mass spectrometer. The same procedure is followed for the positive control, 7-ethoxycoumarin (1 μM). Testing is done in triplicate.

Data analysis: The in vitro $T_{1/2}$s for test compounds are calculated from the slopes of the linear regression of % parent remaining (In) vs incubation time relationship.

$$\text{in vitro } T_{1/2} = 0.693/k$$

k=−[slope of linear regression of % parent remaining (In) vs incubation time] The apparent intrinsic clearance is calculated using the following equation:

$$CL_{int}(\text{mL/min/kg}) = (0.693/\text{in vitro } T)(\text{Incubation Volume/mg of microsomes})(45 \text{ mg microsomes/gram of liver})(20 \text{ gm of liver/kg } b.w.)$$

Data Analysis is Performed Using Microsoft Excel Software.

In these experiments, values equal to or more than a 15% increase in half-life are considered to be a significant difference if the apparent intrinsic clearance ratio (4-OH-DIPT hemi-glutarate salt or solid form/comparator solid form, 4-OH-DIPT hemi-succinate salt or solid form/comparator solid form, 4-OH-DIPT hemi-succinate hydrochloride solid form/comparator solid form, 4-OH-DIPT hemi-glutarate hydrochloride solid form/comparator solid form) is >1.15 or <0.85, then there is considered to be significant differentiation.

Example 6

Oral Bioavailability in Rats

Pharmacokinetics of test articles following a single intravenous or oral administration in rats: A pharmacokinetic (PK) study is performed in three male Sprague-Dawley (SD) rats following intravenous (IV) and oral (PO) administration of a compound disclosed herein. Test compounds are measured in plasma.

A detailed description of the in vivo methods:

Rat Strain

Rats used in these studies are supplied by Charles River (Margate UK) and are specific pathogen free. The strain of rats is Sprague Dawley. Male rats are 175-225 g on receipt and are allowed to acclimatise for 5-7 days.

Animal Housing

Rats are group housed in sterilised individual ventilated cages that expose the animals at all times to HEPA filtered sterile air. Animals will have free access to food and water (sterile) and will have sterile aspen chip bedding (at least once weekly). The room temperature is 22° C.+/−1° C., with a relative humidity of 60% and maximum background noise of 56 dB. Rats are exposed to 12 hour light/dark cycles.

Treatment

The test articles are administered in a suitable dose volume for intravenous (IV) or (PO) for oral routes of administration.

Single IV/PO Dose Pharmacokinetics Study in Rats

Each test article is administered as a single IV bolus (via a lateral tail-vein) or a single oral gavage in cohorts of 3 rats per route. Following dose administrations, a 100 μL whole blood sample (EDTA) is collected via the tail-vein at appropriate time-points. The blood is centrifuged to separate plasma. Approximately 40 μL of plasma is dispensed per time-point, per rat, in a 96 well plate and frozen until analysis. Bioanalysis is carried out on plasma samples.

Dose Formulation Samples

Dose formulation samples are diluted in two steps with 50:50 (v/v) methanol/water to an appropriate concentration, then diluted 10:90 (v/v) with control matrix to match to the calibration standard in plasma.

Sample Extraction Procedure

Calibration and QC standards, incurred samples, blank matrix and dose formulation samples are extracted by protein precipitation, via the addition of a bespoke acetonitrile (ACN)-based Internal Standard (IS) solution, containing several compounds and including Metoprolol and Rosuvastatin, both of which are monitored for during analysis. Following centrifugation, a 40 μL aliquot of supernatant is diluted by the addition of 80 μL water. The prepared sample extracts are analysed by LC-MS/MS. In one embodiment, the oral bioavailability of a disclosed crystalline solid form is superior to an amorphous or known crystalline form.

Example 7

Biological Assays and Methods

Head-Twitch Response (HTR). The head-twitch response assay is performed as is known to those of skill in the art using both male and female C57BL/6J mice (2 per treatment). The mice are obtained and are approximately 8 weeks old at the time of the experiments. Compounds are administered via intraperitoneal injection (5 mL/kg) using 0.9% saline as the vehicle. As a positive control, psilocybin (2 mg/kg in saline) is utilized. Behavior is videotaped, later scored by two blinded observers, and the results are averaged (Pearson correlation coefficient=0.93).

Serotonin and Opioid Receptor Functional Assays. Functional assay screens at 5-HT and opioid receptors are performed in parallel using the same compound dilutions and 384-well format high-throughput assay platforms. Assays assess activity at all human isoforms of the receptors, except where noted for the mouse 5-$HT_{2A}$ receptor. Receptor constructs in pcDNA vectors are generated from the Presto-Tango GPCR library with minor modifications. All compounds are serially diluted in drug buffer (HBSS, 20 mM HEPES, pH 7.4 supplemented with 0.1% bovine serum albumin and 0.01% ascorbic acid) and dispensed into 384-well assay plates using a $FLIPR^{TETRA}$ (Molecular Devices). Every plate includes a positive control such as 5-HT (for all 5-HT receptors), DADLE (DOR), salvinorin A (KOR), and DAMGO (MOR). For measurements of 5-HT2A, 5-HT2B, and 5-HT2C Gq-mediated calcium flux function, HEK Flp-In 293 T-Rex stable cell lines (Invitrogen) are loaded with Fluo-4 dye for one hour, stimulated with compounds and read for baseline (0-10 seconds) and peak fold-over-basal fluorescence (5 minutes) at 25° C. on the $FLIPR^{TETRA}$. For measurement of 5-HT6 and 5-HT7a functional assays, Gs-mediated CAMP accumulation is detected using the split-luciferase GloSensor assay in HEKT cells measuring luminescence on a Microbeta Trilux (Perkin Elmer) with a 15 min drug incubation at 25° C. For 5-HT1A, 5-HT1B, 5-HT1F, MOR, KOR, and DOR functional assays, Gi/o-mediated CAMP inhibition is measured using the split-luciferase GloSensor assay in HEKT cells, conducted similarly as above, but in combination with either 0.3 μM isoproterenol (5-HT1A, 5-HT1B, 5-HT1F) or 1 μM forskolin (MOR, KOR, and DOR) to stimulate endogenous CAMP accumulation. For measurement of 5-HT1D, 5-HT1E, 5-HT4, and 5-HT5A functional assays, P-arrestin2 recruitment is measured by the Tango assay utilizing HTLA cells expressing TEV fused-P-arrestin2, as described previously with minor modifications. Data for all assays is plotted and non-linear regression is performed using "log (agonist) vs. response" in Graphpad Prism to yield Emax and $EC_{50}$ parameter estimates.

$5HT_{2A}$ Sensor Assays. HEK293T (ATCC) $5HT_{2A}$ sensor stable line (sLightl.3s) is generated via lentiviral transduction of HIV-EF1α-sLight1.3 and propagated from a single colony. Lentivirus is produced using $2^{nd}$ generation lentiviral plasmids pHIV-EF1α-sLight1.3, pHCMV-G, and pCMV-deltaR8.2.

For the screening of the compounds, sLightl.3s cells are plated in 96-well plates at a density of 40000 24-hours prior to imaging. On the day of imaging, compounds in DMSO are diluted from the 100 mM stock preparations to working concentrations of 1 mM, 100 mM and 1 μM with a DMSO concentration of 1%. Immediately prior to imaging, cells growing in DMEM (Gibco) are washed 2× with HBSS (Gibco) and in agonist mode 180 μL of HBSS or in antagonist mode 160 μL of HBSS is added to each well after the final wash. For agonist mode, images are taken before and after the addition of the 20 μL compound working preparation into the wells containing 180 μL HBSS. This produces final compound concentrations of 100 mM, 10 mM and 100 nM with a DMSO concentration of 0.1%. For antagonist mode, images are taken before and after addition of 20 μL of 900 nM 5-HT and again after 20 μL of the compound working preparation to produce final concentrations of 100 nM for 5HT and 100 mM, 10 mM and 100 nM for the compounds with a DMSO concentration of 0.1%. Each compound is tested in triplicate (3 wells) for each concentration (100 mM, 10 mM and 100 nM). Additionally, within each plate, 100 nM 5HT and 0.1% DMSO controls are also imaged.

Imaging is performed using the Leica DMi8 inverted microscope with a 40× objective using the FITC preset with an excitation of 460 nm and emission of 512-542 nm. For each well, the cellular membrane where the 5HT2A sensor is targeted is autofocused using the adaptive focus controls and 5 images from different regions within the well are taken with each image processed from a 2×2 binning.

For data processing, the membranes from each image are segmented and analyzed using a custom algorithm written in MATFAB producing a single raw fluorescence intensity value. For each well the 5 raw fluorescence intensity values generated from the 5 images are averaged and the change in fluorescence intensity (dFF) is calculated as:

$$dFF=(F_{sat}-F_{apo})/F_{apo}$$

For both agonist and antagonist modes, the fluorescence intensity values before compound addition in FIBSS only are used as the $F_{apo}$ values while the fluorescence intensity values after compound addition are used as the $F_{sat}$ values.

For agonist mode, data are as percent activation relative to 5HT, where 0 is the average of the DMSO wells and 100 is the average of the 100 μM 5HT wells. For antagonist mode, the inactivation score is calculated as:

$$\text{Inactivation score}=(dFFF(\text{Compound}+5HT)-dFF(5HT))/dFF(5HT)$$

Plasticity Effects: Treatment of rat embryonic cortical neurons with compounds disclosed herein is evaluated for increased dendritic arbor complexity at 6 days in vitro (DIV6) as measured by Sholl analysis. The effect of the present compounds on dendritic growth can be determined to be 5-HT2A-dependent, if pretreatment with ketanserin—a $5\text{-HT}_{2A}$ antagonist—inhibits their effects.

In addition to promoting dendritic growth, the present compounds also are evaluated for increased dendritic spine density to a comparable extent as ibogaine in mature cortical cultures (DIV20). The effects of the compounds on cortical dendritic spine dynamics in vivo using transcranial 2-photon imaging is assessed. First, spines are imaged on specific dendritic loci defined by their relation to blood vessel and dendritic architectures. Next, the animals are systemically administered vehicle, a compound of the present invention, or a positive control compound. After 24 h, the same dendritic segments are re-imaged, and the number of spines gained or lost is quantified. Examples of the presently disclosed compounds increase spine formation in mouse primary sensory cortex, suggesting that the present compounds support neuronal plasticity.

As increased cortical structural plasticity in the anterior parts of the brain mediates the sustained (>24 h) antidepressant-like effects of ketamine and play a role in the therapeutic effects of 5-HT2A agonists, the impact of the present compounds on forced swim test (FST) behavior is evaluated. First, a pretest is used to induce a depressive phenotype. Compounds are administered 24 h after the pre-test, and the FST is performed 24 h and 7 d post compound administration. Effective compounds of the invention, like ketamine, significantly reduce immobility 24 h after administration.

Dendritogenesis Assays. Compounds disclosed herein are evaluated for their ability to increase dendritic arbor complexity in cultures of cortical neurons using a phenotypic assay. Following treatment, neurons are fixed and visualized using an antibody against MAP2—a cytoskeletal protein localized to the somatodendritic compartment of neurons. Sholl analysis is then performed, and the maximum number of crossings ($N_{max}$) is used as a quantitative metric of dendritic arbor complexity. For statistical comparisons between specific compounds, the raw $N_{max}$ values are compared. Percent efficacies are determined by setting the $N_{max}$ values for the vehicle (DMSO) and positive (ketamine) controls equal to 0% and 100%, respectively.

Animals. For the dendritogenesis experiments, timed pregnant Sprague Dawley rats are obtained. For the head-twitch response assay, male and female C57BL/6J mice are obtained.

Dendritogenesis—Sholl Analysis. Dendritogenesis experiments are performed following a previously published methods with slight modifications. Neurons are plated in 96-well format (200 μL of media per well) at a density of approximately 15,000 cells/well in Neurobasal (Life Technologies) containing 1% penicillin-streptomycin, 10% heat-inactivated fetal bovine serum, and 0.5 mM glutamine. After 24 h, the medium is replaced with Neurobasal containing lx B27 supplement (Life Technologies), 1% penicillin-streptomycin, 0.5 mM glutamine, and 12.5 pM glutamate. After 3 days in vitro (DIV3), the cells are treated with compounds. All compounds tested in the dendritogenesis assays are treated at 10 pM. Stock preparations of the compounds in DMSO are first diluted 100-fold in Neurobasal before an additional 10-fold dilution into each well (total dilution=1:1000; 0.1% DMSO concentration). Treatments are randomized. After 1 h, the media is removed and replaced with new Neurobasal media containing 1×B27 supplement, 1% penicillin-streptomycin, 0.5 mM glutamine, and 12.5 mM glutamate. The cells are allowed to grow for an additional 71 h. At that time, neurons are fixed by removing 80% of the media and replacing it with a volume of 4% aqueous paraformaldehyde (Alfa Aesar) equal to 50% of the working volume of the well. Then, the cells are incubated at room temperature for 20 min before the fixative is aspirated and each well washed twice with DPBS. Cells are permeabilized using 0.2% Triton X-100 (ThermoFisher) in DPBS for 20 minutes at room temperature without shaking. Plates are blocked with antibody diluting buffer (ADB) containing 2% bovine serum albumin (BSA) in DPBS for 1 h at room temperature. Then, plates are incubated overnight at 4° C. with gentle shaking in ADB containing a chicken anti-MAP2 antibody (1:10,000; EnCor, CPCA-MAP2). The next day, plates are washed three times with DPBS and once with 2% ADB in DPBS. Plates are incubated for 1 h at room temperature in ADB containing an anti-chicken IgG secondary antibody conjugated to Alexa Fluor 488 (Life Technologies, 1:500) and washed five times with DPBS. After the final wash, 100 μL of DPBS is added per well and imaged on an ImageXpress Micro XL High-Content Screening System (Molecular Devices, Sunnyvale, CA) with a 20× objective. Images are analyzed using ImageJ Fiji (version 1.51 W). First, images corresponding to each treatment are sorted into individual folders that are then blinded for data analysis. Plate controls (both positive and negative) are used to ensure that the assay is working properly as well as to visually determine appropriate numerical values for brightness/contrast and thresholding to be applied universally to the remainder of the randomized images. Next, the brightness/contrast settings are applied, and approximately 1-2 individual pyramidal-like neurons per image (i.e., no bipolar neurons) are selected using the rectangular selection tool and saved as separate files. Neurons are selected that do not overlap extensively with other cells or extend far beyond the field of view.

In Vivo Spine Dynamics. Male and female Thyl-GFP-M line mice (n=5 per condition) are purchased and maintained. In vivo transcranial two-photon imaging and data analysis are performed as previously described. Briefly, mice are anesthetized with an intraperitoneal (i.p.) injection of a mixture of ketamine (87 mg/kg) and xylazine (8.7 mg/kg). A small region of the exposed skull is manually thinned down to 20-30 pm for optical access. Spines on apical dendrites in mouse primary sensory cortices are imaged using a Bruker Ultima IV two-photon microscope equipped with an Olympus water-immersion objective (40×, NA=0.8) and a Ti: Sapphire laser (Spectra-Physics Mai-Tai, excitation wavelength 920 nm). Images are taken at a zoom of 4.0 (pixel size 0.143×0.143 pm) and Z-step size of 0.7 pm. The mice receive an i.p. injection (injection volume=5 mL/kg) of a disclosed compound immediately after they recover from anesthesia given prior to the first imaging session. The animals are re-imaged 24 h after drug administration. Dendritic spine dynamics are analyzed using ImageJ. Spine formation and elimination are quantified as percentages of spine number on day 0.

Forced Swim Test (FST). Male C57/BL6J mice (9-10 weeks old at time of experiment) are obtained. After 1 week in the vivarium each mouse is handled for approximately 1 minute by the experimenter for 3 consecutive days leading up to the first FST. All experiments are carried out by the same experimenter who performs handling. During the FST, mice undergo a 6 min swim session in a clear Plexiglas cylinder 40 cm tall, 20 cm in diameter, and filled with 30 cm of 24±1° C. water. Fresh water is used for every mouse. After handling and habituation to the experimenter, drug-naive mice first undergo a pretest swim to more reliably induce a depressive phenotype in the subsequent FST sessions. Immobility scores for all mice are determined after the pre-test and mice are randomly assigned to treatment groups to generate groups with similar average immobility scores to be used for the following two FST sessions. The next day, the animals receive intraperitoneal injections of experimental compounds (20 mg/kg), a positive control (ketamine, 3 mg/kg), or vehicle (saline). The animals were subjected to the FST 30 mins after injection and then returned to their home cages. All FSTs are performed between the hours of 8 am and 1 pm. Experiments are video-recorded and manually scored offline. Immobility time—defined as passive floating or remaining motionless with no activity other than that needed to keep the mouse's head above water—is scored for the last 4 min of the 6 min trial.

Statistical analysis. Treatments are randomized, and data are analyzed by experimenters blinded to treatment conditions. Statistical analyses are performed using GraphPad Prism (version 8.1.2). The specific tests are F-statistics and degrees of freedom. All comparisons are planned prior to performing each experiment. For dendritogenesis experiments a one way ANOVA with Dunnett's post hoc test is deemed most appropriate. Ketamine is included as a positive control to ensure that the assay is working properly.

Alcohol Use Disorder Model: To assess the anti-addictive potential of the present compounds, an alcohol drinking paradigm that models heavy alcohol use and binge drinking behavior in humans is employed. Using a 2-bottle choice setup (20% ethanol (v/v), EtOH vs. water, $H_2O$), mice are subjected to repeated cycles of binge drinking and withdrawal over the course of 7 weeks.

This schedule results in heavy EtOH consumption, binge drinking-like behavior, and generates blood alcohol content equivalent to that of human subjects suffering from alcohol use disorder (AUD). Next, compounds of the disclosure are administered via intraperitoneal injection 3 h prior to a drinking session, and EtOH and $H_2O$ consumption is monitored. Effective compounds of the disclosure robustly reduce binge drinking during the first 4 hours, decreasing EtOH consumption. With exemplary compounds, consumption of ethanol is lower for at least two days following administration with no effect on water intake. Efficacy in this assay suggests the present compounds are useful for the treatment of AUD. In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

The invention claimed is:

1. A crystalline solid form of 4-OH-DIPT hemi-glutarate hydrochloride characterized by having two or more X-ray powder diffraction peaks at diffraction angles 2θ (°) selected from the group consisting of 18.4±0.2, 23.3±0.2, and 24.9±0.2, as measured by X-ray diffractometry by irradiation with Cu-Kα X-rays.

2. The crystalline solid form of claim 1, wherein the crystalline solid form of 4-OH-DIPT hemi-glutarate hydrochloride is characterized by having XRPD peaks at diffraction angles 2θ (°) 18.4±0.2, 23.3±0.2, and 24.9±0.2, as measured by X-ray diffractometry by irradiation with Cu-Kα X-rays.

3. The crystalline solid form of claim 1, wherein the crystalline solid form of 4-OH-DIPT hemi-glutarate hydrochloride is characterized by having two or more XRPD peaks at diffraction angles 2θ (°) selected from the group consisting of 18.4±0.2, 23.3±0.2, 24.9±0.2, 24.3±0.2, and 15.9±0.2, as measured by X-ray diffractometry by irradiation with Cu-Kα X-rays.

4. The crystalline solid form of claim 1, wherein the crystalline solid form of 4-OH-DIPT hemi-glutarate hydrochloride is characterized by having two or more XRPD peaks at diffraction angles 2θ (°) selected from the group consisting of 18.4±0.2, 23.3±0.2, 24.9±0.2, 24.3±0.2, 15.9±0.2, 20.0±0.2, and 26.6±0.2, as measured by X-ray diffractometry by irradiation with Cu-Kα X-rays.

5. The crystalline solid form of claim 1, wherein the crystalline solid form of 4-OH-DIPT hemi-glutarate hydrochloride is characterized by having two or more XRPD peaks at diffraction angles 2θ (°) selected from the group consisting of 18.4±0.2, 23.3±0.2, 24.9±0.2, 24.3±0.2, 15.9±0.2, 20.0±0.2, 26.6±0.2, 15.0±0.2, 28.3±0.2, and 21.8±0.2, as measured by X-ray diffractometry by irradiation with Cu-Kα X-rays.

6. The crystalline solid form of claim 1, wherein the crystalline solid form of 4-OH-DIPT hemi-glutarate hydrochloride is characterized by having two or more XRPD peaks at diffraction angles 2θ (°) selected from the group consisting of 7.4±0.2, 9.0±0.2, 12.4±0.2, 12.9±0.2, 15.0±0.2, 15.9±0.2, 18.4±0.2, 19.2±0.2, 20.0±0.2, 21.8±0.2, 23.3±0.2, 24.3±0.2, 24.9±0.2, 26.6±0.2, 28.3±0.2, 29.2±0.2, 33.0±0.2, 34.2±0.2, and 36.3±0.2, as measured by X-ray diffractometry by irradiation with Cu-Kα X-rays.

* * * * *